United States Patent [19]
Bridges et al.

[11] Patent Number: 5,808,034
[45] Date of Patent: Sep. 15, 1998

[54] PLANT GENE CONSTRUCT COMPRISING MALE FLOWER SPECIFIC PROMOTERS

[75] Inventors: Ian George Bridges, Slater, Iowa; Simon William Jonathan Bright, Bucks, England; Andrew James Greenland, Maidenhead, England; Wolfgang Walter Schuch, Crowthorne, England

[73] Assignee: Zeneca Limited, London, England

[21] Appl. No.: 293,422

[22] Filed: Aug. 22, 1994

Related U.S. Application Data

[63] Continuation of Ser. No. 165,544, Dec. 13, 1993, abandoned, which is a continuation of Ser. No. 824,883, Jan. 22, 1992, abandoned, which is a continuation of Ser. No. 470,654, Jan. 26, 1990, abandoned.

[30] Foreign Application Priority Data

Jan. 26, 1987 [GB] United Kingdom .................. 8901677

[51] Int. Cl.$^6$ .......................... C12N 15/11; C12N 15/82; A01H 1/00
[52] U.S. Cl. ....................... 536/24.1; 536/23.5; 536/23.6; 536/23.7; 47/58; 47/DIG. 1
[58] Field of Search .................................. 800/200, 205, 800/DIG. 56; 435/172.1, 172.3; 536/24.1, 69.1, 69.8, 91, 317, 1, 23.5, 23.6, 23.7; 935/34, 33, 35, 42

[56] References Cited

FOREIGN PATENT DOCUMENTS 0193259   9/1986   European Pat. Off. ....... C12M 18/00

OTHER PUBLICATIONS

Bouillaud et al (1985) Biochem. Biophysic. Res. Comm. vol. 157 #2 pp. 783–792.

Figge et al (1988) Cell vol. 52, pp. 713–722.

Stinson et al (1987) Plant Physiology vol. 83 pp. 442–447.

Eckes et al (1986) Mol. Gen. Genet. vol. 205 pp.14–22.

Wiegard et al (1986) Plant Mol. Biol. vol. 7, pp. 235–243.

*Primary Examiner*—Gene Benzion
*Attorney, Agent, or Firm*—Cushman Darby & Cushman

[57] ABSTRACT

Male sterility is imparted to a plant by a cascade of gene sequences which expresses a protein which disrupts the biosynthesis of viable pollen. Expression of the disrupter protein is restricted to male parts of the plant by an upstream promoter sequence which is specific to male flowers, the male specific promoter being under control of an operator sequence. The cascade also includes a gene encoding a repressor protein specific for that operator. Expression of the repressor protein is under control of a chemically inducible promoter which is inducible by the application to the plant by, spraying or like process, of an exogenous chemical. In the absence of the exogenous chemical inducer, no repressor protein is expressed, resulting in expression of the disrupter protein and, consequently, male sterility. Fertility may be restored to the plant, when required for maintenance of the line, by spraying with the inducer, resulting in expression of the repressor which binds the operator and inhibits expression of the disrupter protein.

8 Claims, 44 Drawing Sheets

MINUS CHEMICAL – disrupter protein moce
ALL PLANTS ARE MALE STERILE

PLUS CHEMICAL – no disrupter protein
ALL PLANTS ARE FERTILE

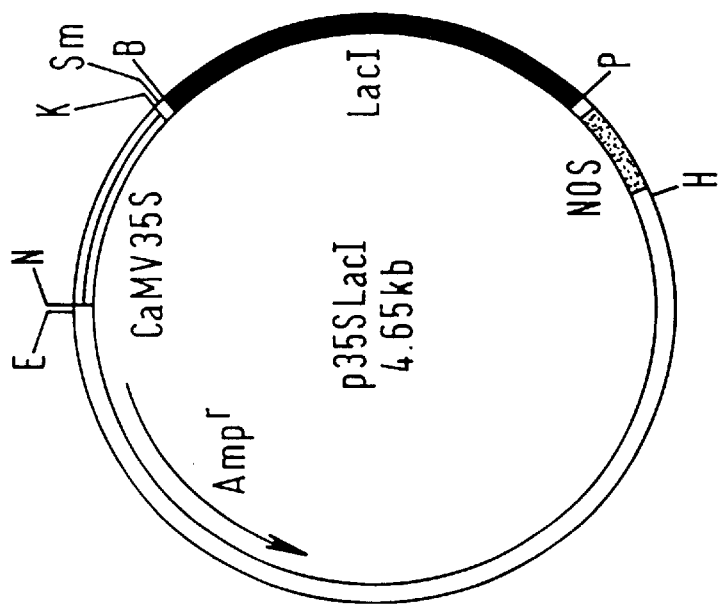
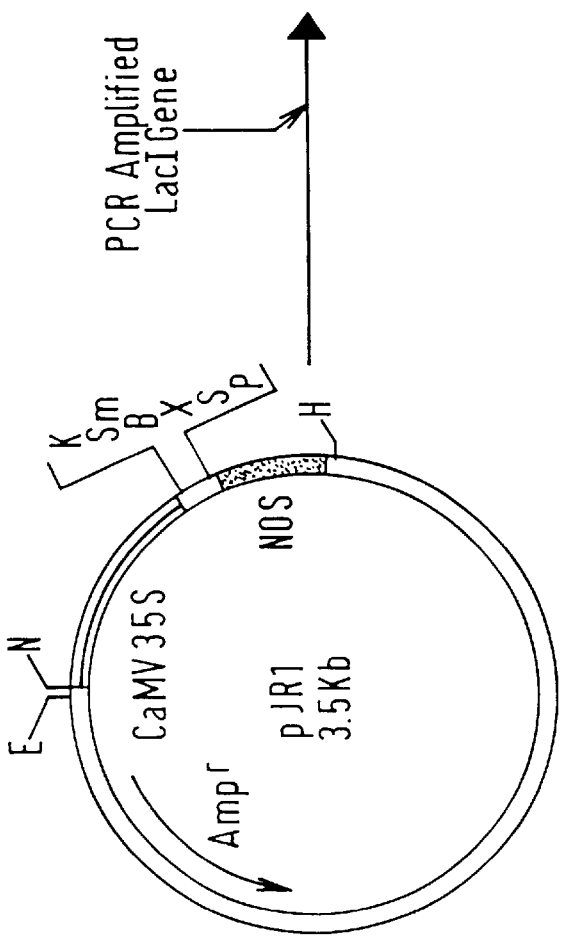
FIG. 10.

FIG. 12A

```
            10           20           30           40           50
            |            |            |            |            |
     XbaI
  1  GTCTAGATATGTTTCTCTTTGGTTCTTGAGTTGACAAGTGGCATGCTAT
 51  TTTTGCTCATGTGAGAAAAATATAGCACCGTTTGTTTCCTTGAAATTGA
101  ATTGCATCCCAATAATCATAATTTAGACATAAACCTAAGTTAATATA
151  TTTGTATATGTAAATATGTTATCCTAAATTATATTATATGAGAGAGATA
201  GTTATACATTACAATTATGATATAGAAGCAAATAGAAGAGTGTGCTAT
251  AAGTTGTACATTGTAAAATTTATAGAAGTATGCAAATTTATAGAATTAATTTTTAT
301  CTTTCACCTCATAAATTTAAGATACACTTATATATAAACTTTGAAAAGTT
351  GTAAAATATCATATTCTAAAAAGAAAAATAAATAGACTATTCTATTAGTTACATTCC
401  AATTCCTTAAAATATAAAAAGAAAATAAATGGGCTTAAGGCTAGTTTGGTGG
451  GCAGGTGGAGGCGATCAATGCCGATGAATCCTCTCGATATTCAATTGAG
501  GGGGTTCATCCCATGAATCTCTATTTACATGTCCACCAAACAAGATTA
551  AATGCAATGATATACAAGATGTGTGGTTGCATATTTTTTAACGGAGATGCA
601  AAACAGTATACAAGATGTGTGGTTGAACCAGAAGATACACATGCCATCTGTATCC
651  AGTTCATGCGTCTGGTCTTGGTGAACTTCATTGATTATGCATTGACAAATAGCAAG
701  ATGAATCAACACAAAAGACTTCATTATGCATTTGACAAATAGCAAG
751  AAGCGCGGGCAACAAAGCCCATCTCCATCATCCATTTTTTCCCACGAT
801  GGCAAGTGGCAGCTCCTGATTAGCTACGCCCATTCCTATGCTATGTGGCA
851  CACCCCAGGATTCTTGTGTGATAGGCCATTGGGCCACGAGGAGCCACGT
```

FIG. 12B

```
 901  CAGACGCCAAGCCACCCCGGGCGAGACCAACCAGCCAATCGCCAGTTCAGGA
 951  AAAGATGACCTGCTATCCAAACCAACTGTATAAAGGCAGCTGCTGTGT
                        ↔      ↔ ↔
1001  TCTGTTTATGACACAGCCATCACACGGCCATACTGCATACACAACACAGAGCA
                                         M  A  A  A  T  M
1051  TCAGAAGGAGCTACGATCTGATCGACATGGCTGCCGCCACCATGG
                                              NcoI
```

___  = CAT and TATA sequences.

↔  = Possible transcription start sites.

| 434 REPRESSOR GENE | | SEQUENCE AT SalI SITE | |
|---|---|---|---|
| PRESENT | ABSENT | | |
| pPS1 | pAD18 | GTCGA<u>ACAAGAAAGTTTGT</u>TCGAC | WILD-TYPE 434 $O_{R}1$ |
| pPS2 | pAD16 | GTCGA<u>ACAATATATATTGT</u>TCGAC | "WILD-TYPE" SYNTHETIC |
| pPS3 | pAD17 | GTCGA<u>TCAATATATATTGA</u>TCGAC | "MUTANT" SYNTHETIC |
| pAD15.2 | pAD14 | G.....................TCGAC | NO OPERATOR |

FIG. 15A

```
                    10              20              30              40
                    --              --              --              --
GGC CTT GCC CGC TCG TTC CCC TCG CCT CCC CGG TCG CGC TCC 50              60              70              80              90
       --              --              --              --              --
CGC TGC CGC CGT GGC GAT TCC TGC CCG GCG GCG CCG GGT TCA 100             110             120             130
       --              --              --              --
GGT CCA CGG CGG CGG CTG CGC GGG GCG GGA CCG ACT ATG GGA
                                                  Met Gly 140             150             160             170             180
       --              --              --              --              --
CGG ACG ACA GCA AGA TCT CCC CCG ACG AGG AAT TCC TTC GAG GCC
Arg Thr Thr Ala Arg Ser Pro Pro Thr Arg Asn Ser Phe Glu gly 190             200             210             220
       --              --              --              --
TGC GAC TAC AAC CAC TGG CTC ATC ACC ATG GAC TTC CCG GAC CCC
Cys Asp Tyr Asn His Trp Leu Ile Thr Met Asp Phe Pro Asp Pro
```

FIG. 15B

```
     230            240            250            260            270
      |              |              |              |              |
AAG CCG TCG CGC GAA GAG ATG ATC GAG ACA TAC CTC CAG ACT CTC
Lys Pro Ser Arg Glu Glu Met Ile Glu Thr Tyr Leu Gln Thr Leu 280            290            300            310
                     |              |              |              |
GCC AAG GTC GTC GGG AGT TAT GAG GAG GCC AAG AAG AGG ATG TAT
Ala Lys Val Val Gly Ser Tyr Glu Glu Ala Lys Lys Arg Met Tyr 320            330            340            350            360
      |              |              |              |              |
GCT TTT AGT ACG ACG ACT TAT GTT GGT TTT CAG GCT GTA ATG ACC
Ala Phe Ser Thr Thr Thr Tyr Val Gly Phe Gln Ala Val Met Thr 370            380            390            400
                     |              |              |              |
GAG GAA ATG TCA GAA AAA TTT CGC GGT TTG CCT GGA GTA GTT TTC
Glu Glu Met Ser Glu Lys Phe Arg Gly Leu Pro Gly Val Val Phe
```

FIG. 15C

```
        410             420             430             440             450
         |               |               |               |               |
ATT TTG CCT GAT TCA TAT CTA TAT CCA GAA ACA AAG GAG TAC GGA
Ile Leu Pro Asp Ser Tyr Leu Tyr Pro Glu Thr Lys Glu Try Gly 460             470             480             490
         |               |               |               |
GGA GAC AAA TAT GAC AAT GGT GTC ATC ACT CCA AGA CCA CCT
Gly Asp Lys Tyr Asp Asn Gly Val Ile Thr Pro Arg Pro Pro 500             510             520             530             540
         |               |               |               |               |
GTT CAT TAT AGC AGA CCA TCA AGA ACT GAC AGG AAC CGT AAC TAC
Val His Tyr Ser Arg Pro Ser Arg Thr Asp Arg Asn Arg Asn Tyr 550             560             570             580
         |               |               |               |
CGA GGA AAC TAC CAG GAT GGC CCT CCA CAG CAA GGA AAT TAC CAG
Arg Gly Asn Tyr Gln Asp Gly Pro Pro Gln Gln Gly Asn Tyr Gln 590             600             610             620             630
         |               |               |               |               |
AAC AAC CGT CCT CCA CCA CCA GAA GGT TAC CAG AAC AAC CCG CCG
Asn Asn Arg Pro Pro Pro Pro Glu Gly Tyr Gln Asn Asn Pro Pro
```

FIG. 15D

```
   640              650              660              670
    |                |                |                |
CAG CAA GGA AAC TAC CAG ACA TAC CGC TCG CAG CAA GAT GGA AGA
Gln Gln Gly Asn Tyr Gln Thr Tyr Arg Ser Gln Gln Asp Gly Arg 680              690              700              710              720
    |                |                |                |                |
GGC TAT GCC CCA CAG CAG AAT TAT GCA CAA GGT GGT CAG GAT GGT
Gly Tyr Ala Pro Gln Gln Asn Tyr Ala Gln Gly Gly Gln Asp Gly 730              740              750              760
    |                |                |                |
AGA GGT TTT GGA AGG AAT GAT TAC ACA GAC CGT TCA GGC TAC AAT
Arg Gly Phe Gly Arg Asn Asp Tyr Thr Asp Arg Ser Gly Tyr Asn 770              780              790              800              810
    |                |                |                |                |
GGA CCC ACT GAT TTT CGA AGT CAA ACT CAG TAC CAA GGG CAT GTA
Gly Pro Thr Asp Phe Arg Ser Gln Thr Gln Tyr Gln Gly His Val
```

FIG. 15E

```
                                                        850                              900
AAT CCA GCT GGG CAA GGT CAA GGT TAC AAC AAC CCC CAA GAG CGT
Asn Pro Ala Gly Gln Gly Gln Gly Tyr Asn Asn Pro Gln Glu Arg

890
ACG AAC TTC TCG CAA GGG CAG GGA GGT TTT AGG CCT GGT GGT
Thr Asn Phe Ser Gln Gly Gln Gly Gly Gly Phe Arg Pro Gly Gly 930                              990
CCT TCA GCA CCT GGG TCT TAT GGC CAA CCA TCA GCA CCT GGA TCT
Pro Ser Ala Pro Gly Ser Tyr Gly Gln Pro Ser Ala Pro Gly Ser 970                              980
TAT GGT CAA CCT GGT AAT ACA CTT GGT AAC TAT GGG CAG GTA CCT CCA
Tyr Gly Gln Pro Gly Asn Thr Leu Gly Asn Tyr Gly Gln Val Pro Pro 1010                 1020                  1030
TAT GGT CAA CCT GGT GGT AAC AGA GTT CCT GGT GTG AAT CCT AGT
Tyr Gly Gln Pro Gly Gly Asn Arg Val Pro Gly Val Asn Pro Ser

TCA GTG AAT CCT GGT GGT AAC AGA GTT CCT GGT GTG AAT CCT AGT
Ser Val Asn Pro Gly Gly Asn Arg Val Pro Gly Val Asn Pro Ser
```

FIG. 15F

```
      1040            1050            1060            1070            1080
       |               |               |               |               |
TAT GGT GGG GAT AGA CAG GGG GCT GGA CCA GCA TAT GGT GGA
Tyr Gly Gly Asp Arg Gln Gly Ala Gly Pro Ala Tyr Gly Gly 1090            1100            1110            1120
       |               |               |               |
GAT AAC TGG CAA AGA GGT TCT GGT CAG TAT CCT AGC CCA GGT GAA
Asp Asn Trp Gln Arg Gly Ser Gly Gln Tyr Pro Ser Pro Gly Glu 1130            1140            1150            1160            1170
       |               |               |               |               |
GGA CAA GGA AAC TGG CAG GGA AGG CAG TAA GAG CTG ACG TGT TCC
Gly Gln Gly Asn Trp Gln Gly Arg Gln 1180            1190            1200            1210
       |               |               |               |
ACT GAA GAC AAG AAT GGC ACT TGA GAT TTA GAA ATC TCC ATC TGT
```

FIG. 15G

```
       1220            1230           1240           1250            1260
        |               |              |              |               |
AAA ATA AAC GAC TGT GAT GCA TTA CTC TTT TTT TTC TTG CAT 1270            1280           1290           1300
        |               |              |              |
TTG AAC TCT AAA CTT ATG GGC ATG CGT TAT TAC CAA ACT ACG GAT 1310            1320           1330           1340            1350
        |               |              |              |               |
EGA AAT TCA TTT TAG TTT TTT GGG CCA AAT GTT GGC ATT TTT AAA

AAA
```

FIG. 16A

```
          10                  20                  30                  40
          |                   |                   |                   |
GCA GGG GGG GCA CAG CAA GCC AGC AGA GCA GAA AGC AGC CGC
Ala Gly Gly Gly Ala Gln Gln Ala Ser Arg Ala Glu Ser Ser Arg 50                  60                  70                  80                  90
          |                   |                   |                   |                   |
AGC CCC AGC CCC CAC AAA GAC GAA GGC AAC AAT GGC GCT AGA AGC
Ser Pro Ser Pro His Lys Asp Glu Gly Asn Asn Gly Ala Arg Ser 100                 110                 120                 130
          |                   |                   |                   |
AGC CAC GCC CCC CGC GCA CTC CTC GCG CGT GCC TCG TCC TGC TGG
Ser His Ala Pro Arg Ala Leu Leu Ala Arg Ala Ser Ser Cys Trp 140                 150                 160                 170                 180
          |                   |                   |                   |                   |
TCC TCG GCG GCA CCG GCC CGT CGT CGG TGC TCA GCG CGC CGG
Ser Ser Ala Ala Pro Ala Arg Arg Arg Cys Ser Ala Arg Arg
```

FIG. 16B

```
     190         200         210         220
      |           |           |           |
GGC GCA GGA CCG GCG GCA GTG CCT GCC GCA GCT GAA CGC CTC CTG
Gly Ala Gly Pro Ala Ala Val Pro Ala Ala Ala Glu Arg Leu Leu 230         240         250         260         270
      |           |           |           |           |
CGG TGC CGC GCG TAC CTG GTG CCG GCG CGC CGG ACC CCA GCG CGG
Arg Cys Arg Ala Tyr Leu Val Pro Ala Arg Arg Thr Pro Ala Arg 280         290         300         310
      |           |           |           |
ACT GCT GCA GCG CTG ACG CGC CGT GTG CAC GAG TGC GCC TGC AGC
Thr Ala Ala Ala Leu Thr Arg Arg Val His Glu Cys Ala Cys Ser 320         330         340         350         360
      |           |           |           |           |
ACC ATG GGC ATC ATC AAC AGC CTG CCC GGC CGG TGC CAC CTC GCC
Thr Met Gly Ile Ile Asn Ser Leu Pro Gly Arg Cys His Leu Ala
```

FIG. 16C

```
         370             380             390             400
          |               |               |               |
CAA GCC AAC TGC TCC GCT TGA AGC AGG GAC CTG GCA CGC GTG CTG
Gln Ala Asn Cys Ser Ala 410             420             430             440             450
          |               |               |               |               |
CAA TGG ATG GCA GGA GGG GAG AGG AAT AAG AAG TGT TTC CAT TTC 460             470             480             490
          |               |               |               |
ACA GTG AGA GCA GTC GAG CTC CAA CGT TGT CGT CGT CGT CTT 500             510             520             530             540
          |               |               |               |               |
CTT CTT TTG ATA TTC AGA CTC TGT CTT GCG GTC TAT ATC ATC AGC 550             560             570             580
          |               |               |               |
ATA ATA ATA AAA TAA GTA AAA CCA AAA AAA AAA AAA AA
```

FIG. 17A

```
         10          20          30          40
         |           |           |           |
ACA GCA GTA GCA AGA GGG ATA GAG CAA GGC CAC ACA CAC ACA CAC 50          60          70          80          90
         |           |           |           |           |
ACC ACT AGG CTA GGT TAG CCT TTT AAT CGT CGT CGA GAA GCA AGA 100         110         120         130
         |           |           |           |
AGG GCG CTG CAC CAA GCA GGC AAG CAA GAA GAG AGC CGA TCG ACC 140         150         160         170         180
         |           |           |           |           |
GAG AGC TAG CAC GCG AGG TCT TGC CAA GAT GAT GGT GGC
                        Met Ala Arg Ser Cys Gln Asp Asp Gly Gly 190         200         210         220
         |           |           |           |
GCA CGT CTG CTG GCC TTG CGC TGG CGT GTC GAC CGC CGA GGC AGG
Ala Arg Leu Leu Ala Leu Arg Trp Arg Val Asp Arg Arg Gly Arg
```

FIG. 17B

```
     230         240         250         260         270
      |           |           |           |           |
AAC ATC AAG ACC ACG ACG GAG AAG AAG GAC GCG GTG GTG
Asn Ile Lys Thr Thr Thr Glu Lys Lys Asp Ala Val Val 280         290         300         310
             |           |           |           |
CAG CCG CAG AGG TTC CGC CCT TCG ACC GCC TCG GCG CGG CGC GTC
Gln Pro Gln Arg Phe Arg Pro Ser Thr Ala Ser Ala Arg Arg Val 320         330         340         350         360
      |           |           |           |           |
CCC GGC GTT CGG CGG CCT CCC CGG CGG CAC GAT TCC TGG CAG CAG
Pro Gly Val Arg Arg Pro Pro Arg Arg His Asp Ser Trp Gln Gln 370         380         390         400
             |           |           |           |
CAT TCC CGG GTT CAG CAT GCC CGG CAG CAG CCT ACC CGG
His Ser Arg Val Gln His Ala Arg Gln Arg Gln Pro Thr Arg
```

FIG. 17C

```
      410             420             430             440             450
       |               |               |               |               |
GTT CAG CTT GCC CGG CAG CGG CAC GAT GCC CCT CTT CGG CGG CGG
Val Gln Leu Ala Arg Gln Arg His Asp Ala Pro Leu Arg Arg Arg 460             470             480             490
       |               |               |               |
CTC CCC GGG CTT CAG CGG CGG CGG CAT GCC CGG GTC GCC CAC
Leu Pro Gly Leu Gln Arg Leu Arg Arg His Ala Arg Val Ala His 500             510             520             530             540
       |               |               |               |               |
CGC CGG CTC CGT CCC CGA GCA CGC CAA CAA GCC CTG AAC GCC AAC
Arg Arg Leu Arg Pro Arg Ala Arg Gln Gln Ala Leu Asn Ala Asn 550             560             570             580
       |               |               |               |
AAG CGT GGT AGT AGA GGT GCT ACT GTT ACT GTA CGT CGT CGT
Lys Arg Gly Ser Arg Arg Gly Ala Thr Val Thr Val Arg Arg Arg 590             600             610             620             630
       |               |               |               |               |
CTT CAT GCA TGC GTG GTT CGT GGT TTC CCT AGC TCC ATA CGA GCA
Leu His Ala Cys Val Val Arg Gly Phe Pro Ser Ser Ile Arg Ala
```

FIG. 17D

```
                640         650         660         670
                 |           |           |           |
GTA GTT GGG CTT GCA CGT ACC GTA CGT CTA GCT AGC TAT ATA TAT
Val Val Gly Leu Ala Arg Thr Val Arg Leu Ala Ser Tyr Ile Tyr 680         690         700         710         720
        |           |           |           |           |
GCT TGT GTT CTA CTG CTT TTT AGT TTA ATT ACC TGC CTG CAT TGG
Ala Cys Val Leu Leu Leu Phe Ser Leu Ile Thr Cys Leu His Trp 730         740         750         760
        |           |           |           |
AGA GTT GGA TCT GTT TCA TTT GGT GGT GTT TGC TTT ACT ATT AGG
Arg Val Gly Ser Val Ser Phe Gly Gly Val Cys Phe Thr Ile Arg 770         780         790         800         810
        |           |           |           |           |
TCA GTA TCT GTT TGT GGA GAC TTG GTG TTT AAT TTA AGC CGT
Ser Val Ser Val Cys Gly Asp Leu Val Phe Asn Leu Phe Ser Arg
```

FIG. 17E

```
           820       830       840       850       860
            |         |         |         |         |
TTG TGA CTG GTT GTA GCT AGC GGT GGT GCG GTG GTG ATG TTC TTG
Leu 860       870       880       890       900
            |         |         |         |         |
AGG CAT GAA TAA TGC TAC ATG CAT GTG ATG TAT CCA TGT TTT GTG 910       920       930
            |         |         |
TGT GGT AAA CCT GTT GTT TGT ATA AGC TGT CCC
``` pTAK1  GGATCCCC G    GGT GGTCAGTCCCTT ATG
       BamHI
            Smal pTAK2  GGATCCCC GG   GTA GGTCAGTCCCTT ATG
            Smal pTAK3  GGATCCCC GGG  TAC GGTCAGTCCCTT ATG
            Smal

FIG. 25

```
                     KpnI
   1 UCGAAGUUGA GAGUUCGGUA CCCACAUCAG GCAACAGUGC CACUGUUGUC
  51 UUCAGGGCUG AUUCCUUUUG GUCUCUGCCC UCCGAGCCAA GAUGGUGAGU
 101 UCGACAACUU CCGAAGUGCA ACCCACCAUG GGGUCAAGA UCUUCUCAGC
 151 CGGCGUUUCU GCCUGCCUAG CAGACAUCAU CACCUUCCCG CUGGACACCG
 201 CCAAAGUCCG CCUUCAGAUC CAAGGUGAAG GCCAGGCUUC CAGUACUAUU
 251 AGGUAUAAAG GUGUCUUAGG GACCAUCACC ACCUGGCCA AGACAGAAGG
 301 AUUGCCGAAA CUGUACAGCG GUCUGCCUGC UGGCAUCCAG AGGCAAAUCA
 351 GCUUUGCUUC CCUCAGGAUU GGCCUCUACG AUACGGUCCA AGAGUACUUC
 401 UCUUCAGGGA GAGAAACGCC UGCCCUCUUG GGAAGCAAGA UCUCGGCUGG
 451 CUUGAUGACG GGUGGCGUGG CGGUAUUCAU UGGGCAGCCC ACAGAGGUGG
 501 UGAAGGUCAG AAUGCAAGCA CAAAGCCAUC UGCACGGGAU CAAACCCCGC
 551 UACACUGGGA CCUACAAUGC UUACAGAGUU AUAGCCACCA CAGAAAGCUU
 601 GUCAACACUG UGGAAAGGGA CGACUCCUAA UCUAAUGAGA AAUGCAUCA
 651 UCAACUGUAC AGAGCUGGUG ACAUAUGACC UCAUGAAGGG GGCCCUUGUG
 701 AACCACCACA UACGGCAGA UGACGUCCCC UGCCAUUUAC UGUCAGCUCU
 751 UGUCGCCGGG UUUUGCACCA CACUCCUGGC CUCUCCGGUG GAUGUGGUAA
 801 AAACGAGAUU CAUCAACUCU CUACCAGGAC AGUACCCAAG UGUACCGAGC
 851 UGGCAAUGA CCAUGUACAC CAAGGAAGGA CCGGCAGCCU UUUUCAAAGG
 901 GUUUGCGCCU UCUUUUCUGC GACUCGGAUC CUGGAACGUC AUCAUGGGUG
 951 UGUGCUUUGA ACAGCUGAAG AAAGAGCUGA UGAAGUCCCG GCAGACAGUG
1001 GACUGCACCA CAUAGGCGAC UUGGAGAAAG GGAUGCUAAA CACCAUGGGG
1051 CUCCUAUGCU GGGCUCCUAU GCUGGGAGAC CACGAAUAAA ACCAACCAAA
1101 GAAAUCAGAC G
```

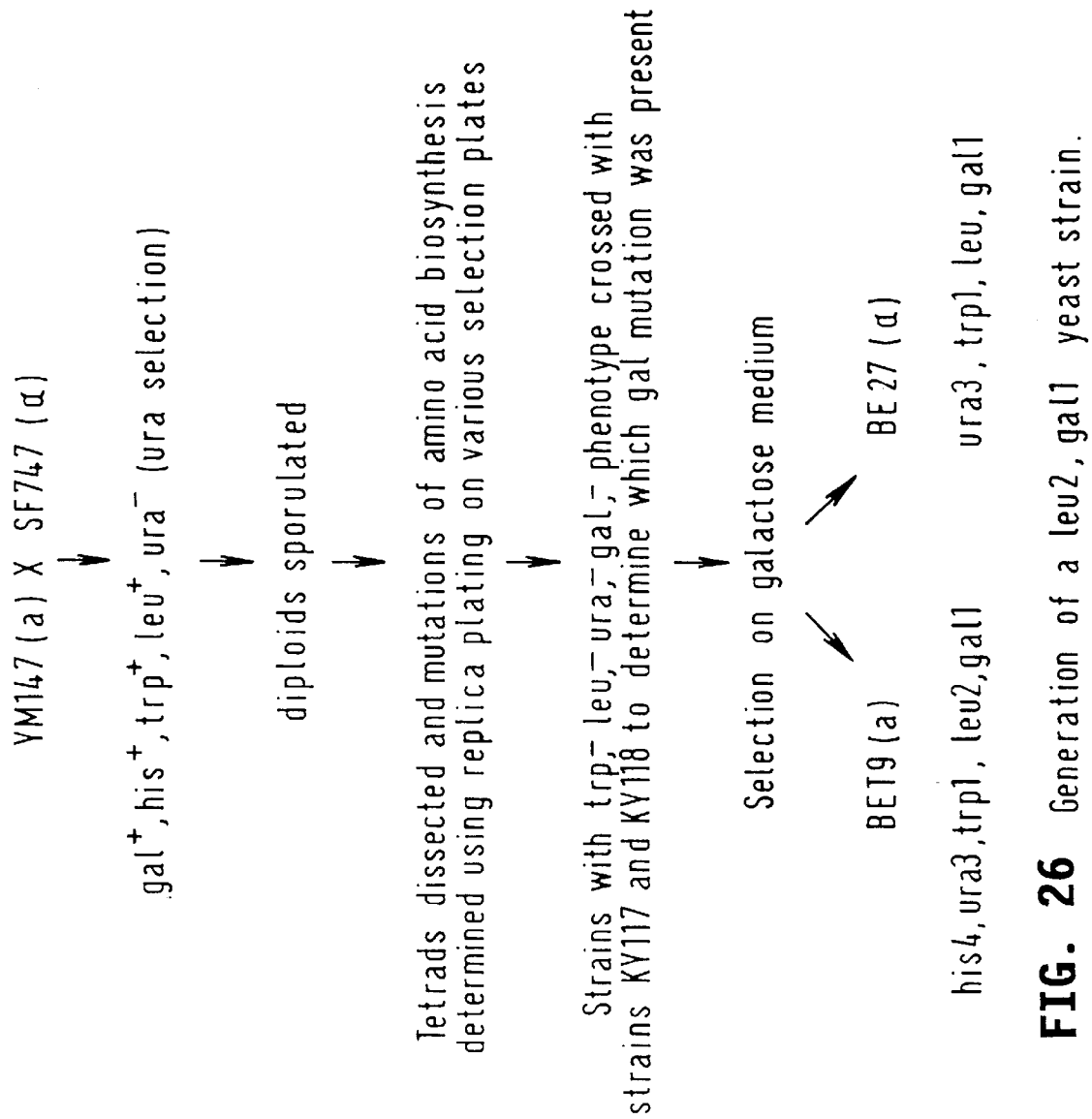
FIG. 26 Generation of a leu2, gal1 yeast strain.

FIG. 27

| | BE27 | BE27 PKV | BE27 UCP | BET9 | BET9 PKV | BET9 UCP |
|---|---|---|---|---|---|---|
| YPD<br>YPD+Gal | ★★★<br>★★★ | ★★★<br>★★★ | ★★★<br>★★★ | ★★★<br>★★★ | ★★★<br>★★★ | ★★★<br>★★★ |
| YPDG<br>YPDG+Gal | ★★★<br>★★★ | ★★★<br>★★★ | ★★★<br>★★★ | ★★★<br>★★★ | ★★★<br>★★★ | ★★★<br>★★★ |
| MMGlu<br>MMGlu+Gal | ★★★<br>★★★ | ★★★<br>★★★ | ★★★<br>★★★ | ★★★<br>★★★ | ★★★<br>★★★ | ★★★<br>★★★ |
| MMLac<br>MMLac+Gal | ★★★<br>★★★ | ★★★<br>★★★ | ★★★<br>★★★ | ★★★<br>★★★ | ★★★<br>★★★ | ★★★<br>★★★ |
| MMGly<br>MMGly+Gal | ★★★<br>★★★ | ★★★<br>★★★ | ★★★<br>★★★ | ★★★<br>★★★ | ★★★<br>★★★ | ★★★<br>★★★ |
| LacCas<br>LacCas+Gal | ★★★<br>★★★ | ★★★<br>★★★ | ★★★<br>★★★ | ★★★<br>★★★ | ★★★<br>★★★ | ★★★<br>★★★ |
| GlyCas<br>GlyCas+Gal | ★★★<br>★★★ | ★★★<br>★★★ | ★★<br>★★ | ★★★<br>★★★ | ★★★<br>★★★ | ★★★<br>★★ |
| 2%Lac<br>2%Lac+Gal | ★★★<br>★★ | ★★★<br>★★ | ★★★<br>★★★ | ★★★<br>★★★ | ★★★<br>★★★ | ★★★<br>★★★ |

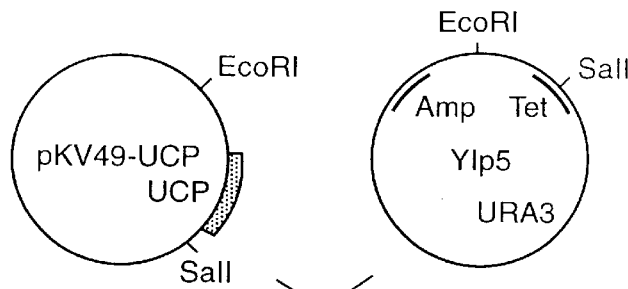
FIG. 31
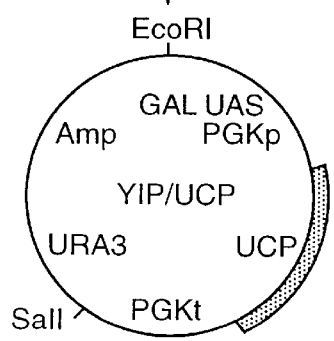
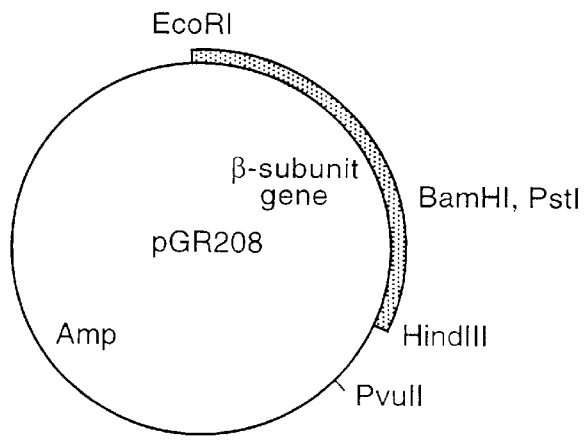
FIG. 32A
FIG. 32B
| | | |
|---|---|---|
| Oligo B1 | w.t. | ACGGTCAAATGAACGAACCTC |
| | mut. | ACGGTCAAATAAACGAACCTC |
| Oligo B2 | w.t. | AGGTGTCGGTAAGACTGTGTT |
| | mut. | AGGTGTCGGTCAGACTGTGTT |
FIG. 33A
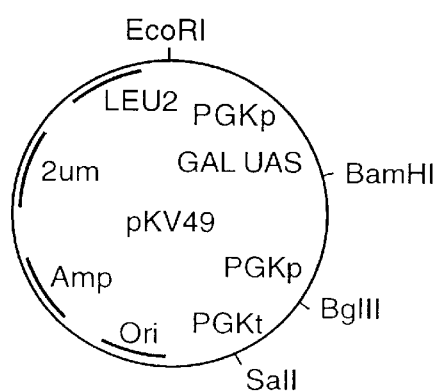
FIG. 33B
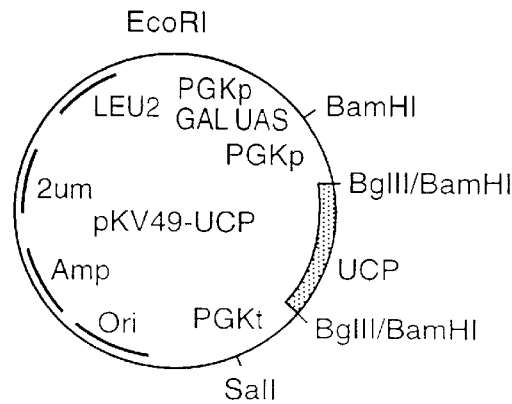

FIG. 34A
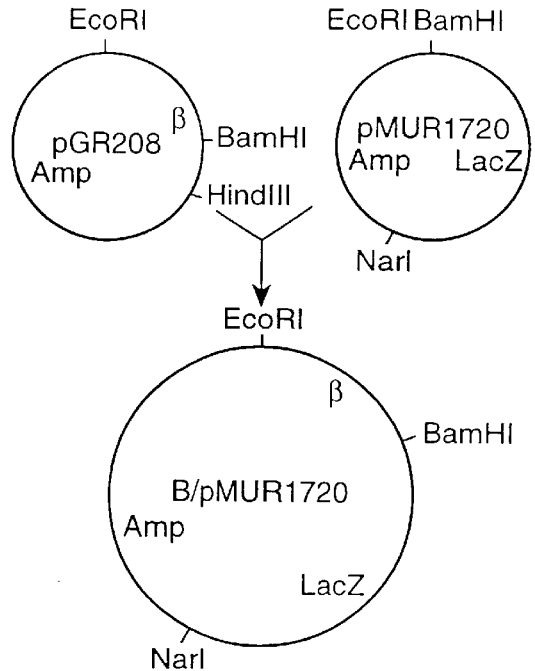
FIG. 34B
Fusion Junction
| ATT | TAC | CCT | GCA | GTG | GAT | CCC | GTC | GTT | TTA |
|-----|-----|-----|-----|-----|-----|-----|-----|-----|-----|
| Ile | Tyr | Pro | Ala | Val | Asp | Pro | Val | Val | Leu |
| 345 | 346 | 347 | 348 | 349 | 350 |     | 9   | 10  | 11  |
beto - subunit        Loc - Z
FIG. 35
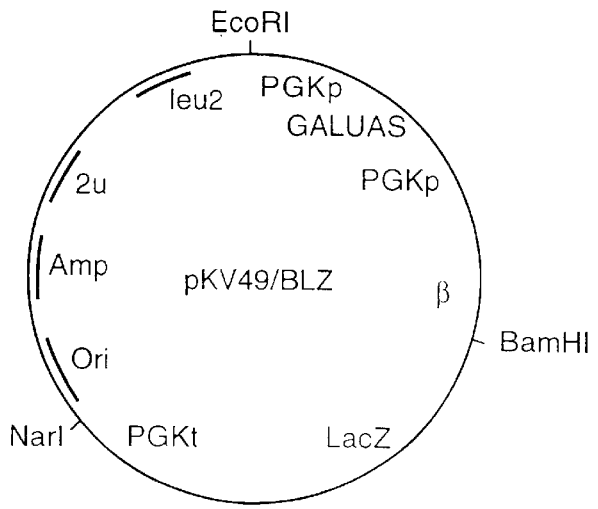

PLANT GENE CONSTRUCT COMPRISING MALE FLOWER SPECIFIC PROMOTERS

This is a continuation of application Ser. No. 08/165,544, filed on Dec. 13, 1993, which was abandoned upon the filing hereof which in turn is a continuation of application Ser. No. 07/824,883, filed Jan. 22,1992, now abandoned, which is a continuation of application Ser. No. 07/470,654, filed Jan. 26, 1990, now abandoned.

This invention relates to a method for the production of hybrid plants. More particularly, the invention relates to the molecular control of fertility in crop plants.

Agriculture uses many crop plants for the production of food for human consumption, for commercial processes yielding products for human consumption, for animal feedstuff production, for the development of industrial products and other purposes. The process invariably involves the planting by the farmer of seed which has been purchased from a seed producer. The product produced by the crop be it the whole plant, the seed or fruit of the plant, is harvested and is then used for the various food applications mentioned above. In addition to purchasing seed from a seed company, the farmer also may plant back some seed saved from a previous year's crop. This, however, is only economically useful for crops which are used as inbreds or outcrossed seed. It is not economically advantageous for hybrid crops, which are planted to realise the increase productivity achieved by heterosis. The major crops planted in the major agricultural regions are planted as hybrid crops, which guarantee the farmer considerable yield increases.

Production of hybrid seed by specialised seed companies is a costly and complicated process. The process involves the breeding and selection of inbred parental lines, which in suitable combinations give progeny which exhibit maximal adaptation to environmental conditions with realisation of maximal yield. For hybrid seed production inbreds are chosen as either male or female parent in a cross yielding F1 hybrid seed. AS most crops are hermaphroditic, the female parent in a cross has to be emasculated in order to avoid self-pollination during seed production. For open pollinating plants like maize a special planting regime is used in order to minimise self-pollinating of the female parent. This involves the separation of those plants to be used as males from the female parents. This allows easy separation of F1 hybrid seed at the end of the season.

Emasculation can be achieved either mechanically as it is used for maize, manually as it is used for tomato, or chemically as it is used for wheat or rice, and genetically using cytoplasmic male sterility (CMS) or genetic incompatibility as it is used for oil seed rape, sugar beet and others. These approaches vary in their complexity of agricultural practices or plant manipulation, but have in common, that they are costly to administer, complex to carry out and relatively inefficient depending on which system is used. This inefficiency arises from the fact that fertile plants need to be sterilised for seed production, which takes place in very large acreages depending on the crop. Therefore, large scale manipulation of females need to be carried out. Treatments also need to yield seed which is viable in the next generation which the farmer plants.

An object of the present invention is to obviate or mitigate the aforesaid disadvantages.

According to the present invention there is provided a plant gene construct which includes a disrupter protein gene capable of disrupting the biogenesis of viable pollen, and a gene control sequence which includes a promoter sequence inducible by external application of an exogenous chemical inducer to a plant containing the construct.

Preferably, the control sequence includes an operator controlling said disrupter protein gene and a repressor gene encoding a repressor protein adapted to bind said disrupter protein gene operator, said repressor protein gene being under control of said chemically inducible promoter.

Preferably also the construct includes a male flower specific operator sequence operatively linked to said disrupter protein gene, for restricting expression of the disrupter protein gene to male flower parts of a plant.

The invention also provides transformed plants and plant parts such as cells, protoplasts and seeds incorporating the construct of the invention.

In a preferred embodiment of the invention there is provided a recombinant DNA construct for insertion into the genome of a plant to impart restorable male sterility thereto, comprising:

(a) a first gene promoter sequence responsive to the presence or absence of an exogenous chemical inducer,
(b) a gene encoding a repressor protein under control of the said first promoter sequence;
(c) an operator sequence responsive to the said repressor protein;
(d) a second gene promoter sequence expressible only in male parts of a plant; and,
(e) a gene encoding a protein inhibitor of a plant characteristic essential to the production of viable pollen;

whereby the presence or absence of the exogenous chemical inducer enables selection of male fertility or sterility.

Further according to the invention there is provided a plant which is restorably male sterile, in which said plant contains, stably incorporated in its genome, the recombinant DNA construct defined above.

It is preferred that the said first promoter promotes expression of the repressor protein in response to stimulation by the exogenous chemical inducer whereby in the absence of the chemical inducer no repressor protein is expressed to interact with the operator thus permitting expression of the gene encoding the inhibitor of male fertility and in the presence of the chemical inducer repressor protein is expressed thereby preventing expression of the gene encoding the inhibitor of male fertility and restoring the plant to the fertile state. Thus the construct of the invention contains several operatively linked sequences (a) above will be referred to for convenience as "the chemical switch": (b) as "the repressor sequence" (c) as "the operator" (d) as "the MFS control" (i.e male flower specific control) and (e) as the disrupter gene. The essential elements of each of the sequences and their interaction will be described below with reference to the accompanying drawings.

This invention enables the production of inbreds which are rendered male sterile using various molecular techniques and approaches. These plants require a chemical switch system for the reversal of fertility (reversible male sterility; RMS). Both aspects of the system are inherited as Mendelian characters. This will be achieved through the insertion into the plant genome of the molecular elements required for the controlled function of RMS.

The invention can be used for any mono- or di- cotyledonous plant which the breeder or grower wants to produce as F1 hybrid seed and for which suitable transformation techniques are or become available, particularly maize, wheat, sunflower, oil seed rape, tomato and other vegetables, sugar beet and ornamental foliage and flowering plants. It has great advantages in reduction in crop management costs associated with F1 hybrid seed production, ease of purity control of hybrid seed, maintenance of RMS lines and populations, transfer of RMS between lines and populations etc.

In one specific application we shall describe the production of plants, particularly inbred plants, which are rendered sterile using molecular engineering approaches. These plants can be reversed to fertility using a chemical spray which leads to the restoration of fertility using a molecular control cascade. The method presented here consists of a number of individual components which are subject to separate patent applications which disclose wider applications of the components.

1. THE OVERALL PROCESS

FIG. 1 of the drawings is a block diagram of the DNA construct of the invention in the "male sterile" state. In the absence of the exogenous chemical inducer, the chemical switch is inactive and no repressor protein is expressed by the repressor sequence. In the absence of the repressor protein, the operator sequence permits expression of the disrupter protein in male specific tissue, expression being specifically directed to male parts of the plant by the presence of the MFS control sequence. The outcome being that the plant is male sterile, is unable to produce viable pollen and thus unable to self-pollinate. The practical utility of this effect is that if such plants, representing the female of an intended cross, are planted proximate the intended male parent of the cross, it will be pollinated by pollen from the intended male.

FIG. 2 shows the operation of the construct in the "male fertile" state. When the chemical inducer is brought into contact with the plant, the chemical switch is activated causing the repressor protein to be expressed. The repressor protein then binds the operator, inhibiting expression of the disrupter protein and restoring male fertility. The practical utility of this mode of operation of the construct is that it allows production of viable pollen and self- pollination of the plant containing the construct in order that the line may be perpetuated for future use.

2. THE CHEMICAL SWITCH

A large number of plant promoters are assumed to be induced using chemical signals. However, it has only been demonstrated in few examples that the specific chemicals switch on gene expression in the tissue required for this model. The gene of particular interest is the gene encoding the 27k subunit of glutathione-S-transferase II (GSTII). This gene is induced specifically upon treatment of plant tissues, particularly developing anthers using chemical safeners. One such safener is N,N-diallyl-2,2- dichloroacetamide, but there are related compounds which have improved mobility characteristics in plants tissues, combined with improved persistence for this application, efficacy and safety. These compounds have been described in the literature.

It is obvious that additional chemically induced promoters can be used in this scenario. Some of these may be of plant origin, others may be of fungal or yeast origin. It is implied in the present application that those promoters and chemical combinations suitable for the RMS procedure can be used in case of GSTII and safeners.

3. THE REPRESSOR AND OPERATOR SEQUENCES

In a first embodiment we propose to use the well-characterised interaction between bacterial operators with their repressors to control the expression of the 'killer' gene function. Bacterial repressors, particularly the lac repressor, or repressors used by 434, P22 and lambda bacteriophages can be used to control the expression in plant cells very effectively.

In a second embodiment it is possible to utilise 'pseudo-operators', operators which are similar but not identical to the normally used operators in a particular operator-repressor combination. We have demonstrated that using a suitable selection system mutant repressors can be generated which recognise pseudo-operators found in plants genes. We describe below the selection of mutant repressors recognising pseudo-operators which are found in plant genes.

Another approach for the down regulation of the 'killer' genes which can be considered is the use of antisense RNA. This has been demonstrated to work well for the regulation of polygalacturonase expressed during tomato fruit ripening and is described in the literature.

4. MALE FLOWER SPECIFIC EXPRESSION CASSETTE

As already mentioned, the expression of the 'killer' genes has to take place in male flower specific tissues (MFS). These can be tissues found in the developing anthers, in tissues associated with the developing anthers and pollen.

DNA promoter sequences which drive the expression of genes in MFS tissues can be achieved using established protocols for the identification of genes expressed in MFS tissues through differential screening of cDNA libraries cloned in various vector systems, the isolation of genes encoding these cDNAs from genomic libraries using bacteriophage lambda vectors, and the characterisation of their promoter sequences using DNA sequencing and analytical plant transformation experiments.

5. DISRUPTER GENE

Inhibition of pollen formation will be achieved by using novel 'killer' genes which, when expressed specifically in male flowers during pollen formation (for details see above), will lead to cell death of the anthers and associated tissues, pollen mother cells, pollen and associated tissues. This will lead to the abortion of pollen formation, and plants which are male sterile. The origin of the 'killer'genes can be from a variety of naturally occurring sources, eg human cells, yeast cells, plant cells, fungal cells, or they can be totally synthetic genes which may be composed of DNA sequences some of which are found in nature, some of which are not normally found in nature or a mixture of both. The 'killer' genes will have preferably an effect on mitochondrial metabolism, at it has been quite clearly demonstrated that ample energy supply is an absolute requirement for the production of fertile pollen. However, it is also envisaged that the 'killer' function can be effectively targeted to other essential biochemical functions such as DNA metabolism, protein synthesis, and other metabolic pathways. Two such DNA constructs consist of those sequences encoding the mammalian brown adipose tissue uncoupling protein or variants thereof, or a synthetic gene which consists of a mitochondrial targeting domain, and a lipophilic domain which allows insertion of the protein into the mitochondrial membrane.

6. PRODUCTION OF AN EXPRESSION MODULE CONSISTING OF MFS PROMOTER SEQUENCES AND 'KILLER' GENES

Production of an expression module which consists of the male flower specific gene control sequences (MFS control) and the 'killer' genes will be done using established molecular techniques. The expression of this module in elite inbreds will lead to the production of the 'killer' gene product only in male flower specific tissues. This will lead to the production of male sterile plants.

7. TRANSFORMATION

Transgenic plants are obtained by insertion of the constructs described into the genome of the plants. The specific transformation procedure employed for insertion of the gene constructs of this invention into the plant genome is not particularly germane to this invention. Numerous procedures are known from the literature such as agroinfection using *Agrobacterium tumefaciens* or its Ti plasmid, electroporation, microinjection of plant cells and protoplasts, microprojectile transformation and pollen tube transformation, to mention but a few. Reference may be made to the literature for full details of the known methods.

8. REVERSAL OF STERILITY

It is apparent, that plants which are made sterile using the above techniques and methods are not desirable per se. Therefore we proposed to use a cascade using molecular elements which will allow the reversal of the engineered sterility to fertility thus permitting maintenance of these plants and their use in F1 hybrid seed production. Design of the reversal mechanism The reversal mechanism proposed here consists of three separate elements:
a. a chemically switchable promoter
b. a bacterial operator sequence
c. a bacterial repressor gene which binds with high affinity the aforementioned operator.

These elements will act in the following way: when restoration of fertility is required (eg in the inbred maintenance plots), plants are sprayed with a chemical. This chemical induces through a chemically-inducible promoter the expression of a bacterial repressor molecule which will bind to operator DNA sequences in the MFS control sequences. This binding will lead to the inhibition of the 'killer' gene function, thus allowing normal pollen formation to take place.

9A. APPLICATION TO F1 HYBRID PRODUCTION

FIG. 1 outlines the molecular events which will take place when RMS is used in elite plants. Three genetic scenarios are available for the expression of the introduced traits, depending on whether they are destined to act as dominant or recessive genes and on whether expression is arranged to occur in the tissues of the parent sporophyte or gametophyte. These scenarios are summarised in Table I below.

TABLE I

PRODUCTION OF F1 HYBRIDS

| | RMS Genotype | | | |
|---|---|---|---|---|
| Genetic Status of Expression | Female (MS) Inbred | Male Inbred | F1 Hybrid | F1 fertile Pollen Load |
| Sporophytic dominant | RMS/+ | +/+ | RMS/+ or +/+ | 50% plants (+/+) are 100% fertile |
| Sporophytic recessive | rms/rms | +/+ | rms/+ | 100% plants are 100% fertile |
| Gametophytic | RMS or RMS | + or + | RMS + or + | 50% plants are 50% fertile |

Where, for example, the RMS components, particularly the "killer gene" functions are expressed as dominant gene(s), it is advisable to utilise RMS in a heterozygous state (RMS/+ in the above-mentioned "Sporophytic dominant" classification). It is implied in this instance that during F1 hybrid seed production, the resulting hybrids are either RMS/+ or +/+ in their genotype. This means that only 50% of the plants (+/+ ) will be able to contribute to pollen production in the F1 used for grain production. This will be sufficient for most crops, particularly in maize in which a large amount of pollen is produced.

Importantly, RMS can also be used in the production of other classes of hybrids such as three-way and four-way crosses. In the above-mentioned embodiment using the dominant sporophytic expression, use of the female genotype RMS/RMS in the first cross conveniently generates the genotype RMS/+ on crossing with a+/+ pollinator. The rms/+ genotype then constitutes the male sterile female parent for use in the second cross.(See Table II below).

TABLE II

PRODUCTION OF 3 AND 4 WAY CROSSES

| | RMS Genotype | | | | |
|---|---|---|---|---|---|
| Genetic Status of Expression | First Female | First Male | Second Female | Second Male** | 3 or 4 way Hybrid |
| Sporophytic Dominant | RMS/RMS | +/+ → | RMS/+ | +/+ | RMS/+ or +/+ |
| Sporophytic Recessive | rms/rms | ms/rms* → | rms/rms | +/+ | rms/+ |
| Gametophytic | RMS or RMS | RMS or RMS* → | RMS or RMS | + or + | RMS or + |

*In these embodiments the first pollinator is treated with the chemical switch to restore male fertility.
**The second pollinator may be an inbred (3 way) or or a hybrid (4 way)

9B. APPLICATIONS IN BREEDING PROGRAMMES

In addition to its broad utility in hybrid seed production, the RMS invention is also conveniently utilised in breeding programmes, for example, in enforcing outcrossing in synthetic populations from which new inbred lines are to be derived. Scenarios similar, but not limited to those shown in the above Table for the first cycle in production of three and four way crosses may be employed. Use of the chemical switch facilities subsequent rounds of selfing cycles to produce new and improved genotypes Molecular screening (RFLP analyses) using DNA sequences derived from the DNA sequences used to facilitate the RMS invention may be conveniently used as probes during inbreeding to ensure that progeny to be advanced have retained all elements of the RMS system. These strategies offer a convenient and efficient procedure to transfer the RMS trait to new germplasm.

The invention will now be described, by way of illustration by the following specific descriptions of various component gene modules which may be utilised. Reference will be made to the accompanying drawings.

BRIEF DESCRIPTION OF THE FIGURES

FIG. 10 shows the structure of vector p35SlacI.

FIGS. 12A and 12B show the nucleotide sequence of the maize CAB promoter;

FIGS. 15A to 15G show the nucleotide and deduced amino acid sequence of MFS cDNA clone pMS10;

FIGS. 16A to 16C show the nucleotide and deduced amino acid sequence of MFS cDNA clone pMS14;

FIGS. 17A to 17E show the nucleotide and deduced amino acid sequence of MFS CDNA clone pMS18;

FIG. 25 shows the mRNA sequence of mammalian uncoupling protein gene from plasmid pCGS110-UCP (shown in FIGS. 22A to 22B);

FIG. 26 is a flowchart representation of the generation of a leu2, gal1 yeast strain;

FIG. 27 is a table showing the effect of addition of galactose on the growth of BET9 and BET27 transformants;

FIG. 31 illustrates the construction of plasmid YIP/UCP from pKV49-UCP and YIp5;

FIGS. 32A and 32B are maps of plasmid pGR208 and the sequence of oligonucleotides used to mutate the β-subunit gene of $F_1$-ATPase;

FIGS. 33A to 33B show maps of plasmids pKV49 and pKV49-UCP;

FIGS. 34A to 34B show schematically the construction of a β-subunit/β-galactosidase fusion protein;

FIG. 35 is a plasmid map of pKV49/BLZ;

THE PLASMIDS

Figure 1:
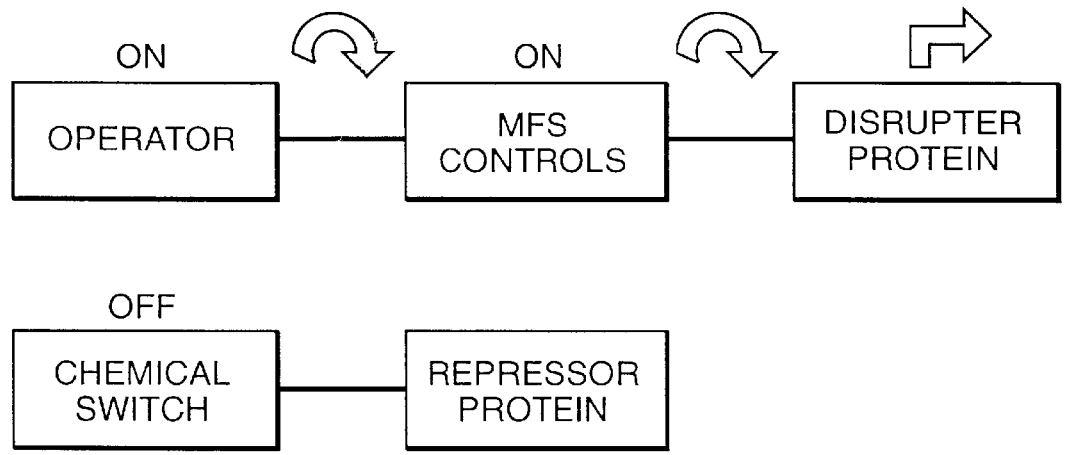
FIG. 1 is a block diagram of the gene construct of this invention with the plants in the male sterile state.
Figure 2:
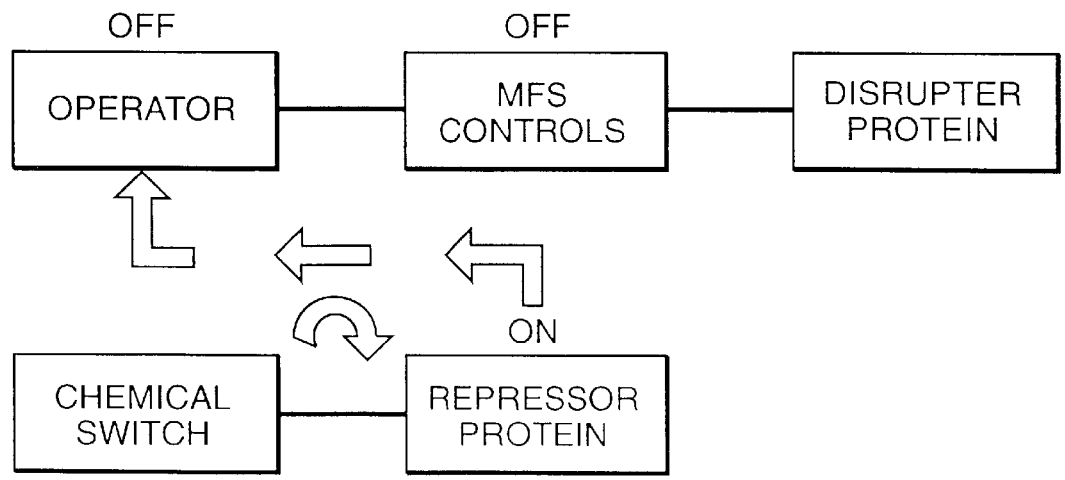
FIG. 2 is a block diagram of the gene construct of this invention with the plants in the male fertile state.

Various gene constructs are described in the following paragraphs and these have been deposited in the National Collection of Industrial & Marine Bacteria in Aberdeen, UK. The dates of Deposition and the Accession Numbers are summarised in Table III below.

TABLE III

| Plasmid | Host | Deposit Date | Accession No. |
|---|---|---|---|
| pGAL2 | E. coli DH5α | 06 Dec 1988 | NCIB 40087 |
| p35SlacI | E. coli TG-2 | 12 Dec 1988 | NCIB 40092 |
| pPS1 | E. coli DH5α | 21 Dec 1988 | NCIB 40097 |
| pAD18 | E. coli DH5α | 21 Dec 1988 | NCIB 40096 |
| pMS10 | E. coli RR1 | 09 Jan 1989 | NCIB 40098 |
| pMS14 | E. coli DH5α | 09 Jan 1989 | NCIB 40099 |
| pMS18 | E. coli RR1 | 09 Jan 1989 | NCIB 40100 |

I. THE CHEMICAL SWITCH

This module is exemplified by a chemically inducible gene promoter sequence isolated from a 27 kd subunit of the maize glutathione-S-transferase (GST II) gene.

In practice the chemically inducible promoter of the invention will be inserted as a promoter sequence in a recombinant gene construct destined for use in a plant. The construct will then be inserted into the plant by transformation. Expression of protein encoding genes in the construct, being under control of the chemically switchable promoter of the invention, may be controlled by the application of a chemical inducer to the plant.

Examples of effective promoter/inducer combinations are the promoter is the GST II promoter aforesaid and the inducer is N,N-diallyl-2,2- dichloroacetamide (common name: dichloramid) or benzyl-2-chloro-4-(trifluoromethyl)-5-thiazole- carboxylate (common name: flurazole)

Chemical inducers which are potential inducers of the GSTII 27 kd subunit expression include compounds such as:
1. benzyl-2-chloro-4-(trifluoromethyl)-5-thiazole-carboxylate;
2. naphthalene-1,8-dicarboxylic anhydride;
3. 2-dichloromethyl-2-methyl-1,3-dioxolane;
4. 1-(dichloroacetyl)-hexahydro-3,3,8a-trimethyl-pyrrole (1,2-a)-pyrimidin-6(2H)-one;
5. 2,2,5-trimethyl-N-dichloroacetyloxazolidine;
6. 1,3-dioxolan-2-ylmethoxyimono(phenyl)benzene acetonitrile;
7. 4,6-dichloro-2-phenyl-pyrimidine;
8. 2,2-dichloro-[N-allyl-N(1,3-dioxalano-2-methy)] acetamide;
9. 1-(cyanomethoxyimino)benzacetonitrile;
10. 4'-chloro-2,2,2-trifluoroacetophenone-O-1,3-dioxolan-2-yl methyloxime;
11. 2,2-dichloro-1-(3,4-dihydro-3-methyl-2H-1,4-benzoxazin-4-yl) ethanone;
12. 3-dichloroacetyl-2,2-dimethyloxazolidine;
13. 4-methoxy-3,3-dimethylbenzophenone;
14. 1-cyclohexyl-4,4-dimethyl-2-(1H-1,2,4-triazol-1-yl) pent-1-en-3-ol;
15. 2,2-dichloro-N-(3-methyl-4-thiazolin-2-ylidene) acetamide;
16. O,O-diethyl-O-phenyl phosphorothioate;

17. 2,2-spirocyclohexyl-N-dichloroacetyl oxazolidine;
18. N-benzyl-N-ethyl-dichloroacetamide;
19. 3-chloroacetyl-4,4-cyclohexane-spiro-2,2-dimethyl-1,3-oxazolidine; and,
20. spirooxazolidine acetamide.

Glutathione-S-transferases (GST) are a family of enzymes which catalyse the conjugation of glutathione via the sulphydryl group to a large range of hydrophobic, electrophilic compounds. The conjugation results in detoxification of these compounds and in insects and mammals, removal from tissue.

GST enzymes have been identified in a range of crop plants including maize, wheat, sorghum and peas. GST's comprise from 1 to 2% of the total soluble protein in etiolated maize seedlings.

The major isoform of GST can be distinguished in maize tissue. GST I is constitutively expressed and is capable of conjugating glutathione with the pre-emergent herbicides alachlor and atrazine. Treatment of maize tissues with chemical safeners (for example, N,N-diallyl-2,2-dichloroacetamide) raises the activity of GST I which participates in the detoxification of the pre-emergent herbicides.

Safener Treatment of Corn Tissue

Figure 3A:
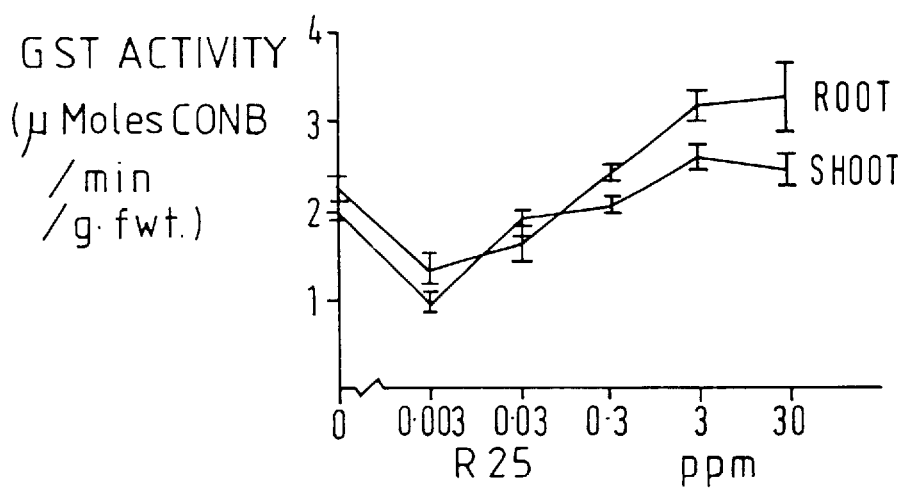
FIGS. 3A and 3B show the results for total GST activity in roots and shoots obtained 23 and 44 hours after treatment with R25 as described below.
Figure 3B:
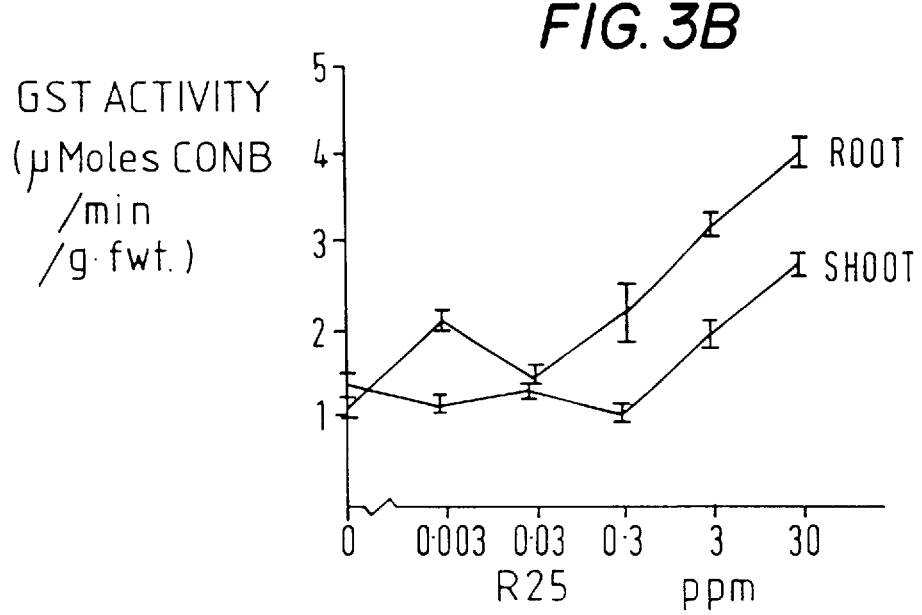
Figure 4:
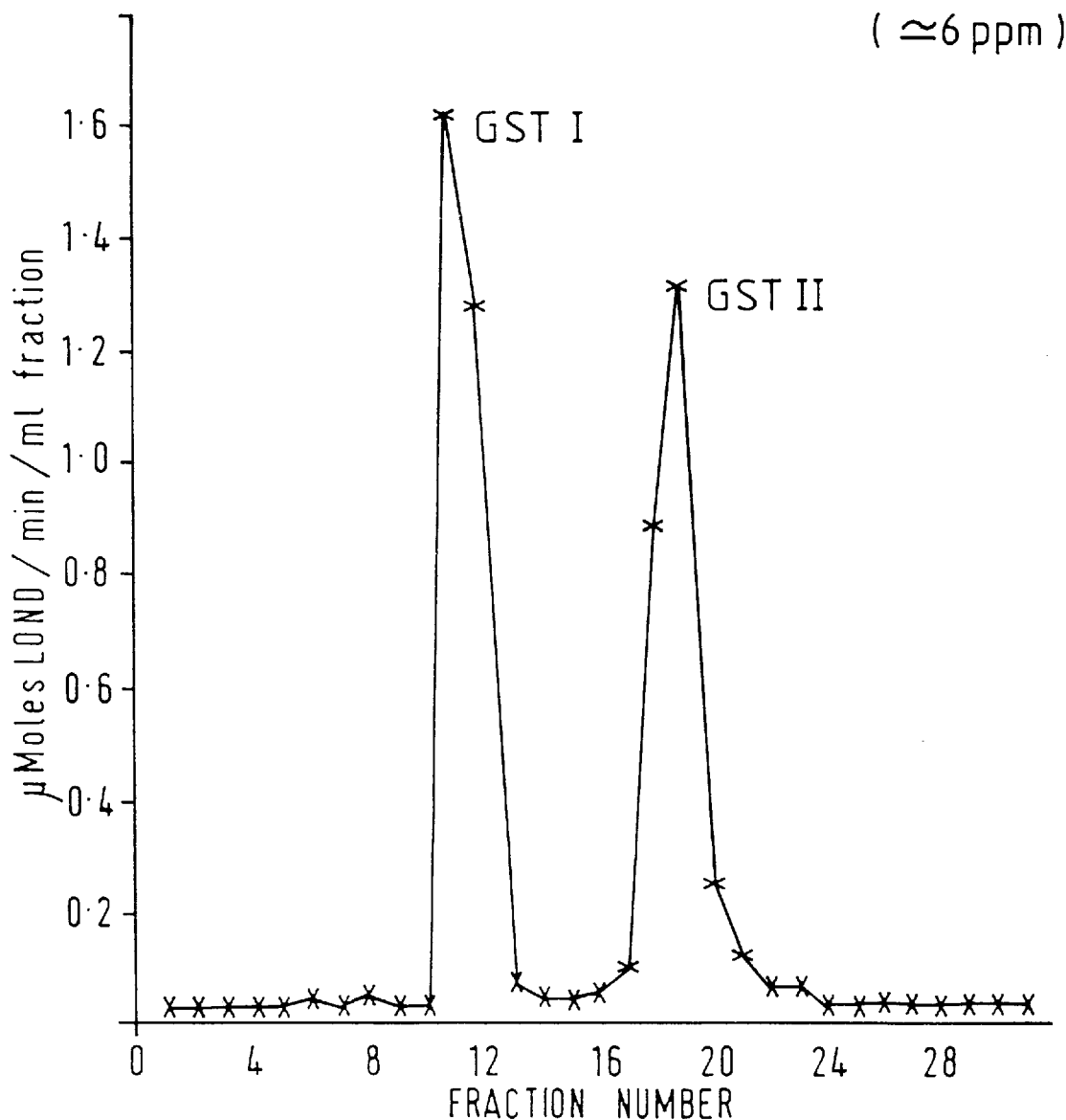
FIG. 4 shows the chromatographic separation of the isozymes GST I and GST II.

For treatment of young maize seedlings, seeds were germinated on moist filter paper. After germination and growth (up to one week) the safener N,N-diallyl-2,2- dichloroacetamide (hereinafter referred to as R25) was added to the water in the filter paper to give a range of concentrations (0.003 to 30 ppm) and the seedlings grown for a further 23 to 44 hours before harvesting of root and shoot tissue. FIGS. 3A and 3B show the results for total GST activity in roots and shoots obtained 23 and 44 hours after treatment as described and FIG. 4 shows the separation of the isozymes GST I and GST II.

Figure 5:
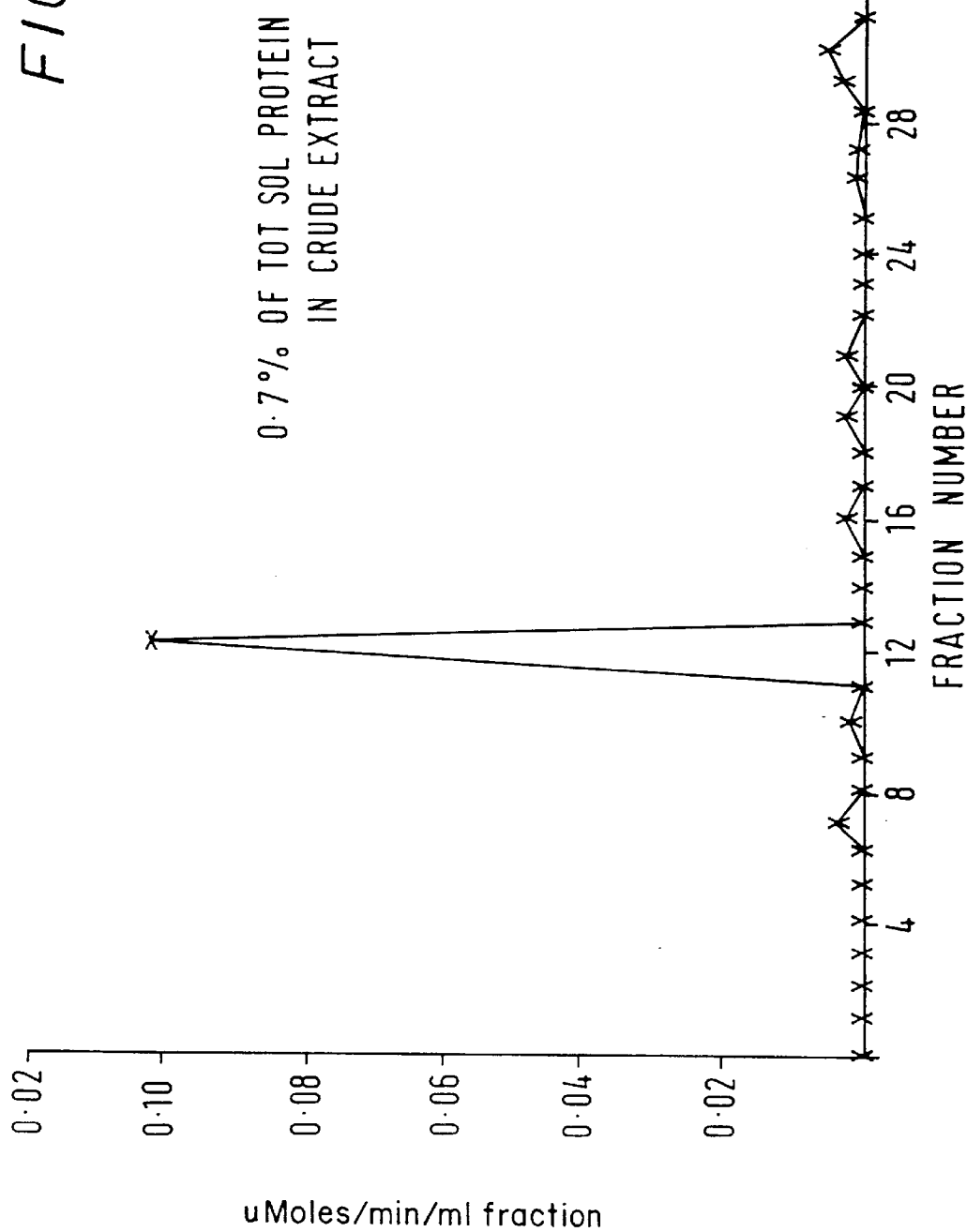
FIG. 5 shows GST I activity present in untreated anther tissue.
Figure 6:
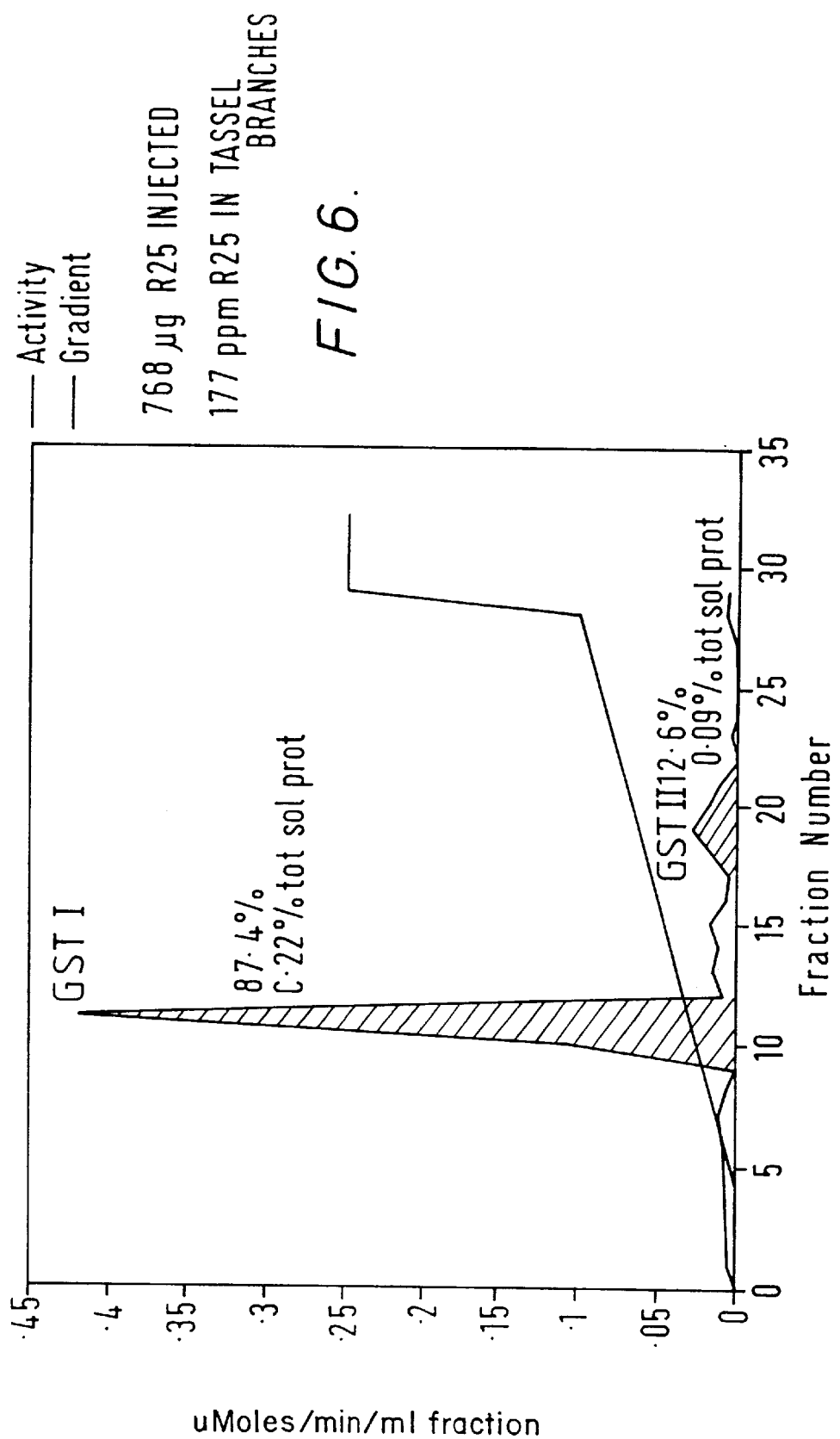
FIG. 6 shows the stimulation of GST II activity after treatment with R25 as described below.

For treatment of maize tassel and anther tissue, a solution of 800 μg of R25 was injected into the node directly below the developing tassel. Uptake then continued for a further 48 to 72 hours. FIG. 5 shows that only GST I activity was present in untreated anther tissue and FIG. 6 shows the stimulation of GST II activity after treatment as described.

Figure 7:
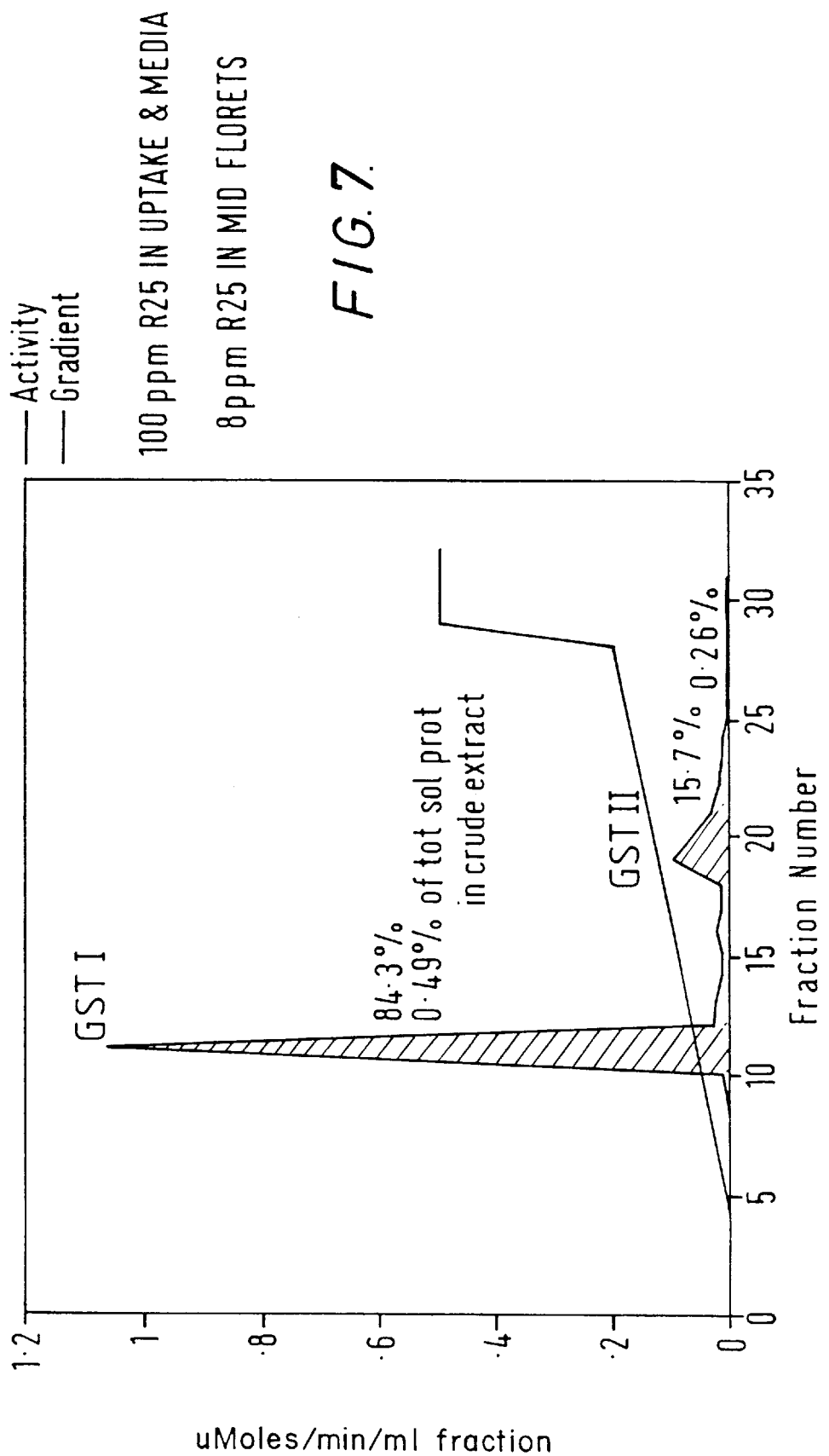
FIG. 7 shows the results using a stem reservoir technique.

Alternatively a 100 ppm solution of R25 was supplied from a glass reservoir attached to the exposed stem immediately below the developing tassel. FIG. 7 shows the results using a stem reservoir technique.

Figure 8:
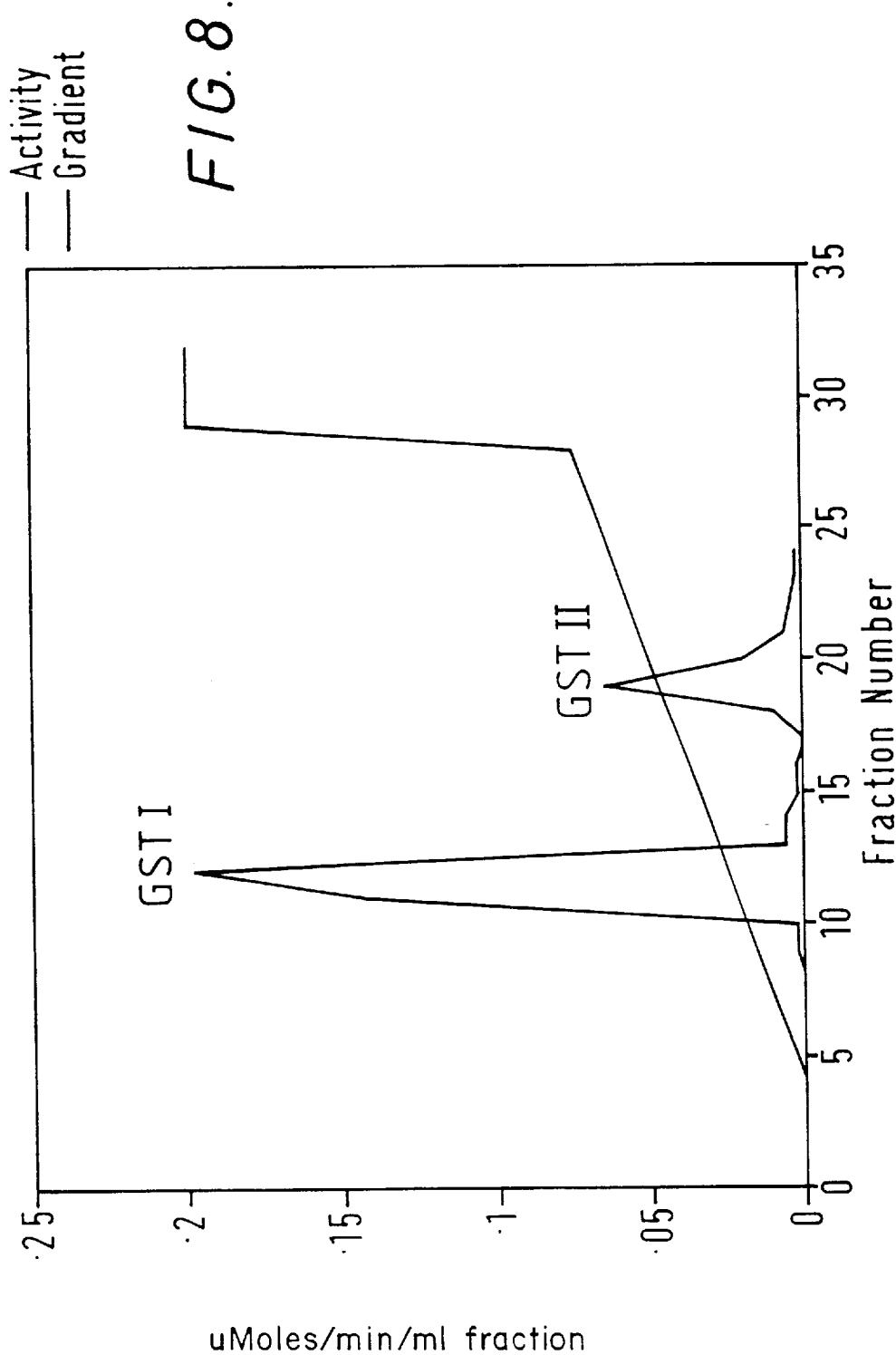
FIG. 8 shows the results with the application by spray.

Additionally, R25 was applied as a 100 ppm spray directly on to the exposed developing tassel. FIG. 8 shows the results with the application by spray.

Both GST proteins have a native molecular weight of approximately 50 kd. As in mammals, maize GST's are dimeric; GST I has apparently identical subunits of 29 kd, whereas GST II is a heterodimer of a 29 kd subunit similar to that found in GST I and a novel 27 kd subunit which is only present in tissue treated with safener except in seedling root where it is constitutively expressed, but still can be induced by safener treatment.

A cDNA and a gene corresponding to the 29 kd subunit of GST I have been cloned previously and sequenced. In addition, a cDNA corresponding to a 26 kd subunit of a third, minor component of GST activity in maize seedlings (GST III) has been previously cloned and sequenced.

Enzyme Assay

Enzyme activity was measured spectrophotometrically at 340 nm using 1-chloro-2,4-dinitrobenzene (CDNB) as a substrate. The reaction buffer contained 0.1M EDTA, 0.001M CDNB and 0.0025M glutathione.

Preparation of Extracts and Enzyme Purification

Tissue was homogenised in 0.05M Tris.HCl, pH 7.8; 0.001M EDTA; 0.001M DTT; and 7.5% polyvinylpyrrolidone in a pestle and mortar, at 4° C., and centrifuged at 30,000g to obtain a crude extract.

Separation of the GST isoforms from the crude extract was achieved as follows: the crude extract was applied to a DEAE Sepharose column and washed with 0.01M Tris.HCl, pH 7.8 ; 0.001M EDTA; and 0.001M DTT. The bound GST was eluted with 0.3M potassium chloride. Fractions containing GST activity were combined and desalted using PD10 gel filtration columns. Separation of the GST I and GST II isoforms was achieved by FPLC on a mono-Q column and a zero to 0.4M potassium chloride concentration gradient.

Pure samples of GST I and GST II were obtained by applying desalted fractions of GST I and GST II from the FPLC to a glutathione-S-sepharose affinity column equilibrated with 0.05M phosphate buffer at pH 7.3. After washing with buffer, bound GST was eluted with 0.005M glutathione.

SDS-PAGE (17.5%, 30:0.174 acrylamide: bisacrylamide) of GST I or GST II was achived by concentrating pure GST samples using Amicon Centricon 10 Microconcentrations (Trade Mark), denaturing samples in mercaptoethanol containing Laemmli buffer, and staining the gels with Coomassie Blue.

Generation of Antibodies to the Enzyme

Sufficient protein to enable the immunisation of rabbits is obtained by pooling the isolated enzyme subunit isolated as described above from a number of separate experiments. The 27 kD GST II polypeptide is subsequently purified to apparent homogeneity by electroelution from polyacrylamide gel slices. Antisera are prepared against the 27 kd polypeptide. The immunisation of rabbits is carried out essentially according to Mayer and Walker (1978).

N-terminal sequence analysis

The amino terminal sequence of the intact 27 kd subunit of GST II or partial proteolytic cleavage products was determined by sequential Edman degradation and subsequent amino acid analysis by HPLC.

Time Course

Figure 9:
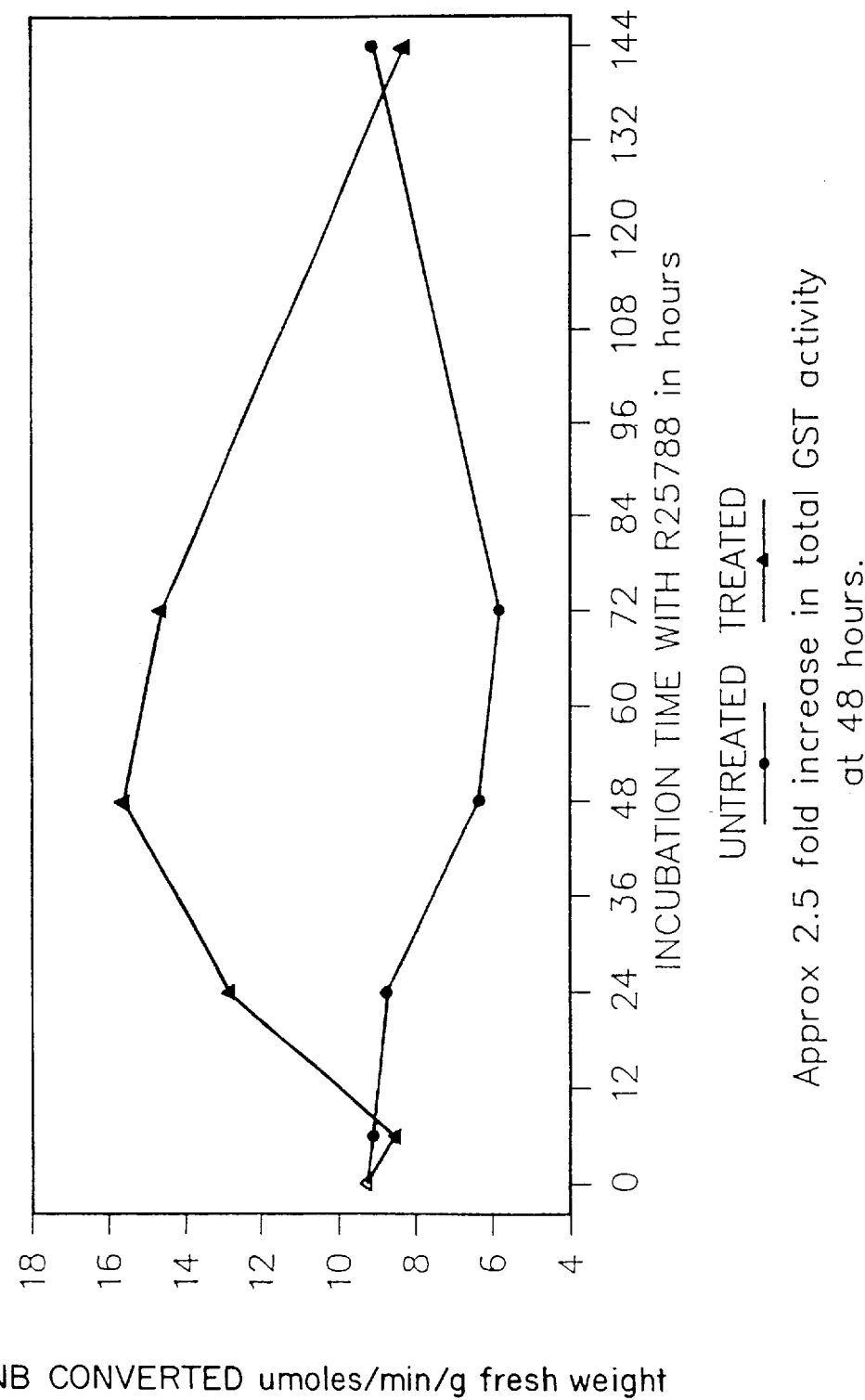
FIG. 9 is a time course graph generated in the manner described below.

A time course experiment was carried out to examine the expression of GST's after safener treatment. A 30 ppm solution of R25 was applied to three-day old seedling roots and tissue harvested after various time intervals following safener treatment. Samples were tested for GST activity using the enzyme assay described above. The results of this experiment are presented graphically in FIG. 9.

Synthesis of cDNA Libraries

The time course experiments revealed a peak of GST expression at 48 hours after treatement with safener. Therefore, two cDNA libraries were constructed from RNA extracted from tissue at 24 and 48 hours after safener treatment. To ensure that the induction procedure had been successful, a one gram sample of 24 hour induced tissue was taken and assayed for GST II. This experiment revealed that the tissue used to construct the cDNA library had indeed been successfuly induced as GST II accounted for 45.5% of the total GST activity.

Double-stranded cDNA was prepared from oligo dT-cellulose-purified RNA by a method employing RNaseH and E. coli DNA polymerase I in the synthesis of the second strand, without prior purification of single-stranded cDNA (Gubler and Hoffman,1983).

Screening cDNA libraries with antisera to GST I and GST II

In order to identify a cDNA clone encoding maize tassel GST enzyme, bacteriophage from the amplified cDNA library are screened with anti-maize GST enzyme serum. The clones producing the strongest signals are re-screened.

Screening cDNA libraries using oligo probes

Mixtures of synthetic oligonucleotides based on the amino acid sequence determined above were prepared by phosphoramidite chemical synthesis. The 5' ends of the oligonucleotides were labelled using polynucleotide kinase as described in the literature.

Approximately 40,000 phages containing cDNA were amplified on plates and transferred to nitrocellulose. The filters were hybridised to oligonucleotide probes at temperatures of from 2 to 5° C. below the melting temperature calculated for the lowest melting point probe in the mixture. Hybridising plaques were selected and rescreened through two or more rounds exactly as described above but at lower densities Isolation of cDNA Gene sequences by the PCR method cDNA or DNA sequences are isolated from the libraries described using oligo primers based on the amino acid sequence obtained from partial proteolytic cleavage or in the case of genomic DNA, primers based on cDNA sequence determined previously.

Characterisation and sequence analysis of GST cDNA clones

The isolated cDNA is characterised and subjected to sequencing by one or more of the standard available techniques.

Isolation of genomic sequences

An existing genomic library of fragments of total maize DNA cloned into XEMBL3 is used to isolate clones that hybridise to the cDNA clones isolated as described above.

Alternatively, the PCR method described above may be used to selectively amplify and clone gen fragments. GSTII genes and ther promoter sequences can then be isolated, and characterised using established techniques. It can be demonstrated that the GSTII promoter sequences mediate safener-induced gene activity by fusing them to marker genes like GUS and CAT, and testing then in transgenic plants.

II. The REPRESSOR AND OPERATION SEQUENCES

This module regulates plant gene expression. More particularly, the module regulates plant gene expression by the use of repressor molecules of bacterial or lower eukaryotic origin.

Traditionally, the improvement of crop plant species involves the introduction of desired traits by genetic crosses. However, although these breeding techniques are highly successful, they provide no means of controlling the expression of the newly acquired traits. Recent advances in technology are now allowing the genes responsible for determining plant structure and the productivity and quality of the crop to be identified and isolated. A major aim in the field of improvement is therefore to be able to manipulate complex developmental processes genetically in order to improve crop performance. Essential to this objective is the determination of strategies which allow the expression of specific plant genes to be regulated at will.

The ability to control the expression of traits according to circumstances has many important applications, such as control of insect resistance genes, determination of plant height and timing of flowering and the control of plant fertility. Additionally, the ability to switch genes on or off at will, without disturbing plant physiology or environment, would be an invaluable tool in the study of plant genetics per se.

Currently, the production of seed for hybrid crops such as maize involves the laborious and expensive process of hand or mechanical emasculation of the parent plants in order to prevent self-pollination. Such emasculation can, however, be controlled genetically by making use of a trait known as cytoplasmic male sterility (CMS) which has been observed in a wide variety of crop species. CMS interferes with male gametogenesis, resulting in the inhibition of pollen formation, but does not normally affect female fertility. Consequently, "male-sterile" plants are able to set seed, such seed resulting only from cross-pollination. The ability to control the expression of these genes would allow male gametogenesis to be inhibited in the production of hybrid crop seeds without the need for expensive emasculation processes, while still allowing genetic improvement of the male parent by conventional breeding programmes.

Control of gene expression in both prokaryotes and eukaryotes relies primarily on the interaction of regulatory proteins with specific DNA sequences. Depending on the nature of these interactions, transcription from the cognate promoters may either be repressed or activated. Indeed, in some cases the same protein may either reduce or enhance transcription according to the nature of the contacts made. Furthermore, the ability of some regulatory proteins to bind their target sequences is modulated by the binding of ligands or by specific proteolytic cleavage. Such mechanisms may be exploited in order to include inducibility amongst strategies for plant gene regulation.

The best characterised regulatory systems are those of bacteria in which the interactions between the DNA-binding proteins (repressors) and the target DNA sequences (operators) are understood in great detail. A comparison of the best understood systems, including repressor and cro proteins of bacteriophage λ and 434, the LacI repressor and the catabolite gene-activating protein (CAP), reveals several factors in common. These regulatory proteins bind as dimers or tetramers to short operators that exhibit a high degree of dyad symmetry. In most cases the domain responsible for DNA-recognition, which is separate from that concerned with oligomerisation of the monomers, contains a conserved helix-turn-helix structure. A specific helix within this structure in each monomer, the recognition helix, is aligned with the major groove of the DNA and only if specific contacts are formed between the amino acids of this recognition helix and the bases of the adjacent DNA can a functional repressor/operator complex be formed. Such interactions are highly specific, and the high-affinity complexes are formed with extremely rapid kinetics.

The knowledge of mechanisms by which gene expression is regulated in eukaryotes is much less detailed. In yeast and mammalian cells a large number of binding sites for putative regulatory proteins have been identified in promoter sequences, and in some cases the proteins responsible have also been isolated. However, only in a few instances are the molecular details known of the protein-DNA interactions and the mechanism by which transcription is regulated.

In plants, regulation of gene expression is understood at only a rudimentary level. Several regulatory elements have been identified in promoter sequences, and some regulatory proteins examined at a preliminary level. However, such proteins have yet to be isolated and the details of the mechanisms involved elucidated.

Eukaryotic regulatory systems appear to exhibit a greater diversity of structure and a higher degree of complexity than their prokaryotic counterparts. For instance, control of transcription from eukaryotic promoters is thought to involve the interaction of many proteins (perhaps in the order of tens) with the regulatory DNA. Furthermore, at least three different protein structures (the helix-turn-helix, the zinc-finger and the leucine zipper) have been implicated in the specificity of DNA-binding by various eukaryotic regulatory factors.

DNA-binding proteins constitute a class of proteins characterised by their ability to bind to DNA of genes to give the effect of either repressing or activating the gene to which they bind. Unless the context otherwise requires, such DNA-binding proteins will hereinafter be referred to for convenience simply as "repressors".

This module, then, is a recombinant plant gene comprising a repressor gene of bacterial origin and a promoter which operates in plants for driving expression of the repressor gene, said gene encoding a repressor protein capable of interaction with an operator sequence associated with a selected target plant gene so that on expression of the repressor protein expression of the target plant gene is inhibited.

A vector, designated p35SlacI, containing the said DNA, which has been deposited in an *E.coli*, strain TG-2, host with the National Collection of Industrial and Marine Bacteria Limited, Aberdeen, United Kingdom, on 12th Dec. 1988, under the Accession Number NCIB 40092.

A suitable plant transformation vector comprises *Agrobacterium tumefaciens*, harbouring the plasmid aforesaid.

In a specific embodiment of this module a bacterial lacI operator system is utilised to regulate gene expression. Lac repression can be relieved by iso-propyl thiogalactoside (IPTG) and other sugar analogues.

Specific Examples relating to this module will now be given.

EXAMPLE (1) Construction of plants expressing the lac repressor

Vectors were constructed which express the lacI gene from either the constitutive CaMV 35S promoter found in vector pJR1 or from the green tissue- specific promoter, the maize CAB promoter. However, the bacterial repressor can be expressed from any plant promoter expressed in other parts of the plant, thus allowing control of plant gene expression in any specific part of the plant.

(1.1) Modification and insertion of the lacI repressor gene into pJR1

The lac repressor (lacI$^Q$) is available on plasmid PMJR 156. In order to express this gene in plants, the translation initiation codon (GTG) had to be changed into ATG. In addition it was opportune to create a suitable restriction enzyme cleavage site for cloning of this gene into a plant expression vector. At the 3' end of the lacI there are suitable restriction sites (HindIII and PstI) for insertion into plant expression vectors. In order to create suitable restriction sites at the 5' end, the following experiments had to be performed:

(a) A Cfr 10 restriction site is located at position 134. pMJR was cut with Cfr 10 and a synthetic DNA fragment which reconstitutes the N-terminus of the lacI gene, the altered translational start codon ATG, a plant consensus sequence for efficient translational initiation and a BamHI restriction site were inserted into pJR1. The sequence of this synthetic fragment was: BamHI consensus GATCC AACAATGGCT AAACCAGTAACGTTATACGAT-GTCGCAGAGTAT G G TTGTTACCGA TTTGGTCAT-TGCAATATGCTACAGCGTCTCATA CGGCC Cfr 10 pJR1 was cut with BamHI and PstI. The synthetic fragment described above, and the Cfr10 to PstI fragment containing the lacI gene were ligated together with the cut vector pJR1 under standard conditions. The ligation mix was transformed into *E. coli* TG-2. Recombinants were selected on kanamycin-containing plates. They were characterised by DNA sequence analysis. The construct was designated p35SlacI.

(b) The PCR (Polymerase Chain Reaction) as described by Saiki et.al., Science, 239, 487–491) was utilised to introduce the changes at the 5' end of the lacI gene while keeping the sequence at the 3' end. Two oligonucleotides were hybridised to PMJR 156. The sequence of the oligonucleotides were:

(i) from the 5' end of the gene
                       BamHI     consensus
GAGAGTCAATTCAGGGT GGATCC AACAATGGCT AAACCAGTAACGTTATACG (ii) from the 3' end of the gene
CGTTGTAAAACGACGGCCAGTGCC The PCR reaction was carried out under the prescribed conditions. The product was cut with BamHI (at the newly introduced site) and PstI. The resulting fragment was cloned into pJR1 cut with BamHI and PstI. Recombinants were identified by hybridisation and restriction analysis using standard protocols. One of the resulting clones was characterised by DNA sequence analysis.

Both of the methods (a) and (b) gave the same construct, designated p35SlacI. FIG. 10 shows the structure of vector p35SlacI.

(1.2) Replacement of the CaMV 35S promoter with maize CAB promoter

In order to demonstrate the general utility of the Lac repressor/operator system in plants, we have constructed an expression vector which will allow inducible and tissue-specific lacI expression in plants. For this work, we have used the promoter of the gene encoding the light-inducible maize chlorophyll a/b binding protein (CAB).

The construction of this vector was achieved by replacing the CaMV promoter in p35SlacI with the maize CAB promoter, the DNA sequence of which is given in FIGS. 12A to 12B herewith, which is found in vector pCAB48.1. The CaMV promoter was removed by restriction of p35SlacI with EcoRI and BamHI using standard conditions. The CAB promoter was isolated from pCAB48.1 by restriction with XbaI and Sau3A using partial restriction conditions for Sau3A. This promoter fragment was then inserted into the promoter-less p35SlacI. This vector, designated pCABlacI, has been characterised by restriction mapping and DNA sequence analysis.

(1.3) Transformation of tobacco plants

The expression modules from the vectors described above were transferred to BIN19 and then to tobacco using leaf disc transformation following standard protocols. The plasmids were transferred to Agrobacterium using triparental mating. Agrobacteria were purified, and used in leaf disc transformation experiments. Thirty-seven plants containing the CaMV-lacI expression module and thirty-eight plants containing the BAB-lacI construct were regenerated and analysed for the relative expression of lacI.

1.4 Analysis of transgenic plants for lacI expression

The expression of the lacI gene was monitored using Western analysis of extracted proteins. Extracts were prepared, proteins recovered on polyacrylamide gels and prepared for Western analysis. The analyses confirmed the expression of the lacI gene construct in the transformed plants. Different levels of lacI gene expression were observed in different independent transformants. The results for plants transformed with the CaMV-lacI construct are given in the following Table IV.

TABLE IV

| Plant Sample | Lac Expression (Band Intensity) |
| --- | --- |
| L1 | − |
| L2 | ++ |
| L3 | − |
| L5 | − |
| L7 | − |
| L8 | +++ |
| L9 | + |
| L10 | + |
| L11 | − |
| L13 | + |
| L14 | ++ |
| L15 | − |
| L16 | +++ |
| L18 | − |
| L22 | +/− |
| L23 | − |
| L24 | ++ |
| L25 | + |
| L26 | +++ |
| L27 | +++ |
| L28 | − |
| L29 | ++++++ |
| L31 | ++ |
| L32 | ++++ |
| L33 | +/− |
| L34 | +/− |
| L35 | ++ |
| L37 | + |

− → ++++++ indicates band intensity of Lac repressor from Western blots.

2. Insertion of the lac operator into target genes
(a) The maize CAB promoter

The maize CAB promoter can be found in plasmid pCAB48.1 and we have found that this promoter can drive expression of foreign genes in a transient tobacco expression system and in stably transformed plants. This gene, therefore, is an excellent target to demonstrate control through lacI as high levels of expression can be obtained both in vitro and in vivo. Secondly, the CAB promoter from other systems (wheat, pea and tobacco) have been extensively analysed in detail and reported in the literature. The published information facilitates the selection of suitable sites for operator insertion. Thirdly, pCAB48.1 is a maize promoter and the use of this system is important to demonstrate the applicability of this invention to monocotyledonous plants such as maize, wheat, barley and sorghum.
(b) Insertion of the lac operator into the maize CAB promoter Relatively little work has been reported concerning the characterisation of the important cis-acting elements of the CAB promoter. Therefore, a computer search comparing consensus upstream regulatory elements (UREs) of several plant genes against the CAB promoter was carried out. As anticipated, numerous putative UREs were found in both strands of the CAB promoter. A number of potential sites for operator insertion were selected.
1 5' of the CAAT box;
2. Between the CAAT and the TATA box;
3. Around the TATA box;
4. Between the TATA box and the transcription start point; and,
5. Between the transcription start point and the translation start point.

Two methods were used to insert the lac operator into the maize CAB promoter:
(1) insertion into naturally occurring restriction sites;
(2) using PCR to introduce operators at selected sites.

These methods were used to insert lacI operators into the selected sites.

Method (1)

Analysis of the promoter sequence shows that this region does not contain many unique restriction sites. However, two sites can be made available by simply recloning the promoter region into various vectors.

(a) Insertion between TATA and TSP

The restriction enzyme PvuII recognises a single site within the 2.8 kb PstI fragment containing the CAB gene. The site lies between the TATA element and the transcription start point (TSP) of the CAB promoter. However, the vector pCAB48.1 contains numerous PvuII sites (within pUC19). Therefore, the 2.8 kb PstI fragment was cloned into the standard cloning vector pAT153 (which lacks a PvuII site) to give pCABP1.

Operator sequences were inserted into the unique PvuII site within pCABP1. After sequencing, it was possible to determine which clones contain single and tandem operator insertions. The synthetic symmetric lac operator required for this work is shown below and is an 18 base pair palindrome that is analogous to a mutant operator which binds lac repressor eight times more strongly than the wild-type operator.

lac operator-1

5'-ATTGTGAGCGCTCACATT- 3'

(b) Insertion upstream of the CAAT sequence

The method used was as follows:

(i) pCAB48.1 was digested with HindIII, which cuts outside the promoter region and within pUC18, and BglII, which cuts downstream of the unique NcoI site and within the coding region. This gave a fragment with a unique SphI site upstream of the CAAT moiety; p0 (ii) pUC18 was digested with HindIII and BamHI and the promoter fragment from (i) above was inserted to give pCABP2. Digestion of pUC18 with BamHI removes the single SphI site from the polylinker. Therefore, pCABP2 contains a unique SphI site into which operators can be inserted.

The operator used in this procedure had the sequence:

lac Operator-2

5'-ATTGTGAGCGCTCACAATCAT G-3'

3,-GTACTAACTCTCGCGAGTGTTA-5'

It is important to note that in approaches (a) and (b) the operator sequences are not inserted directly into any putative regulatory elements although promoter activity is likely to be affected when the sequences are inserted elsewhere.

Method 2

As shown above, operator sequences can be inserted into two available restriction sites. Insertion into other sites requires other methodologies.

Insertion between TSP and ATG codon

This can be effected using PCR. Since a unique PvuI site lies close to the TSP region, it is used as a reference point for subcloning purposes. The starting material for the PCR reaction is pCABP1, that is, the pAT 153 CAB promoter vector constructed as described above. An oligonucleotide overlapping the PvuII site and containing no alterations was used to prime the reaction from one end: CAB Oligonucleotide-1

CAB Oligonucleotide-1
         PvuII
5'-GG CAGCTG CTGTGTTCTGTTATGAC-3'

The second oligonucleotide overlaps the NcoI site and contains the operator sequence shown below.

CAB Oligonucleotide-2
         NcoI                                    Operator 1
5'-GATAG CCATGG TGGCGGCAGCCATGTCG ATTGTGAGGCGCTCACAAT
--ATCAGATCGTAGCTCCTTCTGATGC-3'

CAB Oligonucleoide-3
         NcoI                                    Operator 1
5'-GATAG CCATGG TGGCGGCAGCCATGTCG ATTGTGAGGCGCTCACAAT
      Operator 2
-ATTGTGAGCGCTCACAAT ATCAGATCGTAGCTCCTTCTGATGC-3'

Following the PCR reactions, the newly synthesised DNA is cleaved with PvuII and NcOI. The fragment is then transferred to similarly digested pCABP1 and sequenced.

A slightly different approach which eliminates the intermediate cloning step into pCABP1 may also be used. This involves using an oligonucleotide which overlaps the unique XbaI site in the CAB promoter together with the operator nucleotides outlined previously. Digestion of PCR DNA with XbaI/NcoI results in a fragment which can be directly cloned into pCG1 and pCG2. However the XbaI to NcoI fragment from the PCR reaction is much larger than the PvuII to NcoI fragment obtained from the previous strategy.

Operator insertion between the CAAT and TATA This is effected using PCR.

CAB Nucleotide-4
            XbaI
5'-CCCAAACAG TCTAGA TATGTTTCTC-3'

CAB Nucleotide-5
            PvuII                     Operator
5'-CAGAACACAG CAGCTG CCTTTTATAC ATTGTGAGCGCTACACAAT-
-AGTTGGGTTTGGATAGCAGGTCATC-3'

CAB Nucleotide-6
            PvuII                     Operator 1
5'-CAGAACACAG CAGCTG CCTTTTATAC ATTGTGAGCGCTCACAAT-
      Operator 2
-ATTGTGAGCGCTCACAAT AGTTGGGTTTGGATAGCAGGTCATC-3'

Figure 11:
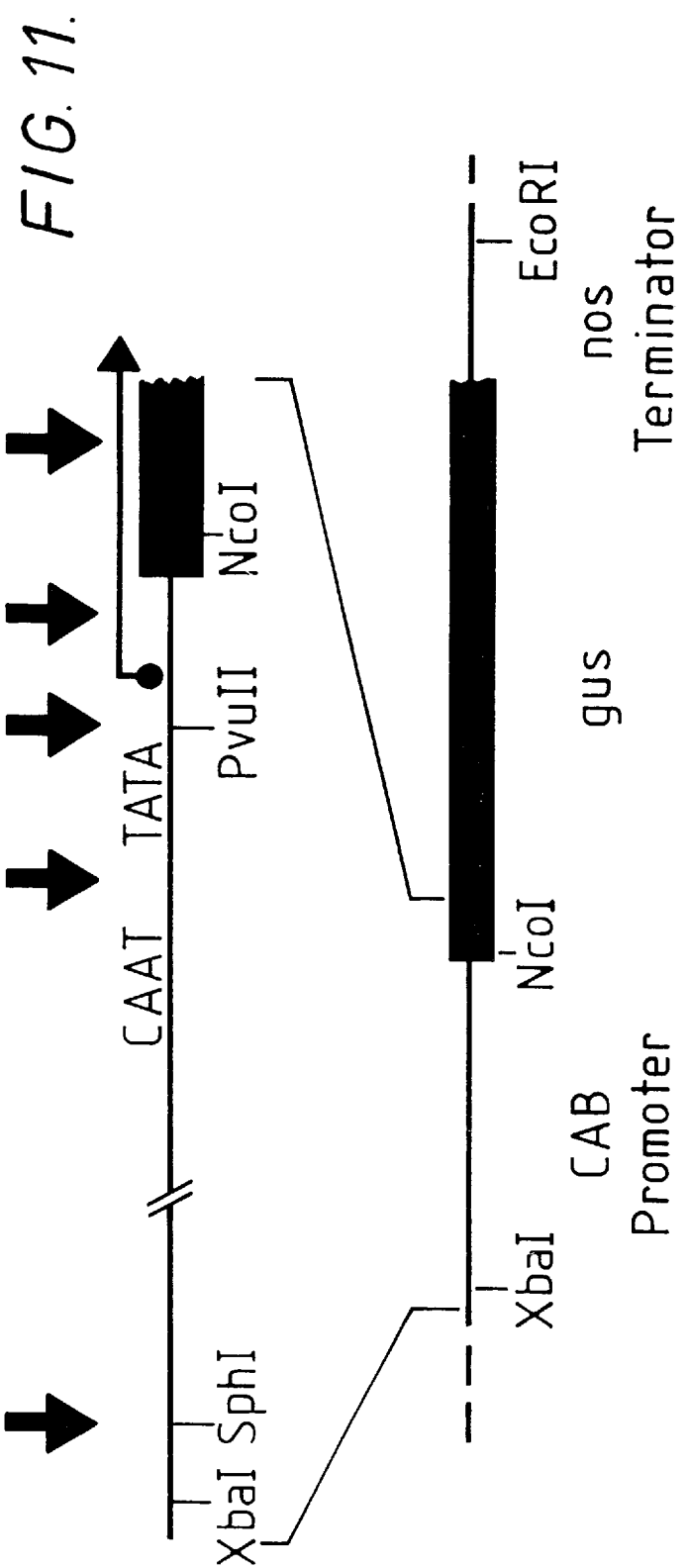
FIG. 11 shows the basic structure of pCG1 and pCG2.

Following PCR, DNA is digested with XbaI and PvuI and cloned into similarly digested pCABP1. Clones are again characterised by sequencing and any appropriate DNAs are digested with XbaI and NcoI and cloned into pCG1 and pCG2. The basic structure of these vectors is shown in FIG. 11.

The Camv 35S promoter

We have found that a promoter-less 35S vector is an excellent receptor for the insertion of activating sequences. The lac operator can be inserted into this vector, p-Δ-35S, and once inserted the 35S enhancer is cloned 5' upstream of the lac operator.

(3) Control of Gene Expression by Lac Repressor (a) Control of target gene expression in a transient expression system Plants which express lacI constitutively transformed with p35lacI may be prepared from protoplasts and, using methods described above) they may be tested for expression of the lacI protein. The target gene constructs may then be introduced into the protoplasts using standard methods and protocols. Protoplasts from untransformed plants can serve as control. Further control may be provided by protoplasts from plants expressing the GUS marker gene under the control of the CAB promoter without the operator insertions.

(b) Induction of gene expression using IPTG

IPTG can be used to overcome repression by the lac repressor. Thus, there is formed a switchable gene system.

(c) Modulation of expression of the target gene

Lac repressor/operator interactions can down-regulate marker gene expression in plants to different levels. This is an important effect in that there may be situations where a different degree of down-regulation may be required.

(d) Control of target gene expression in stably transformed plants

Having shown, as described above, that the lac-repressor can down-regulate CAB promoter driven GUS expression in protoplasts, suitable operator insertion constructs may be transferred to tobacco plants by the methods described above. The regenerated plants may be crossed with the lacI expressing plants described above, which express the lac repressor under control of the constitutive CaMV35S promoter.

Plants may also be constructed which express the lacI gene under control of the light-inducible maize CAB promoter. The expression of the lacI gene in these plants will then be light-inducible. These plants may be crossed with plants which contain the GUS marker gene from the CaMV promoter containing the lacI operator insertion.

Insertion of multiple operators into the CAB promoter

Using similar techniques as described for insertion of single operators, multiple operators can be inserted into the target promoter. This can either be by the insertion of multiple copies of the operator at one site, or the combination of fragments of the promoter in which the operator is inserted at different positions in the promoter, this yielding vectors in which the multiple operators are located at multiple locations in the promoter.

SECOND EMBODIMENT

In this embodiment the method of regulating gene expression comprises locating within or inserting into a gene a pseudo-operator sequence, and providing a mutant regulatory gene encoding a repressor having an amino acid sequence which binds to the pseudo-operator.

Cells containing interacting repressor and operator genes may be isolated by a method comprising preparing a recombinant plasmid containing (1) the *Escherichia coli lac* operon, which includes the lacz, lacY and lacA genes, and (2) a gene encoding a repressor protein, inserting said plasmid into a bacterial host and culturing same in the presence of ortho- or para-nitrophenyl-1-thio-β-galactosidase, whereby the growth of cells in which expression of the lac gene is not repressed by the said repressor molecule is inhibited whereas the growth of cells in which repressor/ operator binding occurs is not so inhibited, and recovering cells displaying non-inhibited growth characteristics.

Mutant repressors may be used or an exogenous potential pseudo-operator may be inserted within the operator region of the lac operon. The exogenous potential pseudo-operator is preferably of plant origin.

A convenient bacterial host is *Escherichia coli.*

Thus, we have a means for altering the repressor of gene expression enabling genes to be inactivated. Pseudo-operators are DNA sequences which maintain the overall dyad symmetry of an operator but which contain different constituent bases. Computer analysis of known DNA sequences of the French bean GPAL2 gene among many others, and promoter and the mammalian c-myc genes, has revealed a number of possible pseudo-operators to different bacterial repressors.

[The plasmid pGAL2 has been deposited in *Escherichia coli* strain DH5 on 6th Dec. 1988 with the National Collection of Industrial and Marine Bacteria, Aberdeen, United Kingdom, under the Accession Number NCIB 40087.]

Thus, it is probable 'pseudo-operator' sequences can be found in all genes. In general, then, a pseudo-operator is a DNA sequence present at a suitable position in a gene, including a plant gene, at which repressor binding will lead to inhibition of gene expression.

The plasmid pAD18 has been deposited, under the terms of the Budapest Treaty, in an *Escherichia coli*, strain DH5α, host, with The National Collections of Industrial and Marine Bacteria Limited, Aberdeen, United Kingdom, on 21 Dec. 1988, under the accession Number 40096.

The plasmid pPS1 has been deposited, under the terms of the Budapest Treaty, in an *Escherichia coli*, strain DH5α, host, with the National Collections of Industrial and Marine Bacteria Limited, Aberdeen, United Kingdom, on 21 Dec. 1988, under the accession Number 40097.

This procedure is also applicable to protein molecules which lead to an increase in gene activity, particulary the selection of repressors/activator proteins which respond to specific chemicals. Binding domains for these chemicals can be selected and specifically manipulated to allow the generation of specific protein/DNA effect chemical combinations which are of use in biotechnology, for example as a chemical switch package enabling the controlled regulation of plant genes by application of an exogenous chemical inducer.

Mutations which affect both repressors and operators occur in vivo. It has been shown that repressors which have altered DNA recognition specificities can be engineered in vitro. The procedure, then, depends on the ability of rare repressor mutants to switch off a conditionally lethal gene by binding at pseudo-operator sequences which the native repressor cannot recognise.

One embodiment of the invention will now be described, by way of illustration, in the following example, with reference to the accompanying drawing which shows a map representing two series of plasmids designated pPS and pAD and variants.

EXAMPLE

We demonstrate the selection system of the invention on repressor phage 434. However, in principle any other repressor can be adapted for this selection system.

1. The Selection System

We have designed a selection system that can be used for the selection of mutants in a wide range of repressor-operator systems. The selection system comprises a set of plasmids and the appropriate *E. coli* hosts, as well as a suicide substrate selection protocol adapted for the plasmids and hosts.

In its final form the system depends on the ability of rare repressor mutants to switch off a conditionally lethal gene through the binding at a 'pseudo-operator' which the wild type repressor cannot bind. The selection system described below contains features which maximise the frequency of such repressor mutants to be identified in the final population of cells.

The selection procedure is based on the lac operon of *Escherichia coli* and the use of the suicide substrate para-nitrophenyl-1-thio-α-D- galactoside (TPNPG). The lac operon (which contains the three genes lacZ, lacY and lacA) is controlled by the binding of LacI repressor to an operator sequence, laco, situated between the transcription start site and the lacz gene. The lacY gene product, lactose permease, is responsible for the active uptake of lactose and related compounds into the cytosol where they are hydrolysed by α-galactosidase (the lacz gene product) to form galactose and glucose.

The positive selection system exploits the discovery that the growth of cells expressing the lacY gene is selectively inhibited in the presence of TONPG or TPNPG, presumably through the waste of metabolic energy on its transport. The selectivity of these compounds has been shown to be enhanced when succinate is used as the carbon source.

The rationale behind the selection is based on the ability of 434 repressor to bind the pseudo-operator sequences inserted in the promoter driving expression of the lac gene cassette. In the absence of a 434 repressor/operator complex, the lac operon will be expressed and, in the presence of TPNPG, will result in cell death. Conversely, in the presence of a complex, the LacY permease will not be expressed, and the suicide substrate TPNPG will be unable to enter the cell. Consequently, in the final analysis, a pseudo-operator chosen from the natural sequence of the target plant gene will be cloned into the SalI site and combined with a pool of genes encoding 434 repressors in which certain amino acids in the α3 helix are randomly substituted. Only those cells expressing mutant repressor that is able to bind the pseudo-operator, and consequently repress lacY expression, will be selected in the presence of TPNPG.

2. The Plasmids

2.1 Construction of pAD18 and Derivatives

Figures 13A, 13B:
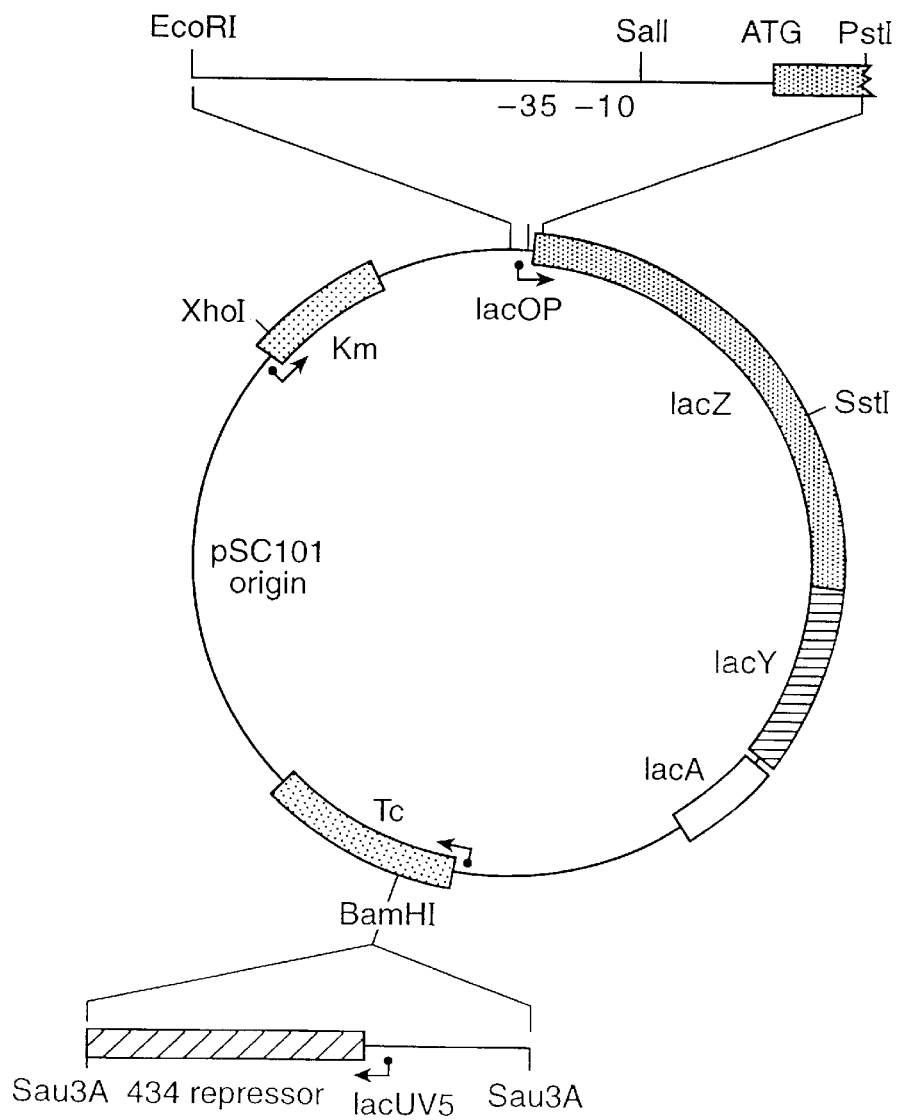
FIGS. 13A and 13B are maps of the pAD and pPS1 series of plasmids.

A series of plasmids have been developed for use in these experiments. The prototype of these is pAD18, a map of which is shown in FIG. 13B. This vector is based on a replicon from pSC101, which is known to be stably maintained in E. coli, and to have a low copy number. This is important as overexpression-of DNA binding proteins may have deleterious effects on the growth of the host. If this is a problem in some experiments, it is advisable to transfer genes contained on the pAD18 to a bacteriophage vector for insertion into the bacterial genome as a single copy gene.

pAD18 has a kanamycin selectable marker for maintainance in E. coli strains.

pAD18 also contains the lac operon. The lacz and lacY genes are present under the control of the lac promoter/operator. Into the lac operator, a SalI restriction site has been engineered which is used for insertion of the 434 operator, or in derivatives of pAD18, mutant 434 operators or selected 'pseudo-operators'. This site has been positioned in such a way that it will not interfere with expression of the lac operon from the lac promoter through steric hinderances when sufficient repressor is synthesised to bind to the operator cloned into that site. Those bases were changed into SalI restriction sites which are known not to be involved in contact with RNA polymerase. Thus the lac operon expression will be manipulated under the control of the 434 repressor. pAD18 which contains the wild-type 434 operator is thus the prototype of this series of plasmids.

pAD18 contains a tetracycline resistance gene, into which a wild type 434 repressor gene under the control of the lacUV5 promoter can be inserted for high level of expression. This vector is called pPS1. Further derivatives are described below.

In another vector, the 434 repressor has been modified such that a Kpn1 and Not1 site has been introduced at either side of the DNA binding helix whilst the native amino acid sequence in this region has been preserved. It is thus be possible to insert into this 434 repressor gene random oligonulceotides which when expressed will generate 434 repressor molecules which express altered DNA binding domains. The selection system using a suicide substrate will then permit the selection of those 434 mutant repressors which bind to the 'pseudo-operator'. In some circumstances this may also provide the selection pressure for isolation of repressor mutants. However, the system as it stands is dependent on expression/repression of the lacY permease for the isolation of repressor mutants.

Thus, there are convenient cloning sites in pAD18 and its derivatives for insertion of operators or repressor genes. Operators can be cloned into precursor vectors of pAD18, especially pRW283, from which the operator containing EcoR1 to Pst1 fragment can subsequently be excised and cloned into EcoR1 and Pst1 digested pAD18 (see FIGS. 13A to 13B).

One objective was to show that the expression of the lac operon carried by the plasmids described above could be controlled by 434 repressor/operator interactions. To demonstrate this, three plasmids were constructed in which the 434 operators carried by pAD16, 17 and 18 were combined with the wild-type 434cI gene on pAD15.2. The large XhoI/SstI fragment (9.4 kb) from pAD15.2 was purified and ligated to the small XhoI/SstI fragment (3.7 kb) purified from pAD16, 17 and 18 to form plasmids pPS2, pPS3 and pPS1, respectively. Restriction analysis of plasmid DNA isolated from several transformants from each ligation showed that all pPS plasmids had the expected overall structure. The structure of these plasmids is shown in FIG. 13.

The integrity of the operators carried by the pAD and pPS plasmids was checked by sequencing. Initially this was achieved by isolating the approximately 200 base-pair EcoRI/PstI fragment, which carries the whole of the lac promoter and the 5' end of the lacz gene, from each of the pAD and pPS plasmids and subcloning them into the polylinker of M13mp18. Single-stranded template was purified and sequenced according to standard protocols. Alternatively, this laborious subcloning procedure was circumvented by using plasmid sequencing. These analyses showed that the appropriate 14mer operator sequence was present at the SalI site in all relevant plasmids. The presence of other salient features of the lac promoter was also confirmed.

2.2 pPS plasmids encode functional 434 repressor.

To visualise the 434 repressor produced by pAD15.2 and the pPS plasmids, total protein extracts were prepared from mid-log cultures grown under selective conditions. Following polyacrylamide gel electrophoresis and Coomassie brilliant blue (G250) staining, no proteins corresponding to the size of the repressor could be observed specifically in strains containing the 434cI gene. However, other experiments have shown that $1 \mu g$ of purified repressor is only just visible using this relatively insensitive technique. Therefore, to detect 434 repressor in the amount of extract used an expression level of at least 1% total cell protein would be required. The background of other similar-sized proteins also makes detection difficult. Consequently, the much more sensitive Western blotting technique was used. The primary antibody required to detect 434 repressor by Western blotting was prepared by injecting rabbits with purified intact 434 repressor. The specificity of this polyclonal antiserum was demonstrated using purified repressor and extracts of E. coli strains harbouring the 434cI gene. At low dilutions of antiserum several proteins from bacterial extracts, including 434 repressor, were detected. However, further dilution of the antiserum resulted in only 434 repressor remaining detectable, the maximum specificity being observed at dilutions of $1/10000$ to $1/20000$.

The sensitivity of Western blotting using this antibody preparation and the horse-radish peroxidase conjugate detection technique was assessed by "spiking" crude cell extracts of 6300Δlac4169, which contains no 434cI gene, with various amounts of the purified repressor. Under standard conditions, 5 ng of repressor in 50 $\mu g$ of extract could readily be detected, this sensitivity corresponding to an expression level of 0.01% total cell protein.

Use of the same primary antibody in Western blots of 6300Δlac4169 strains carrying the test plasmids showed conclusively that cells harbouring pAD15.2, pPS1, pPS2 and pPS3 all synthesised 434 repressor. Determination of the relative intensities of the bands obtained, using a scanning densitometer, showed that all four strains contain approximately 0.4% total cell protein as 434 repressor.

Finally, the ability of the 434 repressor to bind wild-type operator sequences was determined in a functional assay using bacteriophage 434cI, 434vir and λcI. In the life cycle of these phage, the binding of the appropriate repressor to operators within the promoter $P_R$ represses transcription of the genes responsible for cell lysis. Consequently, cells which endogenously synthesise cI repressor are immune to lysis by the corresponding phage due to the inhibition of lytic gene expression by the already existing repressor. Since the cI mutant phage are unable to synthesise repressor, the lytic phenotype after infection by these phage is diagnostic for the absence of repressor in the host cell. The $P_R$ operators of vir mutant phage have a reduced affinity for repressor, with the consequence that at low levels of endogenous repressor this phage is lytic, whereas at higher repressor concentrations super-infection is inhibited.

The results of cross-streaking these phage with the test strains show that cells harbouring the pPS plasmids are immune to super-infection by both 434cI and 434vir, but are sensitive to λcI. Strains carrying other pAD plasmids were sensitive to all three phage. This clearly indicates that cells carrying the pPS plasmids synthesise high levels of 434 repressor that is functionally able to bind operator and inhibit transcription from $P_R$. Furthermore, the specificity of this repressor/operator interaction is demonstrated by the inability of 434 repressor to bind the operators of λcI, which have a different sequence to those of 434, resulting in cell lysis.

In summary, all three pPS plasmids were determined to be of the correct construction, to carry the expected 434 operator sequence and to synthesise functional 434 repressor.

2.3 VECTOR IMPROVEMENT

As indicated below, a proportion of the population of pAD and pPS plasmid-containing strains form white colonies upon selection. Furthermore, it has been observed that if strains containing these plasmids are kept on selective media for several months, sub-culturing when necessary, the proportion of white colonies in the population increases.

It is presumed that these white colonies carry plasmids in which part of all of the lac operon is mutated or deleted. The usual method of minimising such problems is to use a recombination-deficient strain. However, the combination of the Δlac4169 and recA56 alleles renders the strain inviable in the presence of TPNPG, the reason for this being unclear. Therefore, attention has turned to the probable source of the recombinatory events. It is noted that the promoters expressing the lac operon and the 434 repressor gene in the pPS plasmids are both derived from the lac promoter and consequently the sequences are very similar. Recombination between these sequences would result in the deletion of the lac operon, given that the origin sequences and the kanamycin-resistance gene must remain under the selective conditions imposed.

During the construction of pAD15.2, the 434cI gene was transferred from plasmid pRP42 on a 1 kb Sau3A fragment. The stop codon of the 434 repressor reading frame coincides with the Sau3A site at the right hand side of this fragment, consequently the gene cloned into pAD15.2 carries no transcriptional termination signals. Furthermore, this Sau3A fragment also carries a remnant of pBR322, including the ampicillin-resistance gene promoter. Therefore, to rectify these problems sequences both upstream and downstream of the 434cI coding sequence were altered. The region upstream was replaced with the tryptophan promoter and a consensus Shine-Dalgarno sequence using appropriate oligonucleotides. This both prevents intra-plasmidic recombination and removes the ampicillin-resistance gene promoter.

The rrn T1 terminator was also introduced at the 3' end of the 434cI coding sequence to terminate the 434cI gene transcripts. This rho-independent terminator was chosen since its reported bi-directional termination activity would avoid any disruption of 434cI expression from opposing transcripts initiated elsewhere in the vector as well as terminating 434cI transcripts.

2.4 Construction of plasmid pTP1.

Oligonucleotides were used to introduce the wild-type trp promoter sequence together with the consensus Shine-Dalgarno sequence (AGGAGGT) 5 base-pairs upstream of the 434cI gene translational start site. This spacing gives maximal translational activity of the 434cI gene. Due to the lack of convenient restriction sites at the start of the 434cI gene, the EcoRI site 33 base-pairs inside the coding sequence was used. This necessitated the inclusion of the 5' end of the coding region in the oligonucleotide. The required sequence is 126 base-pairs long and thus was constructed from four overlapping oligonucleotides. Following the annealling of these oligonucleotides, the duplex 126 base-pair fragment was isolated and cloned into EcoRI-cleaved pUC19 vector. Following the selection of transformants on media containing ampicillin and BCIG, DNA from several white colonies was sequenced using plasmid sequencing protocols. This confirmed the structure of the promoter sequence to be as expected.

2.5 Construction of pTT1.

The sequence of the rrn T1 terminator has a long G≡C rich stem structure flanked by long A=T rich regions making it a strong terminator for transcripts in both orientations. Due to the inverted repeat nature of this sequence, it was inserted using four oligonucleotides thereby avoiding any problems of self-annealling within each strand. The oligonucleotides were annealled pairwise and the resultant double-stranded DNAs isolated separately and ligated to EcoRI/HindIII cleaved pTP1 DNA, prior to transformation of cells to ampicillin-resistance. The sequence of the inserted terminator structure was ascertained.

2.6 Construction of plasmid pTRT1

The source of the 434cI gene to be cloned behind the trp promoter was plasmid pRP42-76. Silent mutations have been introduced, using in vitro mutagenesis, to create restriction sites for KpnI and XmaIII on either side of the sequence coding for the α3 recognition helix. This will subsequently allow the introduction of oligonucleotides in which certain codons in the α3 helix have been randomly mutated. The EcoRI/Sau3A fragment (approx. 600 base-pairs) carrying the 434cI gene was isolated and cloned into EcoRI/BglII cleaved pTP1. This reforms the 434cI open reading frame exactly and the translational stop codon is retained within the Sau3A/BglII junction. Once isolated, the trpP-434cI-rrnT1 cassette was cleaved out using the BamHI sites in the polylinkers introduced at either end of the cassette and used to replace the existing 434cI gene in the pAD and pPS plasmids.

The sequence of the trp promoter used to construct pTRT1 is bound by trp repressor in the presence tryptophan to inhibit transcription. The binding site for this repressor was intentionally retained in order that expression of the 434cI gene may be controlled, if necessary, in future work. However, in order to conveniently allow the synthesis of 434 repressor, strains will be constructed in which the trpR gene has been deleted from the chromosome.

3. Selection Protocol

3.1 Selection using TONPG

A TONPG (ortho-nitrophenyl-b-thiogalactoside) selection protocol was designed which allows selection for clones in which a mutant repressor now binds to the mutant 434 operator resulting in repression of lacY expression (i.e. selection by repression of conditional inhibition).

TONPG inhibits the growth of E. coli cells that are expressing the lacY permease gene. Early work with single copy lacY+ E. coli indicated that these cells were maximally sensitive to TONPG at 500 to 1000 micrograms/ml when expressing lacY in succinate minimal medium. Mixing experiments showed that TONPG could be used to select lacY cells from a mixed lacY+/−population. These experiments were repeated with lacY+ and lacY− pAD plasmids. The TONPG selection will only work in a lac-deleted E. coli host. The preferred host is described below. Selection works better in liquid cultures, but also works on agar plates. Selection on solid medium works better with a different galactoside analogue, para-nitrophenyl-beta- thiogalactoside (TPNPG). Using TONPG in liquid cultures and TPNPG in plates, the selection normally achieves a 6 log enrichment of lac-pAD plasmids present in the initial population.

3.2 The E. coli host

The bacterial host selected was such as to enable selection by TONPG. This required the ability of the host to grow in a succinate minimal medium. The particular host used in this Example was one from which the entire lac operon had been deleted, lacΔ4129. However, other suitable mutants hosts can be used, for example lacI⁻, lacY⁻. A suitable strain was constructed from strain W1485 (CGSC6300) derivative which was deleted for the entire lac operon, using transposon-linked P1 transduction.

3.3 Selection using TPNPG

To test the ability of TPNPG to select lac⁻cells from a background of lac⁺ cells, mixing experiments with cultures of 6300lac⁺ and its Δlac4169 derivative were performed. These strains were grown to mid-log phase in the presence of 1mM IPTG, to induce expression of the lactose operon. The two cultures were mixed in various proportions before plating suitable dilutions on minimal-salts-succinate plates containing 1mM IPTG and 50 $\mu$/l BCIG, both with and without TPNPG.

Initial experiments showed that 500$\mu$g/ml TPNPG was only able to retard the growth of lac⁺ cells, allowing the formation of small blue colonies after 48h at 28° C. However, this background was eliminated in the presence of 1 mg/ml TPNPG, resulting in none of the lac⁺ cells plated (up to $7 \times 10^{-7}$) being able to form blue colonies (Table V). In contrast, this TPNPG concentration did not noticeably affect the viability of the lac⁻cells. This demonstrates the high selective power of TPNPG againstlac⁺ cells, even when the lacY gene is chromosomal and thus at a low copy number. In this respect, the higher copy number and therefore increased expression level of the lac genes on the pPS plasmids should result in a greater waste of energy on TPNPG uptake, making the killing of lac⁺ cells more effective.

TABLE V

ABILITY OF TPNPG TO SELECT LAC− CELLS FROM A BACKGROUND OF LAC+ CELLS

| Approx. ratio of cells plated lac−:lac+ | Colonies formed/ml | | | |
|---|---|---|---|---|
| | −TONPG | | +TONPG | |
| | White | Blue | White | Blue |
| 1:10² | 1.1 × 10² | 2.0 × 10⁴ | 1.2 × 10² | 0 |
| 1:10³ | 1.3 × 10² | 2.0 × 10⁵ | 1.2 × 10² | 0 |
| 1:10⁴ | N.D. | 1.8 × 10⁶ | 1.1 × 10² | 0 |
| 1:10⁵ | N.D. | 1.5 × 10⁷ | 1.1 × 10² | 0 |
| 1:5 × 10⁵ | N.D. | 7.0 × 10⁷ | 1.2 × 10² | 0 |

N.D. = Not Determinable

The effect of TPNPG on the survival of 6300Δlac4169 cells carrying various pAD and pPS plasmids was tested by plating appropriate dilutions of cultures on the media as described above. The results from two experiments revealed that all plasmids resulted in the formation of both blue and white colonies in the presence of TPNPG, yet no white colonies were detected in its absence (Table VI).

TABLE VI

| Plasmid carried | Colonies/ml | | | |
|---|---|---|---|---|
| | −TPNPG | | +TPNPG | |
| | White | Blue | White | Blue |
| Expt #1 | | | | |
| — | 2.8 × 10⁸ | 0 | 3.0 × 10⁸ | 0 |
| pAD16 | ND | 3.5 × 10⁸ | 1.2 × 10³ | 2.0 × 10³ |
| pAD17 | ND | 2.3 × 10⁸ | 1.3 × 10⁴ | 1.6 × 10³ |
| pAD18 | ND | 2.3 × 10⁸ | 2.3 × 10³ | 2.2 × 10³ |
| pPS1 | ND | 3.8 × 10⁷ | 2.0 × 10⁴ | 2.7 × 10⁷ |
| pPS2 | ND | 7.2 × 10⁷ | 7.0 × 10² | 4.8 × 10⁷ |
| pPS3 | ND | 5.6 × 10⁶ | 2.0 × 10⁴ | 2.0 × 10¹ |
| Expt #2 | | | | |
| — | 3.1 × 10⁸ | 0 | 3.0 × 10⁸ | 0 |
| pAD16 | ND | 2.9 × 10⁸ | 1.1 × 10⁴ | 4.2 × 10² |
| pAD17 | ND | 3.4 × 10⁸ | 6.7 × 10³ | 5.9 × 10³ |
| pAD18 | ND | 2.7 × 10⁸ | 4.1 × 10³ | 2.5 × 10³ |
| pPS1 | ND | 4.2 × 10⁷ | 8.5 × 10³ | 1.2 × 10⁷ |
| pPS2 | ND | 8.4 × 10⁷ | 5.2 × 10³ | 1.6 × 10⁷ |
| pPS3 | ND | 5.8 × 10⁷ | 5.7 × 10³ | 6.3 × 10¹ |

ND = Not Determinable

As already observed, all pAD and pPS plasmids give blue colonies on media containing BCIG, irrespective of the presence of 434 repressor/operator interactions. Presumably therefore, the white colonies formed must result from cells carrying plasmids which have been mutated or deleted to render the cell effectively lac⁻. The relatively low frequency with which these white colonies occur (approx. $10^{-5}$ of cells plated) suggests that, on media lacking TPNPG, they would remain undetected amongst the majority of blue colonies. Analysis of the plasmids harboured by cells of such white colonies revealed deletions (see above).

In the presence of TPNPG the frequency of blue colonies formed by pAD-carrying strains was reduced by $10^5$ to $10^6$. This represents the killing by TPNPG of the majority of the population harbouring an un-repressed lac operon. The strain carrying pPS3 was also killed to a similar extent in the presence of TPNPG, as would be expected given that it has already been shown that the 434 repressor is incapable of inhibiting transcription of the lac genes in this plasmid. However, in all cases, a residual number of blue colonies were obtained in the presence of TPNPG, at a frequency of approximately $10^{-5}$ of the cells plated. It is presumed that these colonies primarily represent cells harbouring lacY mutant⁻plasmids, since it has already been demonstrated that the selective power of TPNPG is sufficient to kill the vast majority of the cells plated, given that they all remain lac⁺. Since previous experiments have not indicated a high mutation frequency for the chromosomally borne lacY gene, it is presumed that intra-plasmidic recombination is responsible for the apparently high number of mutants. Previous work has indicated that these plasmids are prone to instability in rec⁺ strains and that a 6300Δlac4169 recA56 strain, which could be used to prevent such recombination, is inviable on TPNPG.

However, in sharp contrast to the other strains, the vast majority of cells containing pPS1 or pPS2 survive in the presence of TPNPG, the number of blue colonies being reduced by only 2–5 fold, this reduction being least for pPSI. This clearly correlates with the emphatic reduction in β-galactosidase activity, and therefore also presumably lacY expression, already demonstrated for these plasmids. Therefore, the important conclusion can be drawn that the interaction between 434 repressor and its cognate operator is able to reduce lac gene expression sufficiently to allow the majority of cells to survive the selective procedure.

4. Selection of Altered Specificity Repressors

4(a) Selection of altered 434 repressor

A 434 gene which had been altered to facilitate random mutagenesis of the 434 repressor binding domain through insertion of random oligonucleotides has been described (Wharton and Ptashane, Nature 316, 601–605). The 434 repressor gene has been mutagenized to introduce KpnI and NotI restriction enzyme cleavage sites on either side of the DNA recognition helix, whilst conserving the native amino acid sequence. Batches of oligonucleotides have been synthesised with the correct cohesive ends and containing varying frequencies of mutations randomly distributed throughout the DNA recognition alpha helix. These oligo mixtures have been cloned between the KpnI and the NotI cohesive ends of the modified 434 repressor gene. Alternatively the 'dirty oligo' approach has been used for the generation of mixed oligo with base substitutions at appropriate positions of the DNA binding domain.

4(b) Selection of altered 434 repressor recognising pseudo-operator found in plant genes A naturally occurring pseudo-operator was used for the selection of altered repressor. The target for this work was the GPAL2 gene from French bean, the chlorophyll a/b binding protein gene from maize, and others. We have identified by computer analysis, that several potential 434 pseudo-operators are located in the region of the GPAL2 gene. These regions of the GPAL2 promoter were used to select an altered specificity 434 repressor. The 'pseudo-opertor' sequences were inserted into the −10 to −35 region of the lac promoter driving the lacz/lacY genes. Dirty oligo's were inserted into the 434 repressor gene and mixtures were transformed into *E. coli* 6300. The selection protocol was applied and colonies isolated. Using microbiological and molelcular techniques we have demonstrated that mutant repressors can be selected for. The characterisation of the repressor gene has been done by DNA sequence analysis, and binding studies to determine the strength of the repressor binding.

In summary, then, the present invention provides a selection system comprising preferably of bacterial strains and plasmids, and a sensitive suicide substrate selection protocol. This selection system can be used to select altered specificty repressors. Implied in this invention is the provision of controlling gene expression in organisms by said altered- specificity repressors. The only requirement for this method of control of gene expression are the DNA sequence of the target gene, the identification of 'pseudo-operators' being a DNA sequence that resembles the normal operator sequence and a selection system which permits the selection of repressors capable of binding to said 'pseudo-operators'.

III. Male Flower Specific Gene Sequences

This module contains male flower specific DNA sequences comprising the polynucleotides shown in FIGS. 15A to 15G, 16A to 16C, 17A to 17E herewith, which are specifically expressed in male flower tissue.

Plasmid PMS10 in an *Escherichia coli* strain R1 host, containing the gene sequence shown in FIGS. 15A to 15G herewith, has been deposited with the National Collection of Industrial & Marine Bacteria on 9th Jan. 1989 under the Accession Number NCIB 40098.

Plasmid pMS14 in an *Escherichia coli* strain DH5α host, containing the gene control sequence shown in FIGS. 16A to 16C herewith, has been deposited with the National Collection of Industrial & Marine Bacteria on 9th Jan. 1989 under the Accession Number NCIB 40099.

Plasmid pMS18 in an *Escherichia coli* strain R1 host, containing the gene control sequence shown in FIGS. 17A to 17E herewith, has been deposited with the National Collection of Industrial & Marine Bacteria on 9th Jan. 1989 under the Accession Number NCIB 40100.

The isolation and characterisation of these cDNA sequences and the utilisation of these cDNA sequences as molecular probes to identify and isolate the corresponding genomic sequences will now be described.

The clones carrying the genomic sequences and the preparation of a promoter cassette from one of the clones illustrated using an approach and techniques which may be equally applied to any of the the clones. Furthermore the preparation of a promoter fusion to a reporter gene and the transformation of this construct into a test species is described.

Unless stated otherwise, all nucleic acid manipulations are done by standard procedures described in Sambrook, Fritsch and Maniatis, "Molecular Cloning: A Laboratory Manual", Second Edition 1989.

EXAMPLE 1

1. Isolation and Characterisation of Male Flower Specific cDNA from Maize

Figure 14:
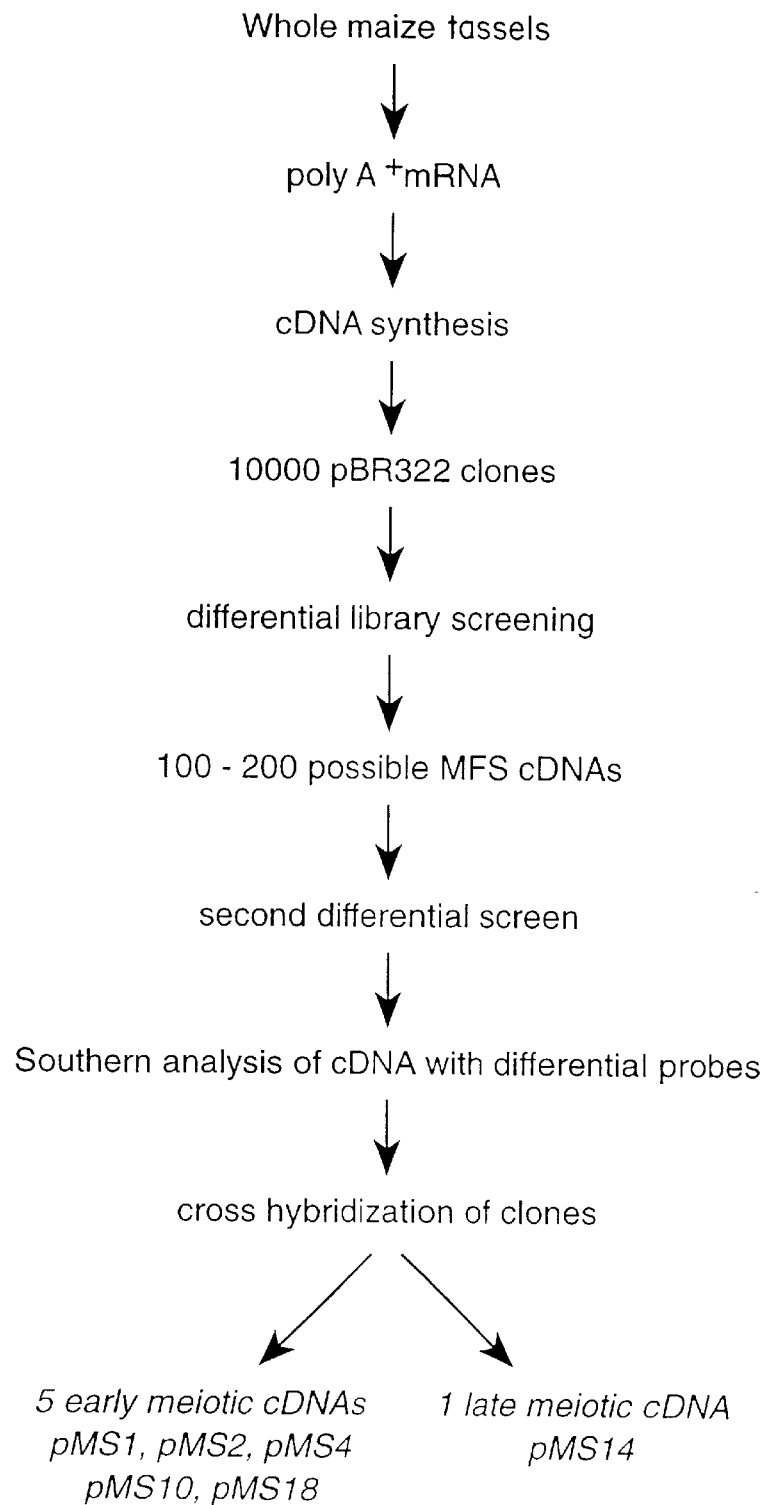
FIG. 14 shows the library screening procedure used for the isolation of maize flower specific clones.

To clone cDNAs to genes which are expressed in the male flowers of maize we constructed two cDNA libraries. In maize, the male flowers are born in the tassel which terminates the main stem. Library 1 was prepared from poly [A] RNA from whole maize tassels bearing early meiotic anthers (most meiocytes in early meiotic prophase) and library 2 from poly [A]+ RNA from whole tassels bearing late meiotic anthers (predominantly diad and early tetrad stages). FIG. 14 reviews the library screening procedure used and this yielded five unique early meiotic MFS cDNAs and one unique late meiotic CDNA. Clone PMS3, a partial cDNA of 120 base pairs, isolated by the differential screening process, was subsequently used as a hybridisation probe to isolate the corresponding pending near full-length clone, PMS18.

Table VII below summarises some of the features of each of these cDNA clones. Expression of the mRNAs of the five MFS cDNAs isolated from the early meiotic library is detected in RNA isolated from both early and late meiotic tassel samples. The mRNAs corresponding to these cDNAs are not wholly specific to male flowers and are detected at considerably lower levels in leaves (pMS10 and pMS18) or in leaves, cobs and roots (pMS1, pMS2 and pMS4) Table VII. In contrast pMS14 mRNA is found only in late meiotic RNA and is not detected in leaves, cobs or roots (Table VII).

TABLE VII

|  | pMS1 | pMS2 | pMS4 | pMS10 | pMS14 | pMS18 |
|---|---|---|---|---|---|---|
| Library 1 | 1 | 1 | 1 | 1 | 2 | 1 |
| Insert size 2 | 750 | 500 | 720 | 1350 | 620 | 940 |
| mRNA size 3 | 900 | 950 | 850 | 1600 | 900 | 1100 |
| Organ specificity 4 | + | + | + | ++ | +++ | ++ |
| Expression window 5 | E/L | E/L | E/L | E/L | L | E/L |

Table Legend
1 Isolated from cDNA library 1 (early meiotic) or library 2 (late meiotic.
2 Approximate size in base pairs.
3 Approximate size in nucleotides.
4 + = expresed in tassels and at much lower levels in leaves, cobs and roots.
++ = expressed in tassels only and at much lower levels in leaves. +++ = expressed in tassels only.
5 E/L = mRNA present in RNA from both early and late meiotic tassels. L = mRNA present only in RNA from late meiotic tassels.

We have examined expression of the genes corresponding to these cDNAs during tassel development using dot blot hybridisations (FIG. 15). The dot blot analysis was generated by binding total; RNA to nitrocellulose followed by hybridisation to radiolabelled pMS cDNAs. All filters were exposed to film for 48 hours at −70° C. except pMS10 which was exposed for 168 hours. The tassel lengths in each sample were as follows: A≧2cm; B=2–5 cm; C=5–10 cm; D=10–15 cm; E=15–20 cm; F=20–30 cm; and G=20–30 cm. The solid bars in FIG. 15 show the developmental stage relative to microsporogenesis in each of the samples: PM=premeiosis M=meiosis; IP=immature pollen; and MP=mature pollen.

The early meiotic mRNAs (pMS1, 2, 4, 10 and 18) accumulate very early in development in tassels less then 2 cm in length. We have not analysed expression in floral meristems prior to this stage. These mRNAs persist through the meiotic anther stages and then decline as pollen grains mature. In contrast the late meiotic mRNA of pMS14 is not detected in tassels less then 5 cm in length, but increases dramatically as the sporogenous cells of the anther enter meiosis. As with the early meiotic mRNAs, pMS14 mRNA declines abruptly as mature pollen accumulates in the anthers.

These data show that different temporal controls of gene expression occur during development of male flowers in maize. The controls which programme accumulation of the early meiotic mRNAs are probably very similar but contrast markedly with those regulating appearance and accumulation of the late meiotic mRNA, pMS14. Both the early and late meiotic mRNAs are involved with developmental processes which occur prior to the accumulation of mature pollen grains. They are clearly not involved with the later stages of anther development such as dehiscence nor are they mRNAs which accumulate in mature pollen.

The technique of in situ hybridisation has been used to determine the tissue localisation of MFs mRNAs in male flowers of maize. The techniques used are described in Wright and Greenland (1990; SEB Seminar Series, vol 43 ed by N Harris and D Wilkman. Cambridge University Press, Cambridge; in the Press). The data shown is that for pMS14 mRNA.

In situ hybridisation with pMS14 antisense RNA probes were carried out. Sense and antisense probes were prepared by sub cloning a 300 basic pair fragment of pMS14 into the vector, pBS, followed by preparation of radiolabelled T3 and T7 polymerise transcripts utilising methods suggested by the supplier of the vector (Stratagene, Trade Mark). These hybridisations shows that pMS14 mRNA is located in the tapetal cell layer surrounding the developing microspores. Hybridisation of the pMS14 antisense probe did not occur to any other cells in the section. Likewise the pMS14 sense probe did not show any specific hybridisation. Sections were made from 15–20 cm maize tassels at a stage when the level of pMS14 mRNA is at a maximum. In these sections and in those from subsequent experiments hybridisation occurs to the tatetum of the anthers in one floret but not the other. The tapetal layers which contain pMS14 mRNA were found to surround late meiotic microspores at the tetrad stage whilst the tapetal layers not containing pMS14 mRNA were found to surround sporogenous cells which have not undergone meiosis. It is a feature of maize that the sets of anthers within the individual florets of the spikelet do not develop co-ordinately. Thus in situ hybridisation shows that accumulation of pMS14 mRNA is tissue-specific and confirm data obtained from dot blot analysis that expression of PmS14 mRNA is stage specific as it is first detected in tapetum surrounding meiotic cells.

EXAMPLE 2
Determination of DNA sequence of pMS10

DNA from cDNA clone, pMS10, for sequence analysis by subcloning into M13mp18 using standard procedures. The nucleotide sequences of the subclones were determined by the dideoxy method using standard procedures. In addition a Sequence (Trade Mark) method was used utilising methods described by the suppliers. Regions of the clones were sequenced by priming with synthetic oligonucleotides synthesised from sequence obtained from previous gel readings. oligonucleotide concentrations used for priming were identical to those used with universal primers.

MFS, Clone pMS10 full length cDNA of 1353 base pairs. The complete nucleotide sequence and the predicted amino acid sequence are shown in FIGS. 15A to 15G. The sequence contains an open reading frame of 1022 nucleotides encoding a polypeptide of 341 amino acids with a deduced molecular weight of 37371 kd the polypeptide is rich in glycine residues. The open reading frame is flanked by 5' and 3' non-translated regions of 129 and 201 bases respectively.

EXAMPLE 3
Determination of DNA sequence of pMS14

Procedure of determining nucleotide sequence as described in Example 2.

Clone pMS14 is an in complete cDNA of 581 base pairs the complete nucleotide sequence and deduced amino acid sequence are shown in FIGS. 16A to 16C. The sequence contains an open reading frame which extends from nucleotide 1 to 278 encoding a partial polypeptide of 127 amino acids. The polypeptide is particularly rich in alanine and arginine residues. The open reading frame is flanked by 3' non-coding region 203 nucleotides. A consensus processing and polyadenylation signal hexanucleotide, AATAAA occurs at position 548.

EXAMPLE 4
Determination of DNA sequence of pMS18

Procedure for determining nucleotide sequence as described in Example 2.

Figure 19:
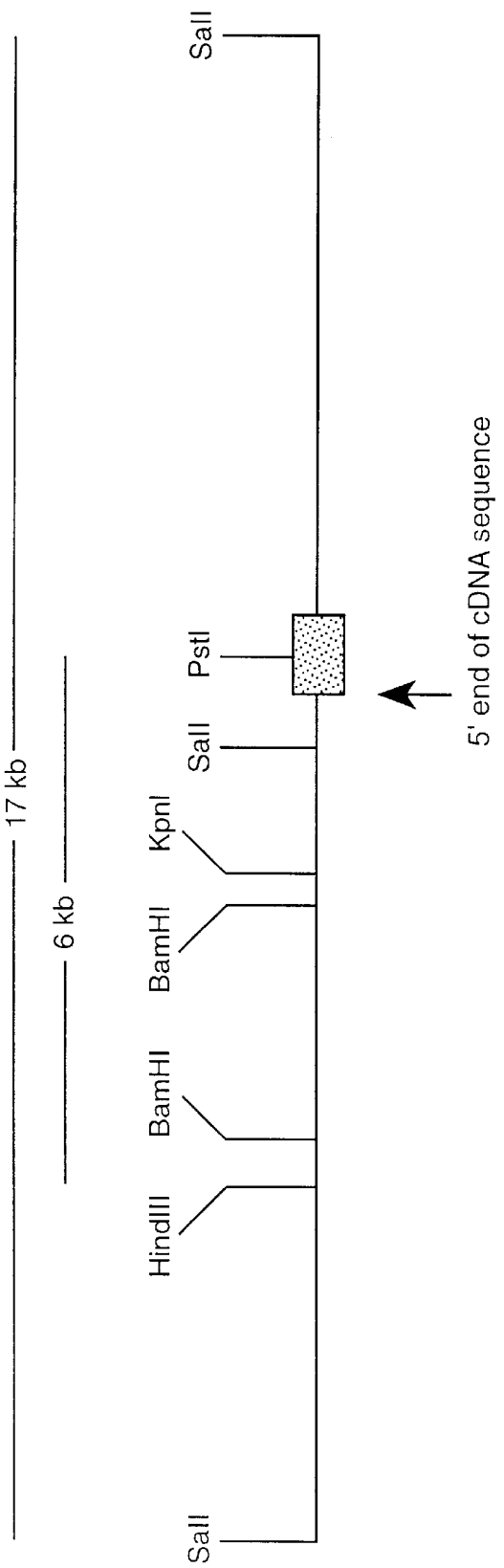
FIG. 19 is a restriction map of the 9 kb EcoRI fragment from clone 14/17M.

Clone pMS18 is a near full-length cDNA of 933 bases. The complete nucleotide sequence and deduced amino acid sequence is shown in FIG. 19. pMS18 lacks 28 nucleotides at its 3' terminus. The missing nucleotides are present in clone pMJ3 which overlaps the sequence of pMS18 by a further 91 nucleotides. pMS3 was the original clone isolated by differential screening of cDNA inbranes and was subsequently used as a hybridisation probe to isolate pMS18. pMS18 contains an open reading frame extending from nucleotide 151 to 813 and encodes a polypeptide of 221 amino acids with a deduced molecular weight of 25 kilodartons. The polypeptide is particularly rich in arginime residues. The open reading is flanked by 5' and 3' non-coding regions of 150 and 120 nucleotides respectively.

EXAMPLE 5
Isolation of genomic clones corresponding to pMS10

Figure 18:
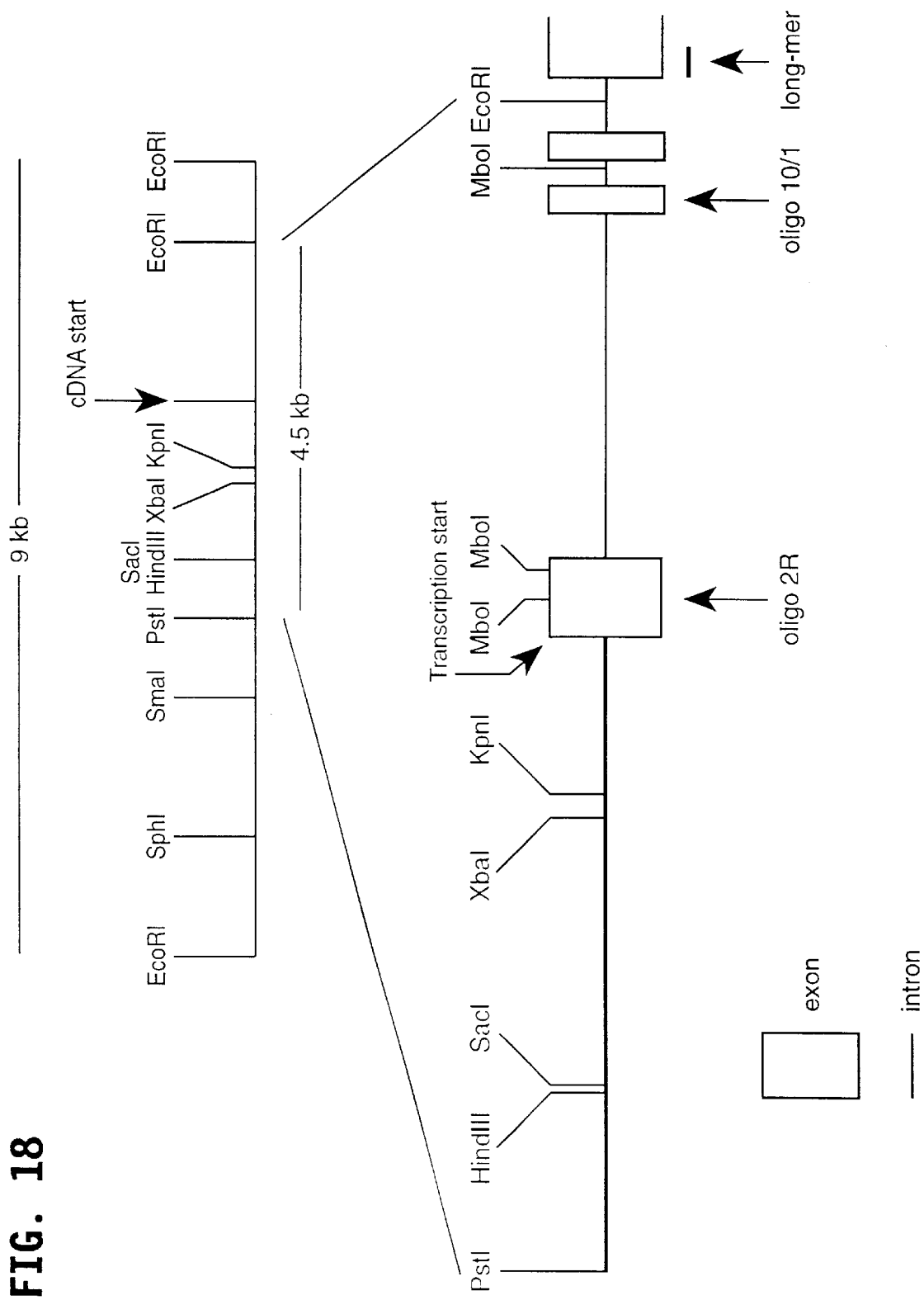
FIG. 18 is a restriction map of the 9 kb EcoRI fragment from clone 10/CT8-3.

Genomic DNA clones carrying genes corresponding to the cDNA, pMS10 were isolated from an EMBL 3 phase library of partial Mb01 fragments of maize DNA. The library was screened using radiolabelled "long-mer" probes synthesised in an in vitro labelling system. This system comprised, 50 mg of a synthetic 100 base oligonucleiotide (base position 452–551 at pMS10; FIGS. 15A to 15G. 500 mg of a synthetic primer olignucleotide, sequence-TAGTTTCCT-CGGTAG and which will base pair with the 3' end of the long olionucleotide, one or two radiolabelled oligonucleotides (usually$^{32}$ PdCTP and/or$^{32}$P-dGTP) and 5–10 units of the Klenow fragment of DNA polymerase 1. The reactions were performed at 37° C. for 30 minutes in a buffer identical to that used for the "random-priming" method of DNA labelling except that the random hexanucleotides were omitted. Five million phase clones immobilised on nylon "Hybaid" (Trade Mark) filters were hybridised at 65° C. with these probes using prehybridisation and hybridisation buffers suggested by the suppliers of the filters (Amersham International). Filters were washed on 3×SSC, 0.1% SDS at 65° C. using these procedures 50–60 EMBL3 phage clones containing either complete or partial regions of a pMS10 gene were obtained. The DNA from three EMBL3 phage clones 10/CT8-1, 10/CT8-3 and 10/CT25-3 which combined complete pMS10 genes was prepared and analysed by restriction enzyme digests. Each of these clones was shown to contain a common 9 Kb EcoRI fragment which extends from the third intron of the pmS10 gene into the 5' non-coding and promoter regions of the gene. A partial restriction map of the 9 Kb EcoRI fragment is shown in FIG. 18.

EXAMPLE 6

Isolation of geomic clones corresponding to pMS14

To isolate genomic DNA clones carrying genes corresponding to the cDNA, pMS14 two approaches were taken. In the first approach the method shown in Example 5 was adopted except the 5 million phage clones were screened with the complete cDNA sequence and the wash stringencies after hybridisation procedure yielded two positive clones 14/CTA and 14/CTD. In the second approach a 12 Kb EcoRI cut fraction of maize geomic DNA, shown by Southern Blotting to carry the pMS14 gene, was ligated into EcoRI cut λ phage EMBL4 DNA to produce a library of cloned 17 Kb DNA fragments. Roughly 200,000 clones were screened as described above, and two positive clones, 14/17m and 14/17R which combined a 17 Kb EcoRI fragment which hybridized to pMS14, were isolated. On further analysis the two positive clones isolated from the partial MboI/EMBL3 library were found to contain an internal 17 Kb fragment. A partial restriction map of this 17 Kb EcoRI fragment, common to all the clones, is shown in FIG. 19.

EXAMPLE 7

Isolation of genomic clones corresponding to pMS18

Figure 20:
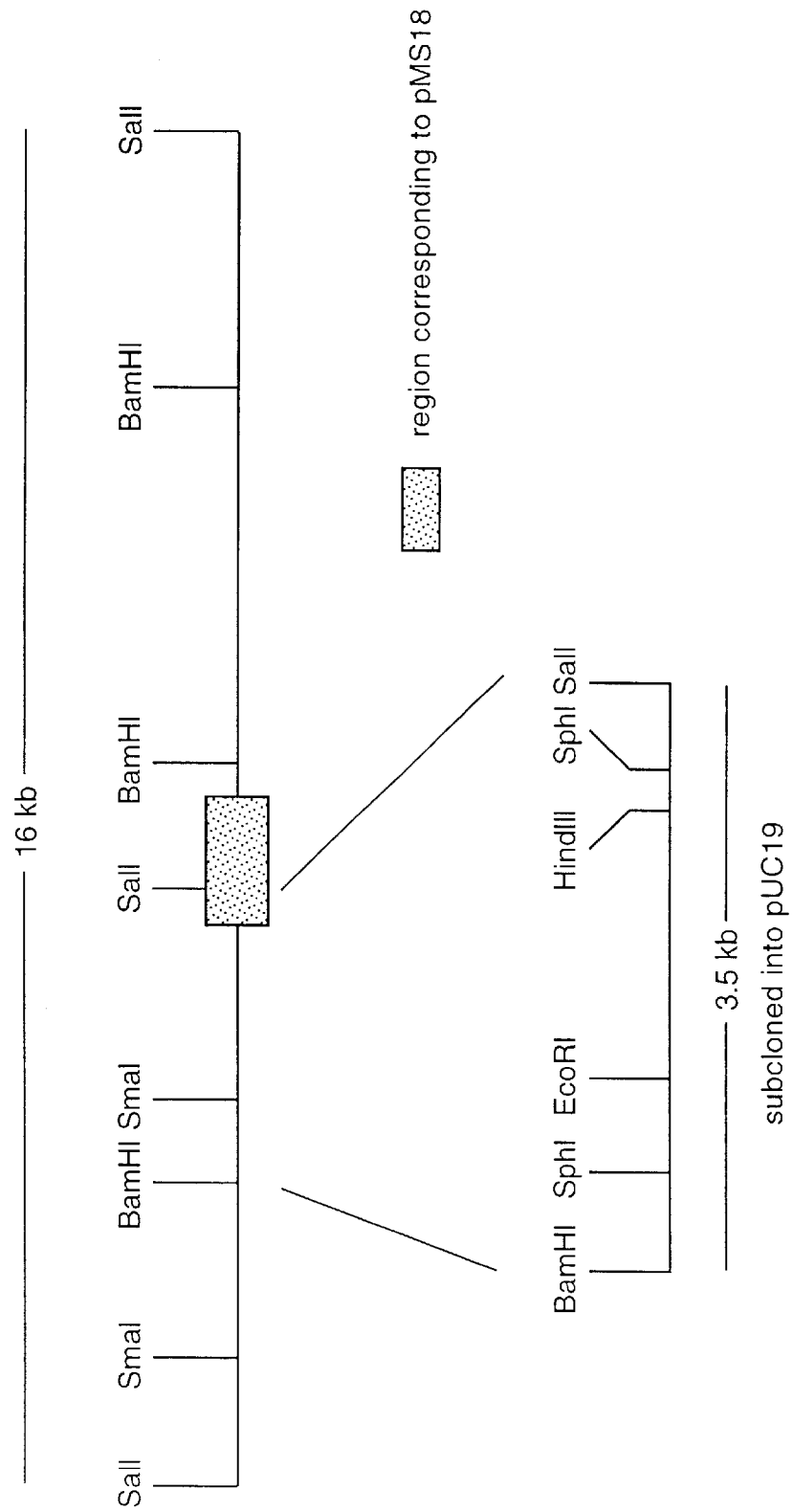
FIG. 20 is a restriction map of the 9 kb EcoRI fragment from clone 18/CT3.
Figure 21:
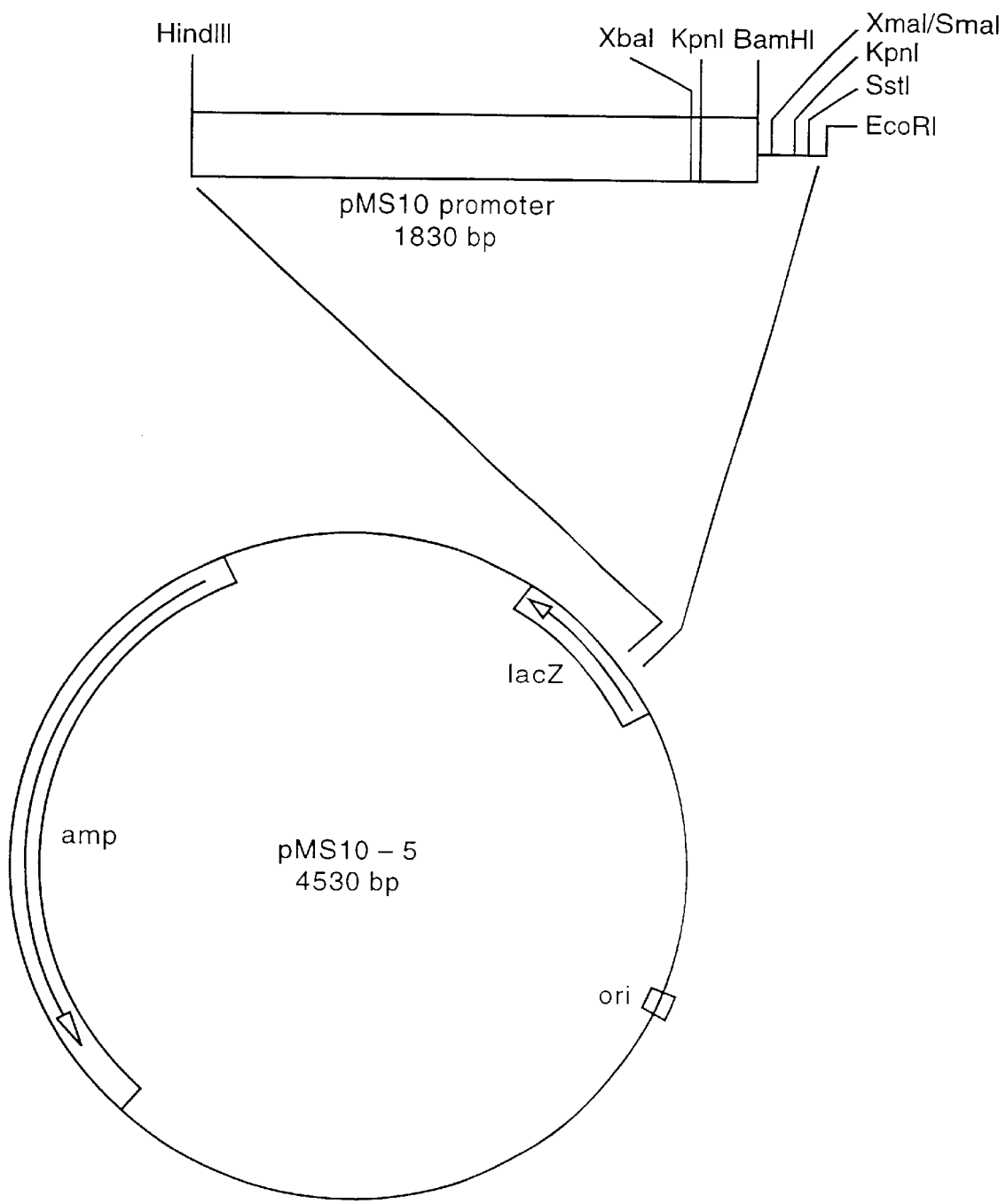
FIG. 21 is a plasmid map of clone pMS10-5.

To isolate genomic DNA clones carrying genes corresponding to the cDNA pMS18, the procedure described in Example 5 was adopted. Five million EmBL3 phage clones were hybridized to a "long-mer" probe derived from the sequence of pMS18, position 133–222). The sequence of the 3' complementary oligonucleotide was a 5'-GCCTCGGCGGTCGAC-3'. Two clones, 18/CT3 and 18/CT23, carrying the pMS18 gene were isolated from this screen. Restriction mapping of these clones showed that they both contained a 4.5 Kb BamHI-SalI fragment comprising the 5' region of the coding sequence of pMS18 and approximately 4 Kb of the promoter and upstream region of the gene. A partial restriction map of clone 18/CT3 is shown in FIG. 20.

EXAMPLE 8

Construction of a promoter cassette derived from 10/CT8-3

The following subclones from the λEMBL3 clone 10/CT8-3 were made. The 4.5 Kb PstI-EcoRI fragment was cloned into pUC18 to give pMS10-2. The 2.7 Kb XbaI-EcoRI fragment was cloned into pUC 18 to give pMS10-3. The 1.6 Kb HindIII to XbaI fragment was cloned into pUC18 to give pmS10-4.

The polymerase chain reaction (PCR) was used to amplify a 930 bp fragment from pMS10-3. The primers used for the PCR reaction were as follows. Primer pUC/2 is homologous to pUC sequence flanking the polylinker site. Primer 10/9 is complementary to the sequence of pMS10 from position 106–129 except that it contains an additional thymidine residue between bases 123 and 124. The sequence of these primers is:

pUC/2 5' CGACGTTGTAAAACGACGGCCAGT-3'

10/9 5' AGTCGGATCCCGCCCCGCGCAGCCG-3'

Following amplification in the PCR reaction a DNA fragment is produced in which the flanking XbaI site and the sequence identical to that present in the corresponding region of clone 10/CT8-3 up to the base immediately prior to the translation initiator are faithfully reproduced except that a novel BamHI site is introduced by the introduction of the thymidine residue. This 930 bp fragment was gel purified, and digested with XbaI and BamHI. It was then cloned into pMS10-4 which had been previously digested with XbaI and BamHI to yield clone pMS10-5. In pMS10-5 the sequences required for promoter activity associated with the MS10 gene are reacted and modified such that the promoter can now be fused to any gene via the BamHI site which occurs immediately prior to the translation start point. That these and no other modifications had occurred was confirmed by sequence analysis.

EXAMPLE 9

Figures 22A, 22B:
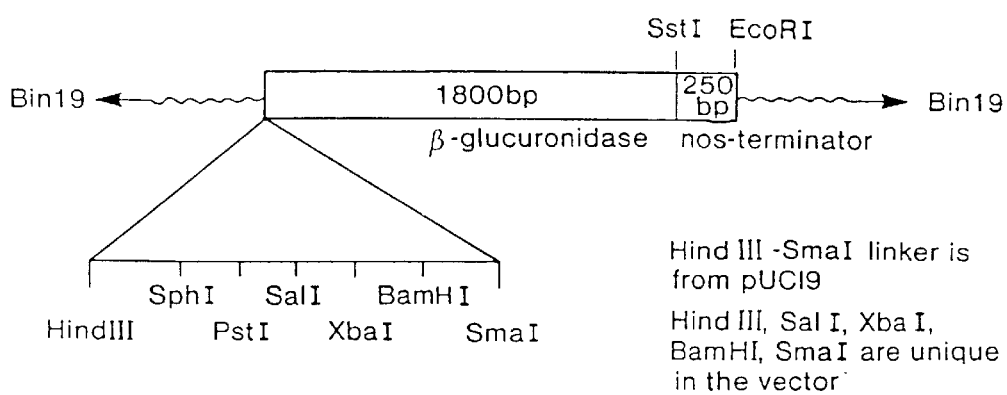
FIGS. 22A to 22B show the structure of pTAK1, pTAK2 and pTAK3.
Figure 23:
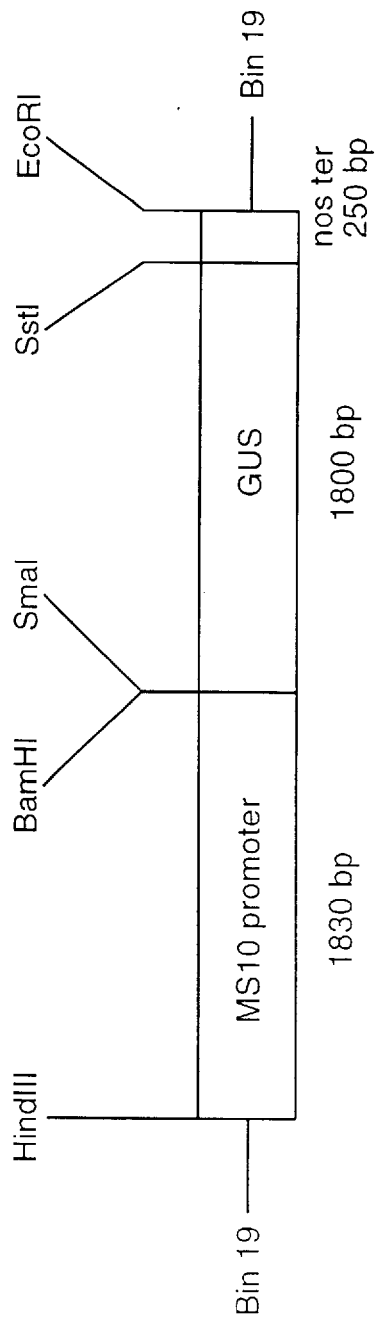
FIG. 23 is a map of clone pMS10-6GUS.
Figure 36:
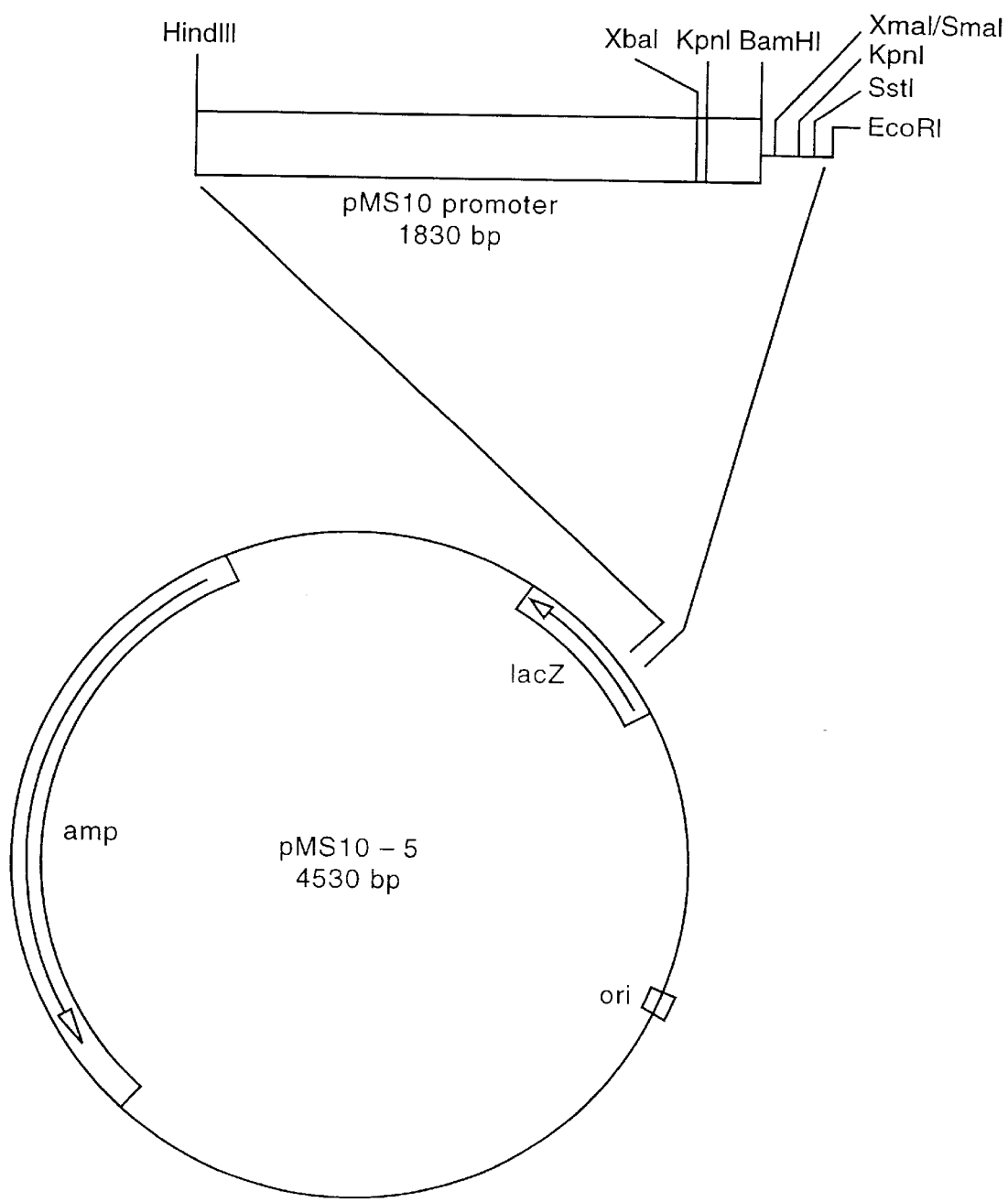
FIG. 36 is a plasmid map of pMS10-5.

Construction of a promoter fusion between Ms10 gene and the glucuronidase reporter gene The 1830 bp HindIII to BamHI fragment from pMS10-5 (FIG. 36) was ligated into pTAK1, previously cut with HmdIII and BamHi. pTAK1 is based on the binary plant transformation vector Bin 19 (Bevan, 1984; Nucleic Acids Research 12, 8711) and carries the glucuronidase (GUS) reporter gene and Nos 3' terminator (FIGS. 22A to 22B). The resulting plasmid was termed pMS10-6GUS and makes a transcriptional gene fusion between the promoter of the MS10 gene and the GUS reporter gene.

EXAMPLE 10

Transformation of tobacco plants with MS10 promoter gene constructs

The recombinant vector pmS10-6GUS as mobilised from E. Coli (TG-2) onto Agrobacterium tumefaciens (LBA4404) in a triparental mating on L-plates with E Coli (HB101) harbouring pRK2013. Transconjugants were selected on minimal medium containing kanamycin (50 µg/cm$^3$) and streptomycin (500 µg/cm$^3$).

L-Broth (5 cm$^3$) containing kanamycin at 50 g/cm$^3$ was inoculated with a single Agrobacterium colony. The culture was grown overnight at 30° C. with shaking at 150 rpm. This culture (500µd) was inoculated into L-Broth containing kanamycin (50 µg/cm$^3$) and grown as before. Immediately before use the Agrobacteria were pelleted by spinning at 3000 rpm for 5 minutes and suspended in an equal volume of liquid Murashige and Skoog (MS) medium.

Feeder plates were prepared in 9 cm diameter petri dishes as follows. Solid MS medium supplemented with 6-benzylaminopurine (6-BAP) (1 mg/l) and 1-naphthaleneacetic acid (NAA) (0.1 mg/l) was overlaid with Nicotiana tabacum var Samsun suspension culture (1 cm$^3$). One 9 cm and one 7 cm filter paper discs were placed on the surface.

Whole leaves from tissue culture grown plants were placed in the feeder plates. The plates were sealed with "NESCOFILM" (Trade Mark) and incubated overnight in a plant growth room (26° C. under bright fluorescent light).

Leaves from the feeder plates were placed in Agrobacteria suspension in 12 cm diameter petri dishes and cut into 1–1.5 cm² sections. After 20 minutes the leaf pieces were returned to the feeder plates which were sealed and replaced in the growth room. After 48 hours incubation in the growth room the plant material was transferred to MS medium supplemented with 6-BAP (1 mg/1), NAA (0.1 mg/1), carbenicillin (500 μg/cm³) and kanamycin (100 μg/cm³), in petri dishes. The petri dishes were sealed and returned to the growth room.

Beginning three weeks after inoculation with Agrobacterium, shoots were removed from the explants and placed on MS medium supplemented with carbenicillin (200 μg/cm³) and kanamycin (100 μg/cm³) for rooting. Transformed plants rooted 1–2 weeks after transfer.

Following rooting, transformed plants were transferred to pots containing soil and grown in the glasshouse. Roughly one month after transfer the plants flowered.

The anthers of the tobacco plants containing the pMS10-6GUS construct were sprayed for GUS activity using standard procedures.

IV. Disrupter Protein Gene

This module contains a gene, expressible in plants, to inhibit mitochondrial function, hence disrupting full expression of a selected plant characteristic.

Accordingly we provide a method of inhibiting gene expression in a target plant tissue comprising stably transforming a plant cell of a type from which a whole plant may be regenerated with a gene construct carrying a tissue-specific or a development-specific promoter which operates in the cells of the target plant tissue and a disrupter gene encoding a protein which is capable, when expressed, of inhibiting respiration in the cells of the said target tissue resulting in death of the cells.

Preferably the disrupter gene is selected from:
(a) The mammalian uncoupling protein (UCP) cloned from mammalian (usually rat) brown adipose tissue.
(b) A mutated form of the gene for the β-subunit of $F_1$-ATPase which has sequences added or deleted such that these changes result in the retention of the ability to assemble with other subunits but interfere with function as an ATP synthase. The ability of these altered subunits to assemble correctly will be important as the required phenotypic effect of their expression will depend on their competition with wild-type subunits for binding sites in the enzyme complex. Thus complexes containing non-functional subunits will only be weakly active and mitochondria harbouring these complexes will be non-functional.
(c) A mutated, synthetic form of the oli 1 gene encoding subunit 9 of the $F_o$-ATPase. Mutations created as described at (b) above.
(d) A mutated form of a mitochondrial transit pre-sequence which malfunctions during transfer resulting, probably by blocking of receptor sites, in the disruption of protein transport to mitochondria.
(e) Gene constructs involving a fusion between the β-subunit gene from yeast and the β-glactosidase gene from E. coli, resulting in expression of a disrupting fusion protein.

Preferably the promoter is a tapetum-specific promoter or a pollen-specific promoter, so that on expression of the said disrupter protein therein the regenerated plant is in male sterile. More preferably the said tapetum-specific promoter has the sequence shown in FIGS. 15A to 15G, 16A to 16C, or 17A to 17E of the accompanying drawings.

The isolation and characterisation of these gene control sequences of this invention are described in section III above.

This module, therefore, provides a method of preventing or inhibiting growth and development of plant cells based on gene constructs which inhibit respiratory function. The technique has wide application in a number of crops where inhibition of particular cells or tissue is required.

Of particular interest is the inhibition of male fertility in maize for the production of F1 hybrids in situ. The concept of inhibition of mitochondrial function as a mechanism for male sterility arises from some previous research on T-type cytoplasmic male sterility in maize (cms-T) which has shown an association between the male sterile phenotype and mitochondrial dysfuction. Although a direct causal relationship has yet to be established between mitochondrial dysfunction and cms-T, an increasing body of evidence suggests that fully functional mitochondria, particularly in the tapetal cells, are essential. This is particularly critical during microsporogenesis since the metabolic demands placed on the tapetal cells results in a 40-fold increase in mitochondrial number.

Thus we provide a number of negative mutations which act upon mitochondria to uncouple oxidative phosphorylation. When specifically expressed in maize anther tissue these mutations will result in a male sterile phenotype.

The proposed disrupter protein, UCP, is instrumental in the thermogenesis of mammalian brown adipose tissue and exists as a dimer in the mitochondrial inner membrane forming a proton channel and thus uncoupling oxidative phosphorylation by dissipation of the proton electrochemical potential differences across the membrane.

An alternative is the use of chimeric gene constructs in which domains are swapped, creating non-functional proteins. The target proteins here are the β-subunit of $F_1$-ATPase and subunit 9 of the $F_0$- ATPase. During assembly of functional ATPase complexes, the altered chimeric subunits will complete for binding sites normally occupied by the naturally occurring subunits, particularly when the chimeras are over expressed compared with the endogenous genes. Mitochondrial function will be disrupted since $F_1$ and $F_0$ ATPase's assembled with altered subunits are likely to be weakly active or non-functional.

The method employed for transformation of the plant cells is not especially germane to this invention and any method suitable for the target plant may be employed. Transgenic plants are obtained by regeneration from the transformed cells. Numerous transformation procedures are known from the literature such as agroinfection using *Agrobacterium tumefaciens* or its Ti plasmid, electroporation, microinjection of plant cells and protoplasts, microprojectile transformation and pollen tube transformation, to mention but a few. Reference may be made to the literature for full details of the known methods.

The development and testing of these gene constructs as disrupters of mitochondrial function in the unicellular organism, yeast, will now be described. A mechanism by which these gene constructs may be used to inhibit plant cell growth and differentiation in transformed plants will also be described. The object of these procedures is to use yeast as a model system for the identification and optimisation of gene constructs for expressing proteins which disrupt mitochondrial function. Plant cells will then be transformed with the selected constructs and whole plants regenerated therefrom.

Specific embodiments of the module will now be illustrated by the following Example.

EXAMPLE

It was known from reports in the literature that the rat UCP gene inserted in the yeast/*E. coli* shuttle vector gave only low levels of expression of UCP. The yeast was *Saccharomyces cerevisiae* strain YM147 and the UCP gene was available on plasmid pCGS110-UCP.

Given the lack of useful expression levels with the wild type gene, modification of the rat UCP gene using site directed mutagenesis was carried out. the following modifications were made:

1. Introduction of a BamHI site seven nucleotides 5' to the AUG methionine initiation codon;
2. Modification of the sequence around the AUG methionine initiation codon to conform to the yeast consensus sequence ATAATG;
3. Deletion of an internal BamHI site; and,
4. Introduction of a BamHI site one nucleotide 3' to the TAG termination codon.

These modifications result in the deletion of the untranslated 5' and 3' rat UCP sequences as well as the introduction of a yeast consensus sequence at the methionine initiation codon.

Figure 24:
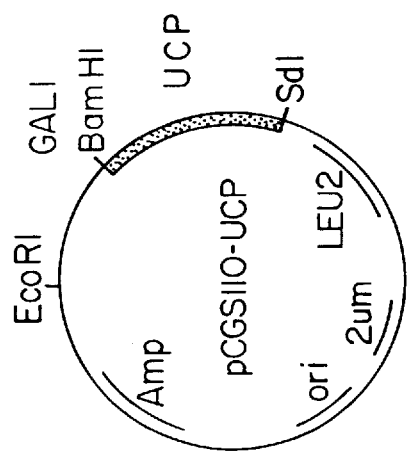
FIG. 24 is a map of plasmid pCGS110-UCP.

The 1.9 kb EcoRI/PstI fragment from the plasmid pCGS110-UCP (a map of the plasmid is shown in FIG. 24 and the mRNA sequence of the UCP gene is shown in FIG. 25) carrying the GAL10 promoter region and the rat UCP cDNA was cloned into the EcoRI/PstI sites of M13mp19 DNA. Sequencing of the resultant construct was carried out to ensure the correct structure.

Site directed mutagenesis was carried out according to the directions given in the Amersham (Trade Mark) mutagenesis kit using three different oligonucleotides as follows:

| UCP-1 | wild type | CTCTGCCCTCCGAGCCAAGATGGTGAGTT |
|---|---|---|
|  | mutant | CTCTGCCCTCGGATCC(ATAATG)GTGAGTT |
| UCP-2 | wild type | TGCGACTCGGATCCTGGAACG |
|  | mutant | TGCGACTCGGTTCCTGGAACG |
| UCP-3 | wild type | ACCACATAGGCGACTTGGAG |
|  | mutant | ACCACATAGGATCCGACTTGGAG |

Oligonucleotide UCP-1 was used to introduce the yeast consensus sequence (bracketed) which occurs around the methionine initiation codon, as well as the introduction of the BamHI cleavage site (underlined).

Oligonucleotide UCP-2 was used to delete an internal BamHI site (underlined).

Oligonucleotide UCP-3 was used to introduce BamHI site immediately after the TAG stop codon (underlined).

These three mutations allowed the isolation of the entire UCP coding sequence on a 0.93 kb fragment.

After selection of mutant clones the modified DNA was digested with BamHI. Three clones from twenty selected gave inserts of 0.93 kb upon digestion with BamHI.

Sequencing of the clones UCPS1 and UCPS4 revealed that the UCP gene had been correctly modified with no unwanted changes present. The UCP gene was then transferred to the yeast expression plasmid pKV49 which allows expression of foreign genes in *S. Cerevisiae* under the control of the strong PGK promoter and the GAL1-10 UAS allowing induction/repression of the foreign gene according to whether or not galactose is present in the growth medium. The 0.93 kb BamHI fragment containing the modified UCP gene was cloned into pKV49 at the BglII restriction site, resulting in the construct pKV49-UCP.

Transformation of Yeast With pKV49-UCP Construct a) Development of Suitable Yeast Strain For a recipient for the pKV49-UCP construct we needed a yeast strain carrying the appropriate markers for transformation and allowing induction of gene expression from the GAL1-10 UAS while being unable to utilise glactose as a carbon and energy source (GAL1, GAL2). Such strains were generated by mating yeast strains YM147 and SF747. After selection of diploids on minimal plates containing uracil, the colonies were transferred to sporulating media. The resulting spores were grown on YDP plates prior to the resulting yeast colonies being characterised (FIG. 26). Two new yeast strains BET9 (ura3, trpl1, leu2, his3, gal1) and BE27 (ura3, trp1, leu2, gal1) were isolated, both of which are suitable for transformation with PkV49 based constructs.

b) Yeast Transformation

Yeast strains BET9 and BE27 were transformed with pKV9 and pKV49-UCP DNA; transformants were selected using the appropriate auxotrophic selection (leu) and checked by plasmid isolation followed by restriction mapping. Single colonies from each of the four different transformants BET9/pKV49, BET9/pKV49-UCP, BE27/pKV49 and BE27/pKV49-UCP) were resuspended in sterile water prior to being spotted onto plating media containing a variety of carbon sources (FIG. 27) both in the presence and absence of galactose. Results from these plate tests (FIG. 27) indicated that on a few of the carbon sources used, the presence of both galactose and the pKV49-UCP construct resulted in poorer growth of the resulting yeast colonies. The greater effect on retardation of growth was observed with the glycerol/casamino (gly/cas) medium containing glactose for both pKV49-UCP transformants. Transformants either lacking the UCP gene or induced by galactose grew at the same rate as the untransformed BET9 and BE27 strains.

Growth Curve Analysis

Figure 28B:
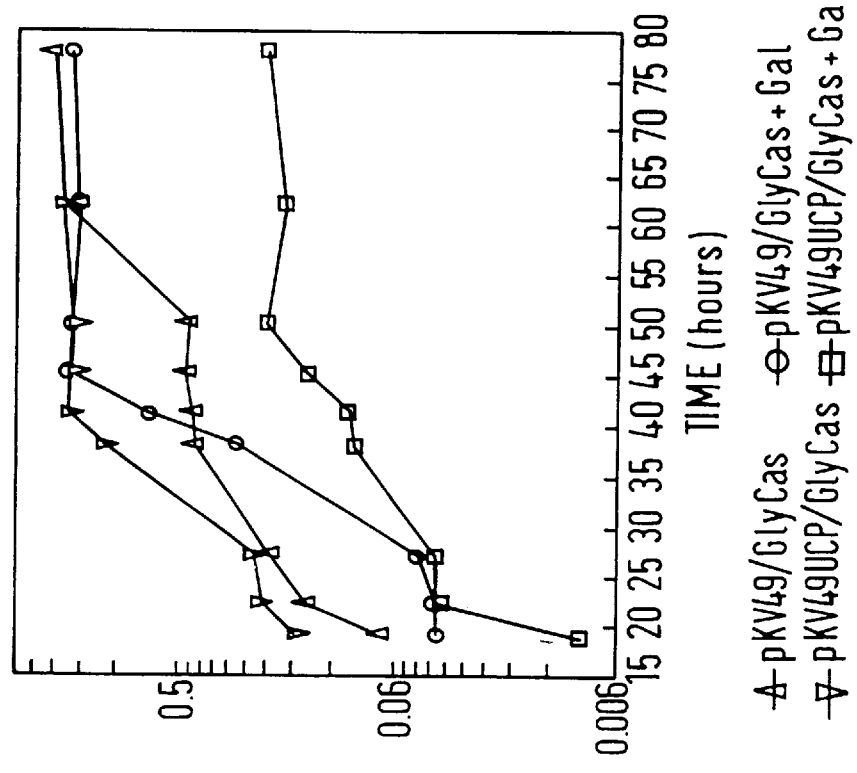
FIGS. 28A to 28B show results of growth curve analysis of BET9 and BET27 (FIG. 26B) transformants grown on gly/cas medium over a period of 65 hours in the presence or absence of galactose.
Figure 28A:
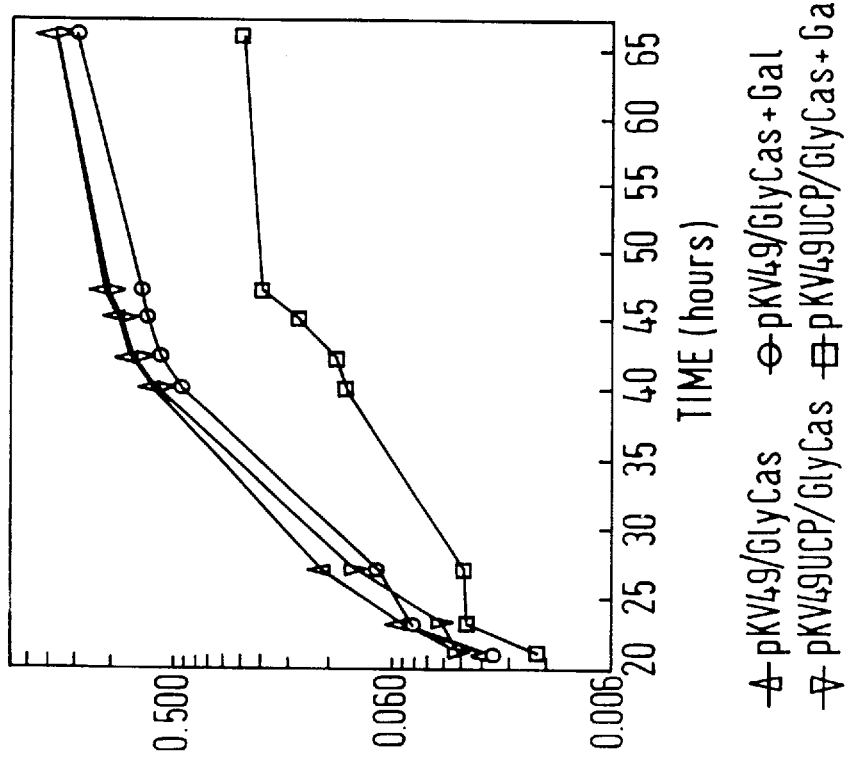

As plating tests had indicated poor growth of pKV49-UCP transformants on gly/cas medium in the presence of galactose, growth curve analysis in liquid culture was carried out to determine more accurately the magnitude of the growth defect. The results in FIGS. 28A to 28B substitute the results of plating tests and indicate that neither the presence of pKV49-UCP DNA or galactose alone is sufficient to have any effect on the yeast cell growth rates, while the presence of both severely retards growth. As our initial results using the yeast strain YM147 transformed with the construct pCGS110-UCP had not shown any significant growth defect on any of the tested carbon sources in the presence of galactose, it would appear that the modification of the UCP gene and/or the use of a different vector (pKV49) have resulted in an observable growth defect.

Analysis of UCP Expression

Figure 29:
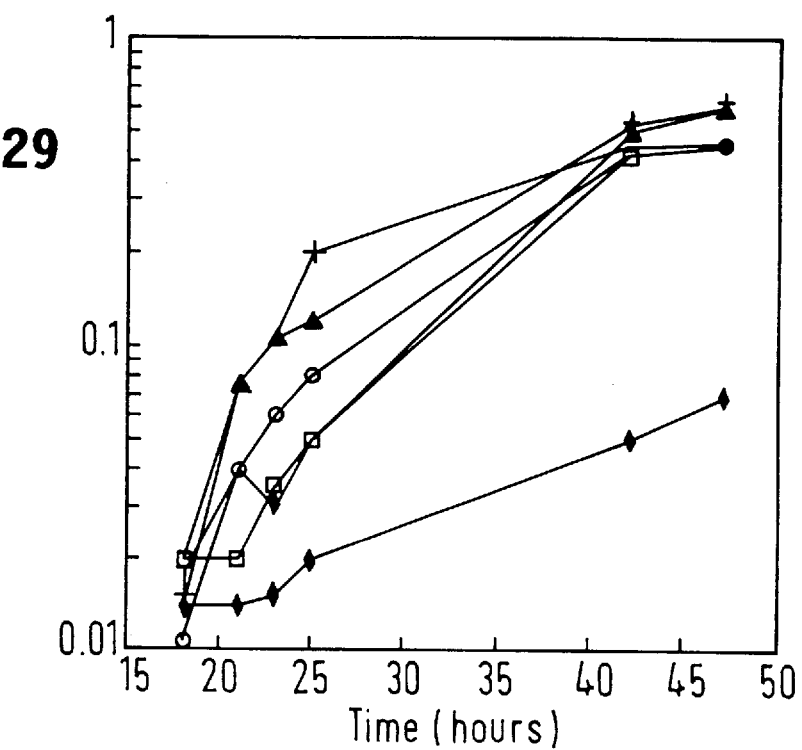
FIG. 29 is the growth curve analysis of rat UCP in strain BET9 grown on gly/cas medium over a period of 50 hours in the presence or absence of galactose.

As the growth curve analysis had indicated no detectable differences between the BE27 and BET9 transformants (FIGS. 28A to 28B), it was decided only to use the BET9 transformants in subsequent experiments. Repeat growth analysis on gly/cas medium both in the presence and absence of galactose was carried out with the BET9 transformants. Cultures were allowed to grow for 47 hours to ensure that the same growth curve characteristics observed previously (FIG. 29) were repeated. Cells were then harvested, total cell proteins were isolated and fractionated (in duplicate) by SDS-PAGE on a 10% polyacrylamide gel. One set of fractionated proteins were stained with Coomassie Blue to ensure equal loading of the proteins while the other set were transferred to nylon membrane and subjected to Western blot analysis using the rat UCP antibody. The Western blot showed two main features:

1) The comparative level of UCP expression between the BET9/pKV49-UCP transformant and the VY147/pCGS110-UCP transformant reveals that the UCP expression has increased approximately 50–100 fold as a consequence of our modifications.
2) The yeast transformant which exhibits defective growth when grown on gly/cas medium in the presence of galactose also expresses substantial amounts of UCP.

It can be concluded from these results that the modification of the UCP gene and/or its subsequent cloning into the pKV49 vector has resulted in the increased level of UCP expression relative to the levels initially detected with the pCGS110-UCP construct. Growth curve analysis indicates that the expression of UCP has an effect on the growth rates of yeast cells grown under certain conditions. As yet we have not been able to identify the specific effect that the increased levels of UCP expression have on yeast cell growth rates but preliminary results implicate a mitochondrial defect.

Figure 30:
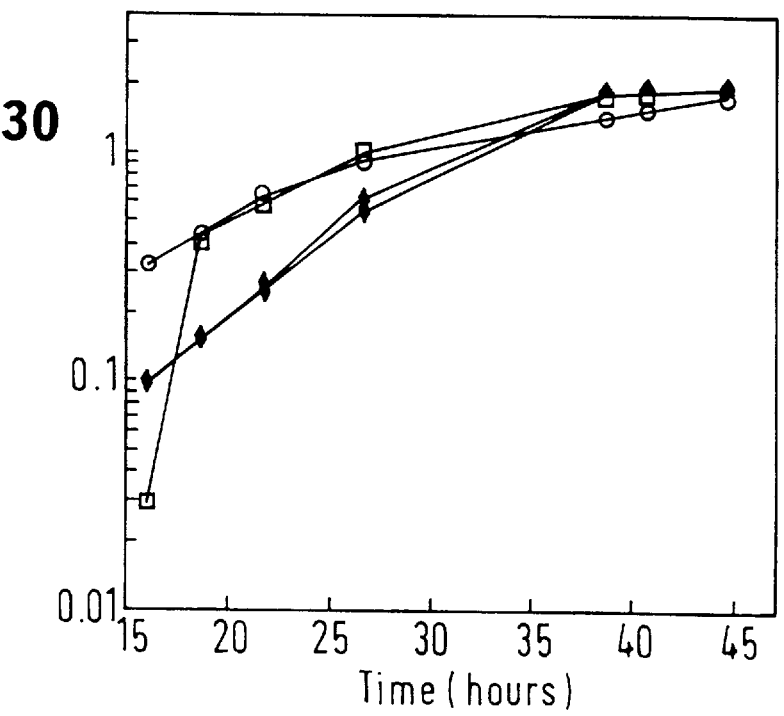
FIG. 30 is the growth curve analysis of rat UCP in strain BET9 grown on raffinose medium over a period of 45 hours in the presence or absence of galactose.

Growth curve analysis carried out in the raffinose medium (a fermentable carbon source which should not affect Gal regulation) of the BET9 transformants grown in the presence or absence of galactose indicate that the presence of both the UCP gene and galactose has no effect on growth rates (FIG. 30). Western blot analysis of the proteins isolated from cells harvested during these growth curves reveals levels of UCP expression similar to those found in cells grown in gly/cas medium in the presence of galactose.

The UCP detected in BET9/pKV49-UCP transformants grown without added galactose is probably due to galactose residues released into the medium by hydrolysis of raffinose, possibly during the autoclaving. These observations indicate that the presence of UCP in yeast cells grown on a fermentable carbon source (no requirement for oxidative phosphorylation) has no effect on cell growth rates, while cells growing on the gly/cas medium (a non-fermentable carbon source) expressing UCP exhibit defective growth.

Location of UCP in Yeast Cells

Rat UCP is a major component of the mitochondrial inner membrane of brown adipose tissue. Unlike many other polypeptides found in the inner membrane it does not contain a cleavable signal sequence, the targeting information being encoded internally within the amino acid sequence of the protein. As our results indicate that the expressed UCP has an effect on the rate of yeast cell growth then it is important to determine the precise location of the protein expressed in yeast cells. Initial Western blot analysis of total mitochondrial proteins shows the UCP expressed by the pKV49-UCP transformant to be located in the mitochondrial fraction.

Subsequent mitochondrial fractionation revealed that the majority of the UCP is located in the inner membrane fraction of yeast mitochondria. Although some of the UCP appears to be located in the inner-membrane space, this observation is most likely due to contamination of this fraction with some of the inner membrane fraction. Similar results have been obtained with the location of the β-subunit of the $F_1$-ATPase complex from yeast cell mitochondria. The β-subunit which is a component of the inner membrane is also detected in our inter-membrane space preparations. However, these results do show that the targeting information within the rat UCP is sufficient to target the UCP to the inner membrane of yeast mitochondria where it could function a an uncoupler protein.

UCP Transcript Analysis

RNA has been isolated from many of the growth curve experiments described previously. We are currently carrying out Northern blot analysis in order to determine whether the patterns of UCP expression are reflected by the UCP transcript signals

Effect of Copy Number on UCP Expression

The transformation of yeast cells with shuttle vectors containing the origin of replication from the yeast 2 μm circle, such as pKV49-UCP, results in these plasmids being present at approximately 40–50 copies per cell. Consequently any foreign gene carried by the plasmid will be present at the same relatively high copy number which may result in the expression of the foreign protein at a higher level than would be seen for a gene present at a low copy number. We have therefore attempted to lower the copy number of the UCP gene by integrating it into the yeast chromosome at a single site resulting in a genetically stable, single-copy transformant. The vector YIp5 (FIG. 31) is an integrating yeast vector carrying the ura3 gene; it is unable to replicate autonomously in yeast.

The 1.8 kb EcoRI/SalI fragment from pKV49-UCP containing the rat UCP gene along with the PGK promoter and GAL UAS was cloned into the EcoRI/SALI sites of YIp5 DNA. The resultant plasmid UIP-UCP (FIG. 31) was checked by restriction enzyme mapping to ensure the UCP gene was correctly inserted. The YIP-UCP plasmid was cut with the restriction enzyme EcoRV (which cuts in the middle of the URA3 gene (FIG. 31) and the linearised YIP/UCP DNA was used to transform the yeast cell lines BET9 and BE27. Transformants were initially screened on minimal plates by selecting for uracil prototrophy and after 7–10 days two transformants from each cell line were streaked out onto YPD plates (non-selective). The transformants were then subjected to four consecutive periods of growth on non-selective medium. One hundred colonies from each of the original four transformants were then replica plated onto both non-selective (YDP) and selective media (minimal plants+ ura). All colonies grew on the selective media indicating that the URA3 gene, which is genetically linked to the UCP gene (FIG. 31), had been integrated to the yeast cell chromosome. Chromosomal DNA was isolated from each of the four transformants, digested with the restriction enzyme EcoRI and fractionated on a 0.08% agarose gel. Southern blot analysis using a labelled UCP probe indicated that the UCP gene is present in the yeast chromosome of all four transformants. Western blot analysis using the rat UCP antibody will show the level of UCP expression in these transformants. Growth curve analysis of these transformants grown in the presence of galactose shows that they may have growth inhibition consistent with a mitochondrial defect.

EXAMPLE 3
Modification of the β-Subunit of $F_1$Atpase

The second approach we have taken to introducing mutations affecting mitochondrial function is the directed modification of functional mitochondrial proteins which when expressed in yeast might be expected to interfere with the generation of ATP. The protein chosen for this approach is the β-subunit of the $F_1$-ATPase complex. The DNA sequence of the yeast β-subunit gene is known and the gene has been independently cloned and sequenced in our laboratory 918).

The F₁ATPase portion of ATP synthase catalyses the terminal step of oxidative phosphorylation $F_1$ is an assembly of five different polypeptides designated α, β, γ, δ, and ε. Experiments carried out by Parsonage et al on modification of the β-subunit of $F_1$-ATPase from *E. coli* identified specific amino acid residues of the β-subunit that appear to be very important for catalysis of both ATP synthesis and hydrolysis. Two mutations in particular were shown to result in greatly impaired catalysis without causing major structural perturbation of the $F_1$-ATPase. One of these mutations resulted from changing the strongly conserved lysine residue occurring in the catalytic nucleotide-binding domain at position 155 to a glutamine residue while the other mutation resulted from changing the methionine residue at position 209 to a leucine residue. Both of these mutations have been reposed to exert their effect by the prevention of confirmational changes required from the catalytic cooperativity in the $F_1$ complex.

As the assembly of these mutated β-subunit proteins into the $F_1$-ATPase is not affected, then it was felt that similar mutants of the β-subunit in yeast might compete for assembly into $F_1$-ATPase. It was thought that the result of having both wild-type and mutated β-subunits in the same $F_1$-ATPase would perhaps result in impaired catalysis resulting in a decrease in ATP production and retarded cell growth.

The β-subunit of $F_1$-ATPase from a wide variety of sources has been shown to by highly conserved at the amino acid sequence and comparison of the S cerevisiae β-subunit amino acid sequence with that from *E. Coli* confirms that the lysine and methionine residues shown by Parsonage et al to be very important for catalytic activity are conserved, with the lysine and methionine residues occurring at positions 196 and 255 respectively on the yeast β-subunit sequence.

In order to carry out SDM the wild-type β-subunit gene from yeast was isolated from the plasmid pGR208 (FIGS. 32A to 32B) as an EcoRI/BamHI fragment which was cloned into M13mp19. Two mutated β-subunit genes were constructed: mutant BB1 has both the Met255 and Lys196 converted to isoleucine and glutamine respectively while mutant BB2 has only the lysine to glutamine mutation (FIGS. 32A to 32B). Following sequence analysis to ensure correct mutagenesis with no unwanted mutations, the mutated β-subunit genes were removed from mp19 by EcoRI/BamHI digests. The fragments containing the genes were then blunt-ended and ligated to BglII digested pKV49 (FIGS. 33A to 33B) which had previously been blunt-ended. We have both mutated β-subunit genes cloned into pKV49 (pKV49-BB1 and pKV49-BB2) and have transformed the yeast strain BET9 with both these constructs. Growth curve and plate growth from both mutated β-subunit transformants show tht the transformants have altered growth characteristics which are consistent with a mitochondrial defect.

Concurrently with the transformation of strain BET9 with the mutated β-subunit genes, gene disruption may be used to construct a derivative of strain BET9 which will fail to synthesize β-subunit. The resultant strain will therefore be unable to grow on non-fermentable carbon sources although it will be easily maintainable on a fermentable carbon source such as glucose. Transformation of this strain with plasmids bearing the mutated β-subunit genes, followed by measuring the transformants' growth characteristics on a non-fermentable carbon source, shows that the altered β-subunit is unable to support oxidative phosphorylation.

EXAMPLE 4
FUSION PROTEINS

An alternative strategy for selectively perturbing mitochondrial function is the expression of a fusion protein which results in either poor or no yeast cell growth. The candidate fusion protein chosen from this project contains the N-terminal region of the yeast ATP synthase β-subunit fused to most of β-galactosidase from *E. coli* and has been constructed by gene fusion (FIGS. 34A to 34B). This β-subunit/β-galactosidase fusion protein has already been shown to be targeted to the inner membrane of yeast mitochondria 921) and cells expressing this fusion protein appear to be unable to grow on a non-fermentable carbon source. In the presence of the fusion protein the transducing capacity of the mitochondrial membrane as measured by the $^{32}P$-ATP exchange reaction is only 9% of that measured in the absence of the fusion protein. As yet the mechanism of this description has not been evaluated but the gene fusion is thought to produce a protein which becomes trapped in the inner membrane and interferes with function(s) essential for respiratory growth.

CONSTRUCTION OF THE ATP2/LacZ GENE FUSION

The plasmid pGR208, which contains the yeast ATP2 DNA encoding ATP synthase β-subunit gene (FIGS. 32A to 32B), was digested with EcoRI plus BamHI resulting in the release of a 1.1 kb fragment coding for the first 350 amino acids of the β-subunit protein. pMUR1720 is a pUC8 based plasmid which contains a LacZ gene contained within an EcoRI/NarI fragment (FIGS. 34A to 34B). Cloning of the 1.1 kb EcoRI/BamHI DNA fragment coding for the first 350 amino acids of the yeast β-subunit protein into the EcoRI/BamHI sites of pMUR1720 (FIG. 34A) results in an in-frame fusion between the 350 amino acids of the β-subunit and the entire (minus the first eight amino acids) LaZ protein (FIGS. 34A to 34B). The entire β-subunit/LacZ gene fusion is now contained on the 4.3 kb EcoRI/NarI fragment in construct pMUR1720-BLZ (FIGS. 34A to 34B). This 4.3 kb EcoRI/NarI fragment is currently being cloned into the pKV49 vector resulting in the pKV49-BLZ construct (FIG. 35) which can be used to transform the yeast strains BET9 and BE27 and show that when induced by galactose growth defects consistent with mitochondrial inhibition arise.

EXAMPLE 5
Construction of a promoter fusion between the MS10 gene and the UCP gene The 1830 bp HindIII to BamH1 fragment from pMS10 was ligated into the binary plant transformation vector Bin19 previously cut with HindIII and BamH1.

Following ligation the resultant plasmid was cut with BamH1 and ligated to the 930 bp UCP BamH1 fragment from plasmid pUC/UCP (s derivative of pUC19 contyaininbg the modified UCP gene cloned at the BamH1 site) to construct a fusion between the MS10 gene promoter and the UCP gene. Finally the nos 3' terminator obtained as a 250 bp Sst1- EcoR1 fragment from vector pTAK1 wasligated into the MS10-UCP construct previouslt cut with Sst1 and EcoR1.

Figure 37:
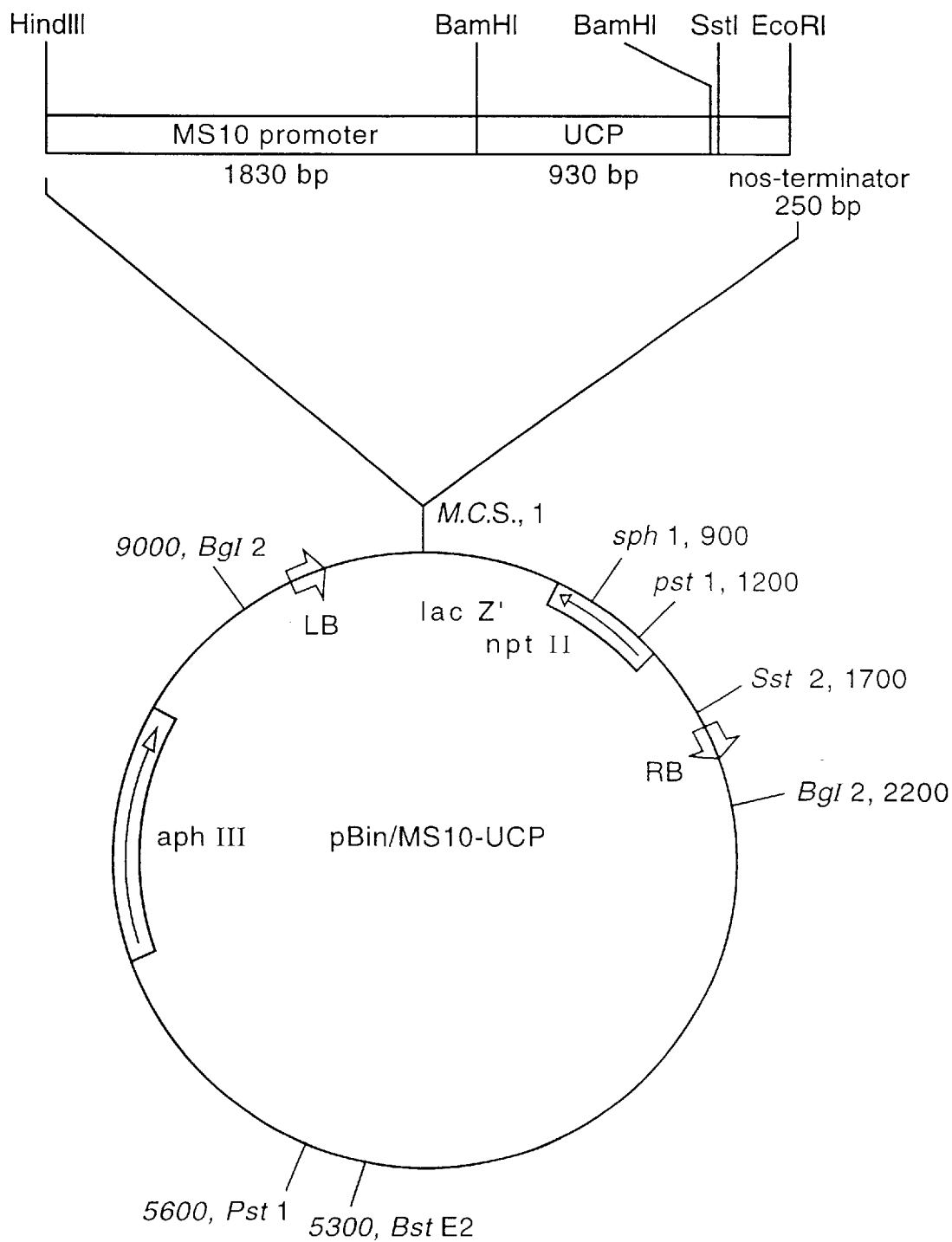
FIG. 37 is a plasmid map of pBin/MS10-UCP.

The resulting plasmid is termed pBin/MS10-UCP (FIG. 37) and contains the MS10 promoter, the UCP gene, nos 3' terminator expression cassette located between the right and left border sequences of Agrobacterium T-DNA allowing efficient transformation into tobacco cells.

EXAMPLE 6
Transformation of tobacco plants with pBin/MS10 promoter gene constructs The recombinant vector pBin/MS10-UCP was mobilised from *E Coli* (TG-2) onto *Agrobacterium tumefaciens* (LBA4404) in a triparental mating on L-plates with *E Coli* (HB101) harbouring pRK2013. Transconjugants were selected on minimal medium containing kanamycin (50 μg/cm³) and streptomycin (500 μg/cm³).

L-Broth (5 cm³) containing kanamycin at 50 g/cm³ was inoculated with a single Agrobacterium colony. The culture was grown overnight at 30° C. with shaking at 150 rpm. This culture (500 μl) was inoculated into L-Broth containing kanamycin (50 μg/cm³) and grown as before. Immediately before use the Agrobacteria were pelleted by spinning at 3000 rpm for 5 minutes and suspended in an equal volume of liquid Murashige and Skoog (MS) medium.

Feeder plates were prepared in 9 cm diameter petri dishes as follows. Solid MS medium supplemented with 6-benzyl-aminopurine (6-BAP) (1 mg/l) and 1-naphthaleneacetic acid (NAA) (0.1 mg/l) was overlaid with *Nicotiana tabacum* var Samsun suspension culture (1 cm³). One 9 cm and one 7 cm filter paper discs were placed on the surface.

Whole leaves from tissue culture grown plants were placed in the feeder plates. The plates were sealed with "NESCOFILM" (Trade Mark) and incubated overnight in a plant growth room (26° C. under bright fluorescent light).

Leaves from the feeder plates were placed in Agrobacteria suspension in 12 cm diameter petri dishes and cut into 1- 1.5 cm² sections. After 20 minutes the leaf pieces were returned to the feeder plates which were sealed and replaced in the growth room. After 48 hours incubation in the growth room the plant material was transferred to MS medium supplemented with 6-BAP (1 mg/l), NAA (0.1 mg/l), carbenicillin (500μg/cm³) and kanamycin (100 μg/cm 3), in petri dishes. The petri dishes were sealed and returned to the growth room.

Beginning three weeks after inoculation with Agrobacterium, shoots were removed from the explants and placed on MS medium supplemented with carbenicillin (200 μg/cm³) and kanamycin (100 μg/cm³) for rooting. Transformed plants rooted 1–2 weeks after transfer.

Following rooting, transformed plants were transferred to pots containing soil and grown in the glasshouse. Roughly one month after transfer the plants flowered.

The anthers of the tobacco plants containing the pBin/MS10-UCP construct were were assayed for expression of the UCP gene by Northern blotting of RNA samples, and the effect of UCP expression on pollen development determined.

We claim:

1. A plant gene construct comprising:
   (a) a first promoter sequence responsive to the presence or absence of an exogenous chemical inducer,
   (b) a first structural gene sequence encoding a repressor protein operably linked and under the control of said first promoter sequence,
   (c) an operator sequence responsive to the repressor protein expressed by said first structural gene sequence,
   (d) a male flower specific second promoter sequence selected from the group consisting of pMS10, pMS14 and pMS18, having NCIB accession No.'s 40090, 40099 and 4100, respectively,
   (e) a second structural gene sequence encoding a protein which, when expressed, disrupts pollen biogenesis operably linked to said second promoter sequence.

2. The plant gene construct of claim 1 in which said first promoter sequence is a 27 kd subunit isolated from the maize glutathione-S-transferase (GSTII) gene.

3. The plant gene construct of claim 2 in which the exogenous chemical inducer for the first promoter is selected from the group consisting of N,N-diallyl-2,2-dichloro-acetamide and benzyl-2-chloro-4-(trifluoro-methyl)-5-thioazole-carboxylate.

4. The plant gene construct of claim 3 in which the exogenous chemical inducer for said first promoter is N,N-diallyl-2,2-dichloro-acetamide.

5. The plant gene construct of claim 1 in which said first structural gene encodes a DNA-binding protein which upon expression inhibits expression of said second structural gene sequence.

6. The plant gene construct of claim 5 in which said DNA-binding protein and said operator sequence are of non-plant origin.

7. The plant gene construct of claim 7 in which said DNA-binding protein and said operator sequence are of bacterial origin.

8. The plant gene construct of claim 8 in which said DNA-binding protein and said operator sequence are derived from the lacI gene of *Escherichia coli*, isolated from the plasmid p35SlacI, and deposited in an *Escherichia coli*, strain TG-2, host under NCIB Accession No. 40092.

* * * * *